(12) United States Patent
Henri et al.

(10) Patent No.: US 9,611,186 B2
(45) Date of Patent: *Apr. 4, 2017

(54) SYNTHESIS OF HIGH CALORIC FUELS AND CHEMICALS VIA KETENE AND DIKETENE INTERMEDIATES

(71) Applicant: Pioneer Energy, Inc., Lakewood, CO (US)

(72) Inventors: John Henri, Longmont, CO (US); Jan Zygmunt, Longmont, CO (US); Mark Berggren, Golden, CO (US); Robert Zubrin, Golden, CO (US)

(73) Assignee: PIONEER ENERGY, Lakewood, CO (US)

( * ) Notice: Subject to any disclaimer, the term of this patent is extended or adjusted under 35 U.S.C. 154(b) by 626 days.

This patent is subject to a terminal disclaimer.

(21) Appl. No.: 13/672,568

(22) Filed: Nov. 8, 2012

(65) Prior Publication Data
US 2013/0118063 A1 May 16, 2013

Related U.S. Application Data

(60) Provisional application No. 61/558,321, filed on Nov. 10, 2011, provisional application No. 61/577,903, (Continued)

(51) Int. Cl.
*C10L 1/18* (2006.01)
*C07B 41/02* (2006.01)
(Continued)

(52) U.S. Cl.
CPC ............... *C07B 41/02* (2013.01); *C07C 1/24* (2013.01); *C07C 5/03* (2013.01); *C07C 29/145* (2013.01);
(Continued)

(58) Field of Classification Search
CPC .......... C10L 1/1824; C10L 1/023; C10L 1/06; C07B 41/02; C07C 29/149; C07C 29/145;
(Continued)

(56) References Cited

U.S. PATENT DOCUMENTS 2,080,562 A 5/1937 Eschenbach
2,175,811 A 10/1939 Loder
(Continued)

FOREIGN PATENT DOCUMENTS

GB 478213 1/1938
GB 918623 2/1963

OTHER PUBLICATIONS

Pomerantz, Synthesis and physical properties of n-heptane and 2,2,4-trimethylpentane, 1952, J. of Res. of the Nat. Bureau of Std., pp. 76-81.
(Continued)

*Primary Examiner* — Cephia D Toomer
(74) *Attorney, Agent, or Firm* — Sam L. Nguyen; Hamilton, DeSanctis + Cha, LLP

(57) ABSTRACT

In one embodiment, the present application discloses methods to selectively synthesize higher alcohols and hydrocarbons useful as fuels and industrial chemicals from syngas and biomass. Ketene and ketonization chemistry along with hydrogenation reactions are used to synthesize fuels and chemicals. In another embodiment, ketene used to form fuels and chemicals may be manufactured from acetic acid which in turn can be synthesized from synthesis gas which is produced from coal, biomass, natural gas, etc.

14 Claims, 12 Drawing Sheets

Synthesis of butanol from acetic acid via diketene.

Related U.S. Application Data filed on Dec. 20, 2011, provisional application No. 61/614,937, filed on Mar. 23, 2012, provisional application No. 61/643,447, filed on May 7, 2012, provisional application No. 61/667,093, filed on Jul. 2, 2012.

(51) Int. Cl.
| | |
|---|---|
| C10L 1/182 | (2006.01) |
| C07C 29/149 | (2006.01) |
| C07C 29/145 | (2006.01) |
| C07C 29/17 | (2006.01) |
| C07C 1/24 | (2006.01) |
| C07C 45/48 | (2006.01) |
| C07C 51/12 | (2006.01) |
| C07D 309/36 | (2006.01) |
| C07C 5/03 | (2006.01) |
| C10L 1/02 | (2006.01) |
| C10L 1/06 | (2006.01) |
| C10G 3/00 | (2006.01) |

(52) U.S. Cl.
CPC .......... *C07C 29/149* (2013.01); *C07C 29/177* (2013.01); *C07C 45/48* (2013.01); *C07C 51/12* (2013.01); *C07D 309/36* (2013.01); *C10G 3/50* (2013.01); *C10L 1/023* (2013.01); *C10L 1/06* (2013.01); *C10L 1/1824* (2013.01); *C10G 2400/02* (2013.01)

(58) Field of Classification Search
CPC .......... C07C 5/03; C07C 29/177; C07C 1/24; C07D 309/36; C07D 45/48; C07D 51/12; C10G 3/50
USPC ..... 44/451, 452; 585/14; 568/832, 881, 885, 568/876, 884
See application file for complete search history.

(56) References Cited

U.S. PATENT DOCUMENTS

| | | |
|---|---|---|
| 2,450,133 A | 9/1948 | Hagemeyer, Jr. |
| 2,484,486 A | 10/1949 | Caldwell |
| 2,484,498 A | 10/1949 | Hagemeyer, Jr. |
| 2,763,664 A | 9/1956 | Sixt |
| 2,802,872 A | 8/1957 | Sturzenegger |
| 2,820,058 A | 1/1958 | Luke, Jr. et al. |
| 3,014,962 A | 12/1961 | Reppe et al. |
| 3,057,912 A | 10/1962 | Enk et al. |
| 3,117,156 A | 1/1964 | Keller et al. |
| 3,366,689 A | 1/1968 | Maeda et al. |
| 3,759,955 A | 9/1973 | Jacobs et al. |
| 3,865,846 A | 2/1975 | Schulz et al. |
| 4,081,253 A | 3/1978 | Marion |
| 4,311,854 A | 1/1982 | Weber et al. |
| 4,348,541 A | 9/1982 | Doyle |
| 4,455,439 A | 6/1984 | Arnold et al. |
| 4,727,200 A | 2/1988 | Wegman et al. |
| 4,754,074 A | 6/1988 | Hussmann |
| 4,954,665 A | 9/1990 | Vidal |
| 4,994,608 A | 2/1991 | Torrence et al. |
| 4,996,333 A | 2/1991 | Berg |
| 5,001,259 A | 3/1991 | Smith et al. |
| 5,030,609 A | 7/1991 | Turner et al. |
| 5,144,068 A | 9/1992 | Smith et al. |
| 5,412,109 A | 5/1995 | Takaya et al. |
| 5,475,144 A | 12/1995 | Watson et al. |
| 5,488,143 A | 1/1996 | Uhm |
| 5,679,870 A | 10/1997 | Tustin et al. |
| 5,731,456 A | 3/1998 | Tustin et al. |
| 5,817,869 A | 10/1998 | Hinnenkamp et al. |
| 5,917,089 A | 6/1999 | Howard |
| 6,191,323 B1 * | 2/2001 | Nemeth et al. ............... 568/881 |
| 6,232,504 B1 | 5/2001 | Barteau et al. |
| 6,395,935 B1 | 5/2002 | Baurmeister et al. |
| 6,916,951 B2 | 7/2005 | Tustin et al. |
| 7,491,842 B2 | 2/2009 | Smith |
| 8,148,579 B2 | 4/2012 | Bradin |
| 8,344,167 B2 | 1/2013 | Mizuno et al. |
| 2004/0082821 A1 | 4/2004 | Koch |
| 2005/0014977 A1 | 1/2005 | Drent |
| 2006/0258625 A1 | 11/2006 | Smith |
| 2010/0137647 A1 | 6/2010 | Bradin |
| 2012/0123137 A1 | 5/2012 | Allen et al. |

OTHER PUBLICATIONS

M. Renz, Ketonization of Carboxylic acids by Decarboxylation: Mechanism and Scope, Eur. J. Org. Chem. 2005, 979-988.
J. A. Martens, Acid-catalyzed ketonization of mixtures of low carbon number carboxylic acids.., Studies in Surface Science and Catalysis, vol. 78, 1993, pp. 527-534.
C.N. Pillai, Reaction of Carboxylic Acid with Carbonyl Compounds Over Alumina, Journal of Catalysis, 87, 93-97 (1984).
A.D.Jenkins, The Preparation and Dimerization of Methyl Keten, Journal of Chemical Society, (1952) pp. 2563-2568.
M. M. Taqui Kahn, Low Temperature Homologation of Ethanol Catalsed by Ru-EDTA, Journal of Molecular Catalysis, 49 (1989) L69-L71.
Homer Adkins, The Hydrogenation of Acetoacetic Ester and Certain of Its Derivatives Over Nickel, J. Am. Chem. Soc., 1930, 52 (12), pp. 5192-5198.
Homer Adkins, The Rate of Hydrogenation of Acetoacetic Ester, Dehydroacetic Acid, Benzene, Phenol and Aniline Over Nickel at Pressures From 27 to 350 Atmospheres, J. Am. Chem.
A. B. Steele, A Study of the Polymerization Products of Diketene, J. Org. Chem., 1949, 14 (3), pp. 460-469.
F. Arndt, Dehydroacetic acid, Organic Synthesis, Coll. vol. 3, p. 231 (1955).
J.W. Williams, Ketene Dimer, Coll. vol. 3, p. 508.
Christoph Taeschler, Ketenes, Ketene Dimers, and Related Substances (2000).
W.E.Hanford, Preparation of Ketene and Ketene Dimers, Organic Reactions 1946, Chapter 3, pp. 108.
Polymerization and Thermal Decomposition of Ketene, Arthur. T. Williamson, J. Am. Chem. Soc., 1934, 56 (11), pp. 2216-2218.
J. Hagemeyer Jr., Reactions of Ketene, Industrial and Engineering Chemistry, vol. 41, No. 4, pp. 765.

\* cited by examiner

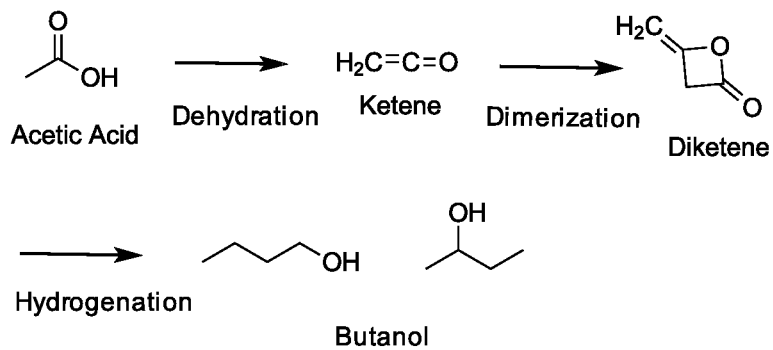
Fig. 1: Synthesis of butanol from acetic acid via diketene.
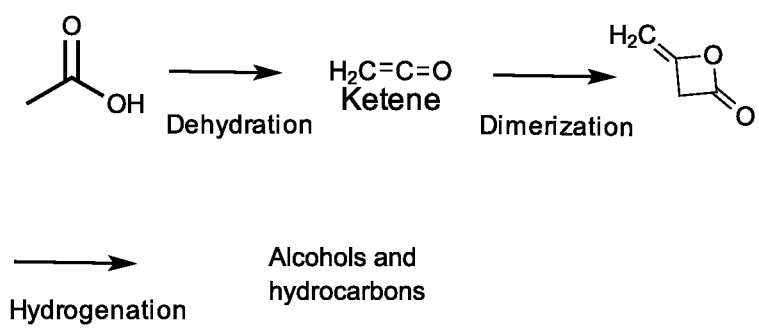
Fig 2: Synthesis of alcohols and hydrocarbons from acetic acid via diketene.
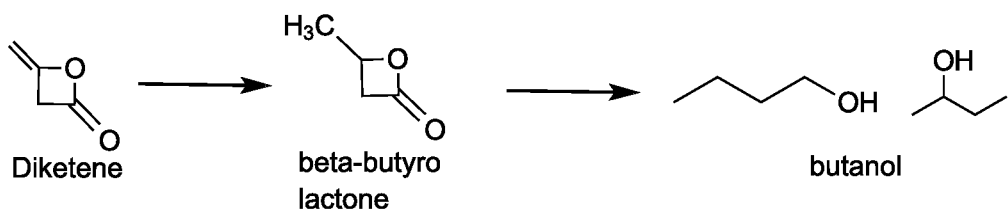
Fig. 3: Synthesis of butanol from diketene via a beta-butyrolactone intermediate.

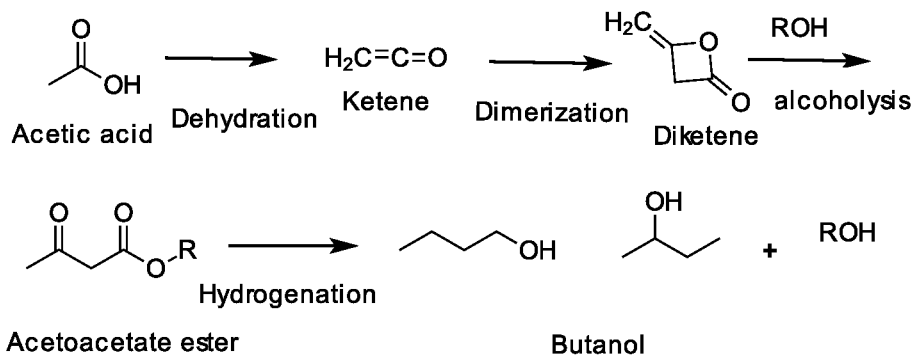
Fig. 4: Synthesis of butanol from acetic acid via a acetoacetate ester intermediate.
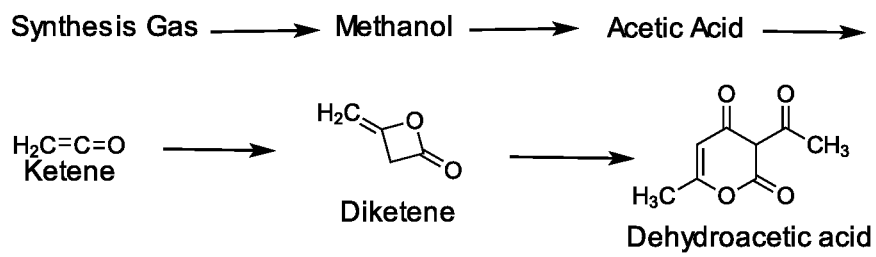
Fig. 5: Synthesis of dehydroacetic acid from synthesis gas.
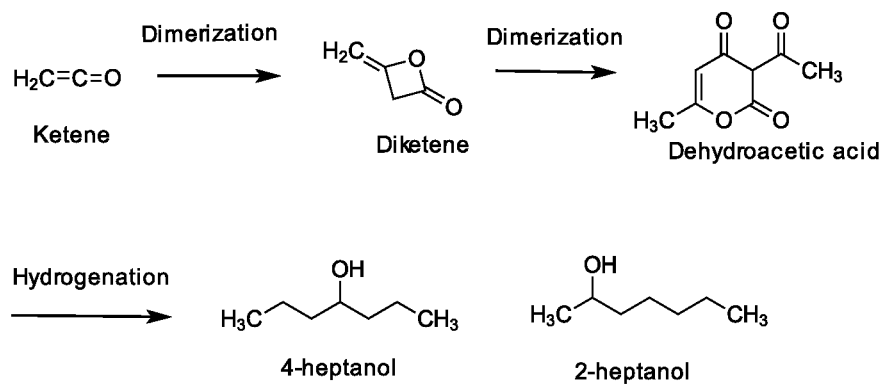
Fig. 6: Synthesis of a seven carbon alcohol from ketene via dehydroacetic acid (DHAA).

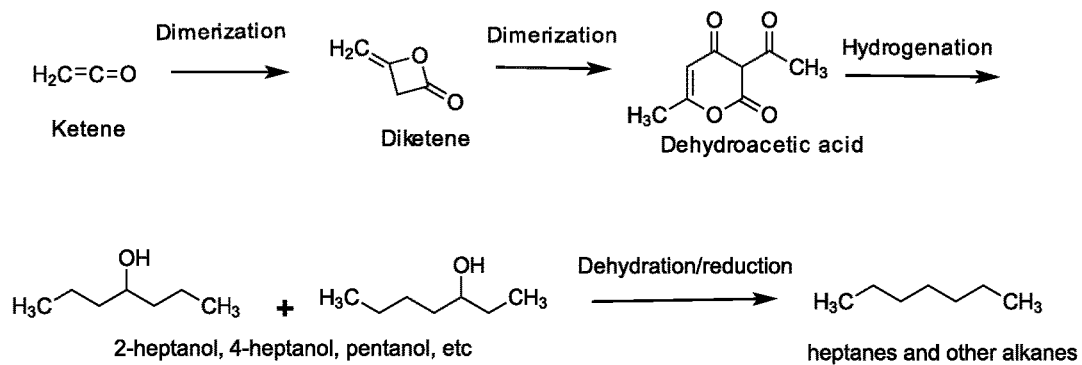
Fig. 7: Synthesis of hydrocarbons and alcohols from ketene via DHAA.
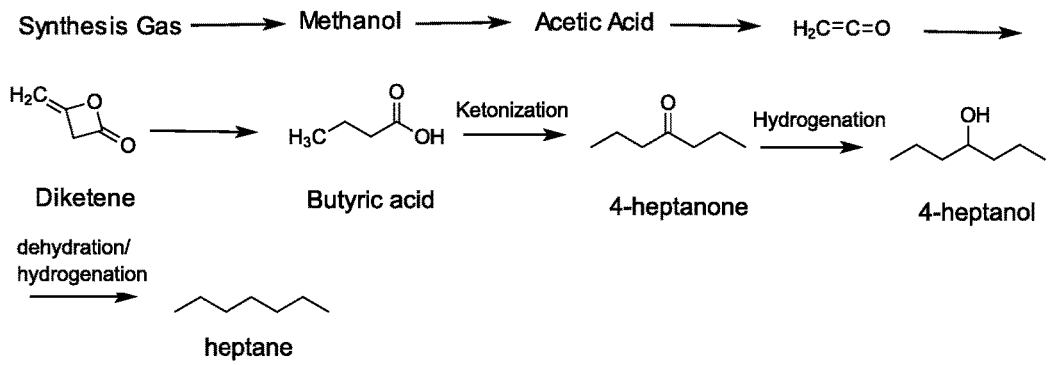
Fig. 8: Synthesis of heptanol and heptanes via ketonization of butyric acid formed by reduction of diketene.

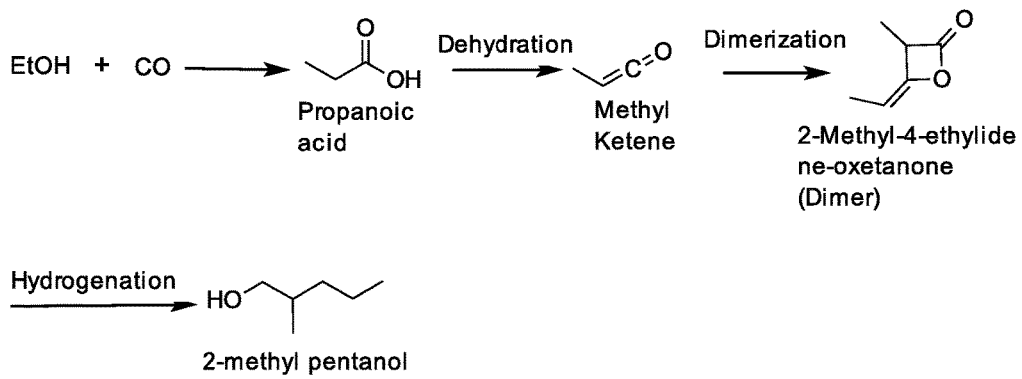
Fig. 9: Synthesis of 2-methyl pentanol from ethanol
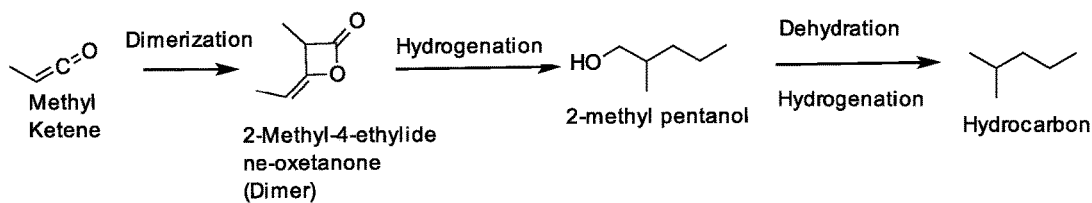
Fig. 10: Synthesis of hydrocarbons from methyl ketene.
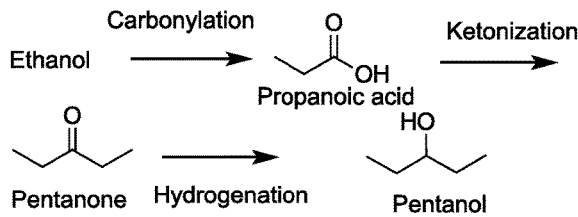
Fig. 11: Synthesis of pentanol from ethanol.

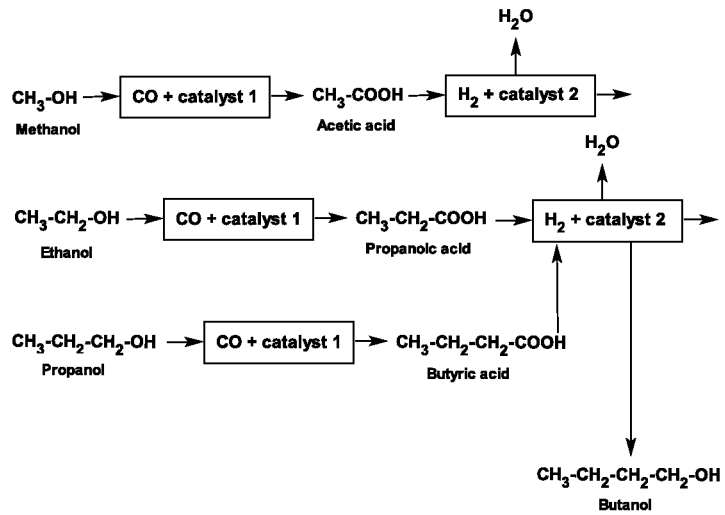
Fig. 12: Synthesis of a butanol-propanol fuel from ethanol or methanol.
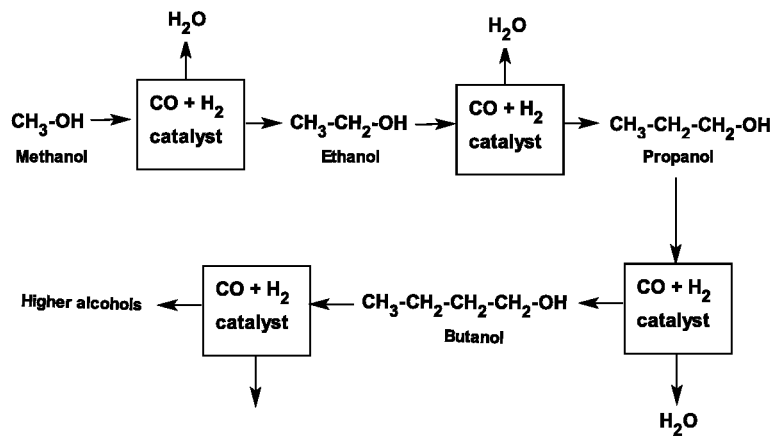
Fig. 13: Synthesis of higher alcohols from methanol via reductive carbonylation.

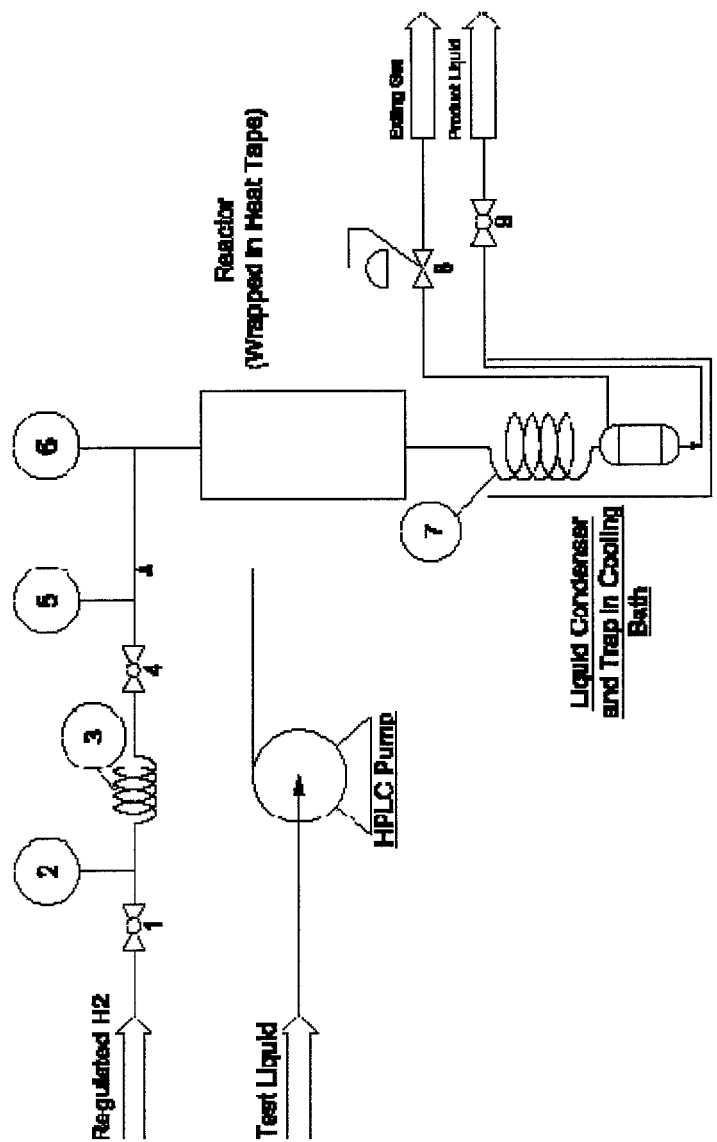
Fig. 14. Hydrogenation reactor system.

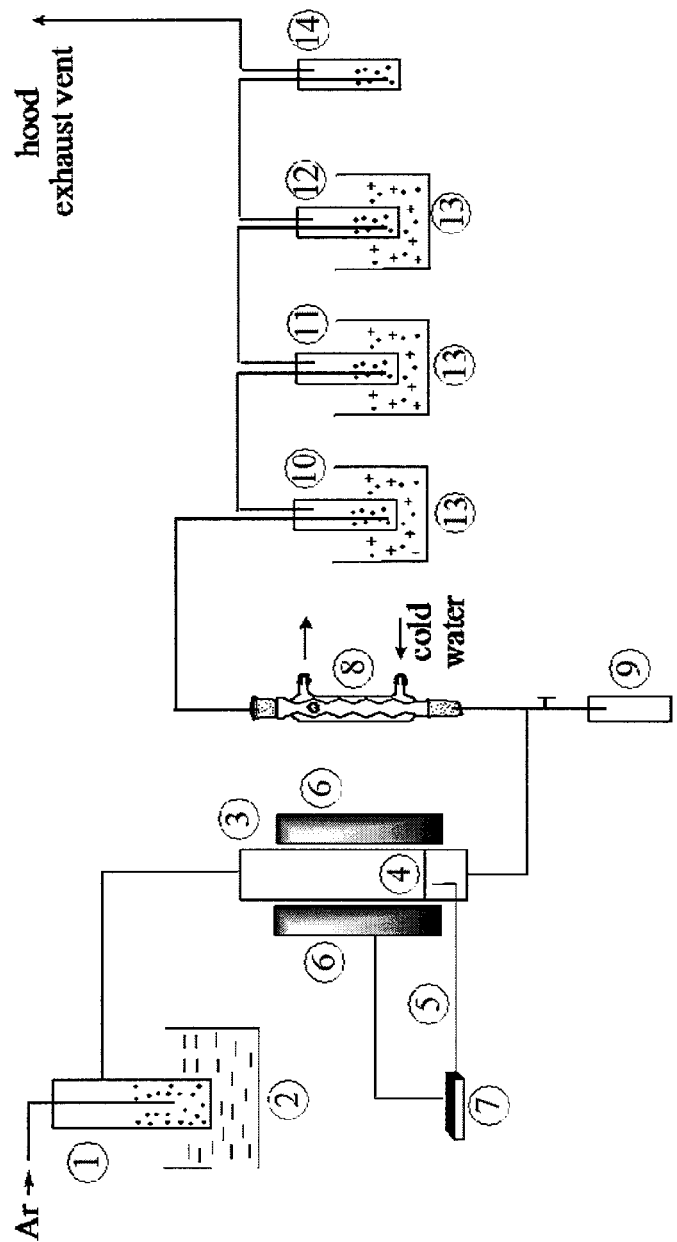
Fig. 15 Apparatus for lab scale synthesis of diketene.

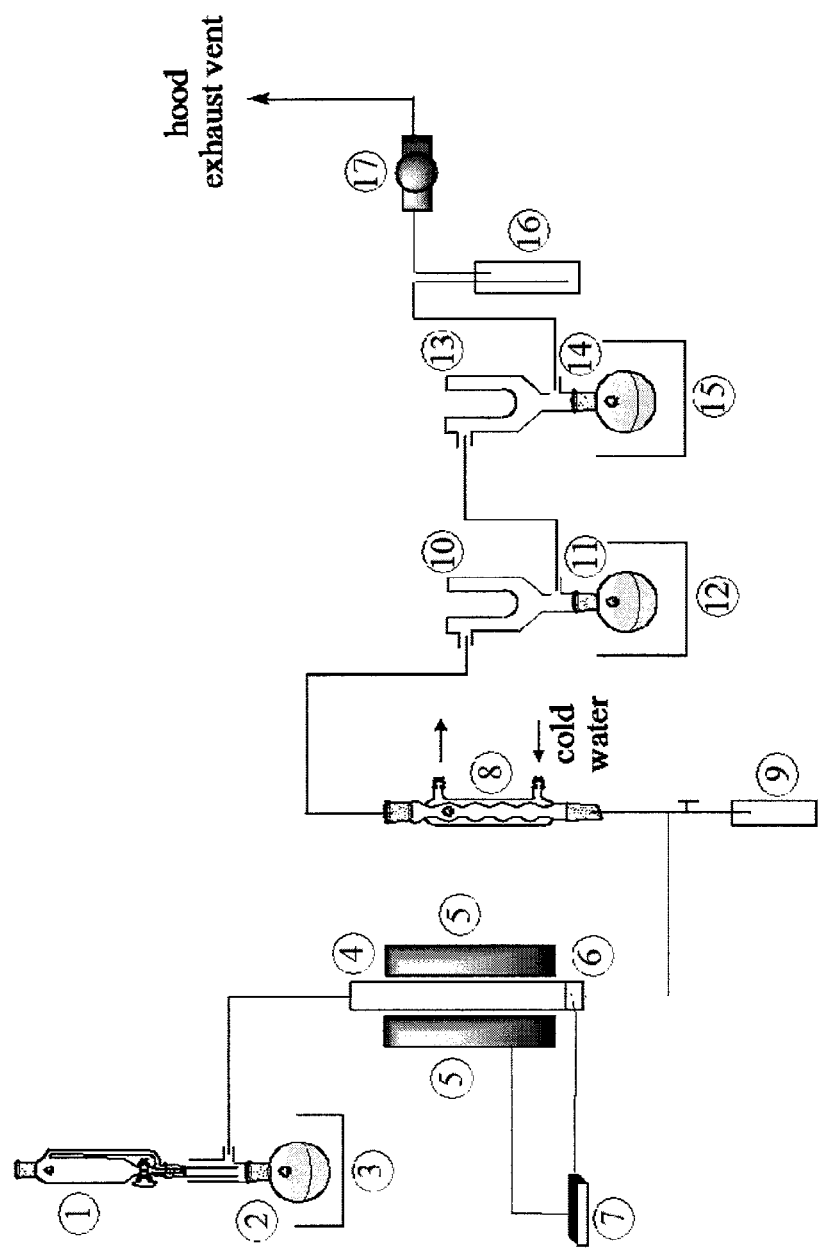
Fig. 16 Apparatus for lab scale synthesis of methylketene dimer.

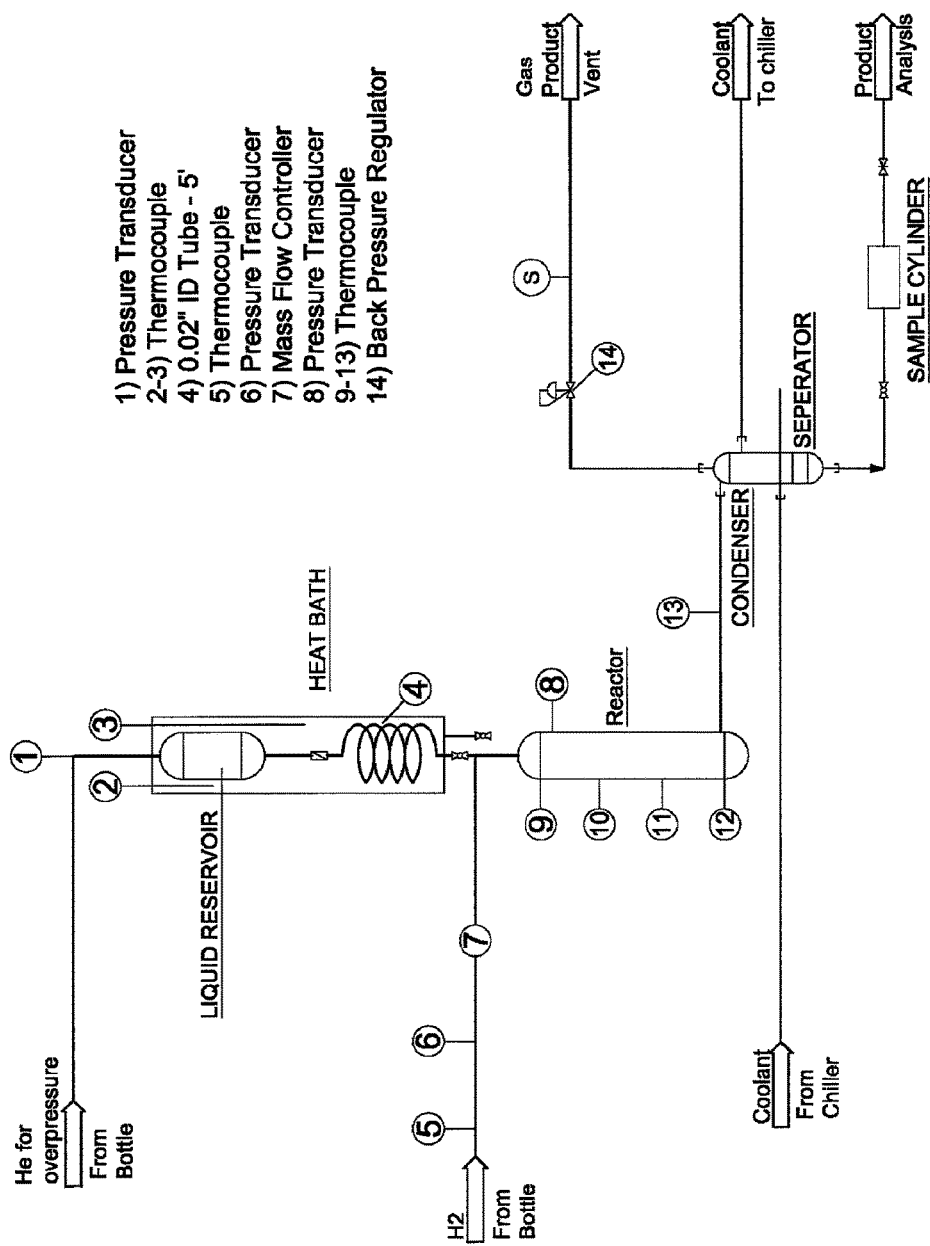
Fig. 17 Reactor system for hydrogenation of

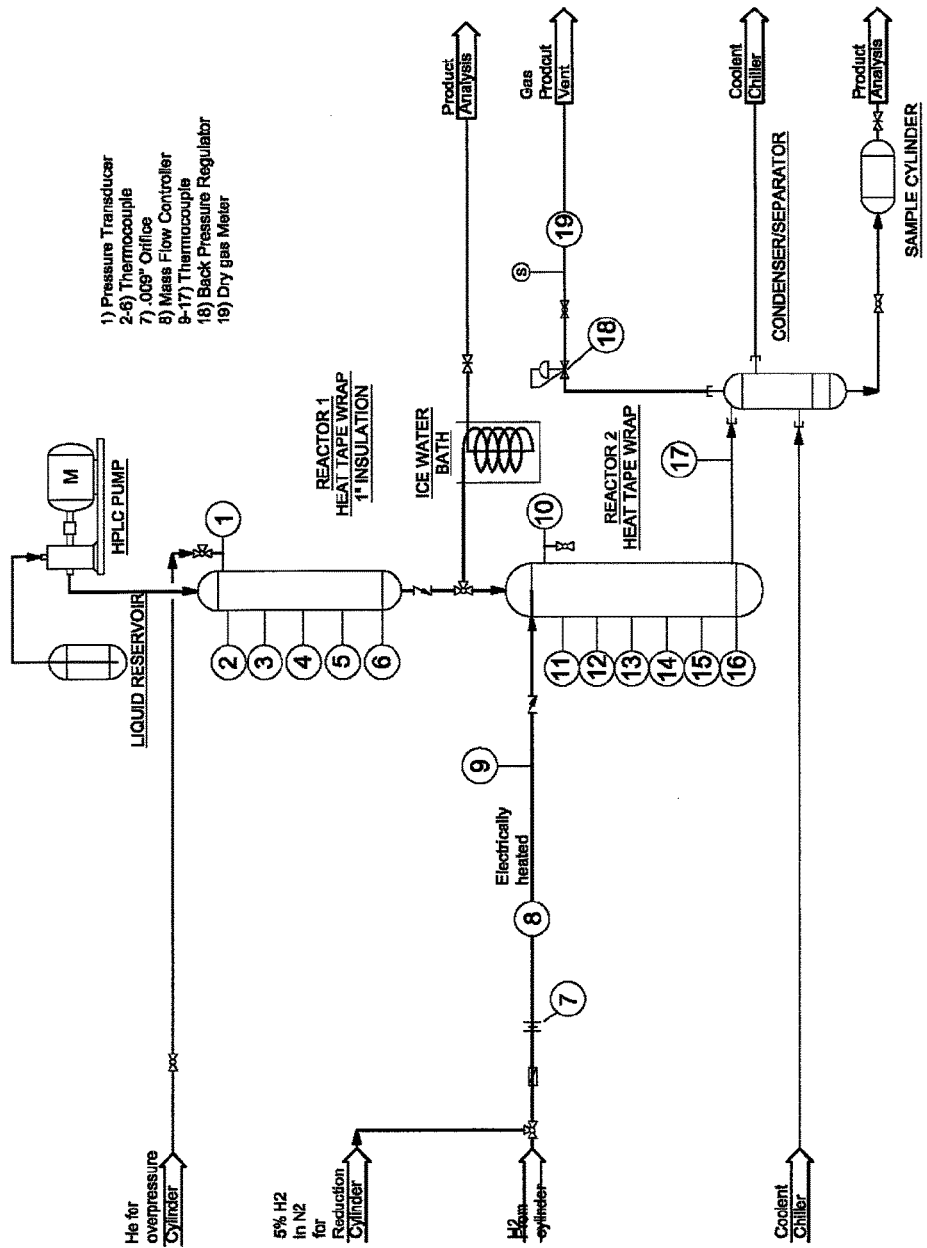
Fig. 18 Reactor system for ketonization and hydrogenation

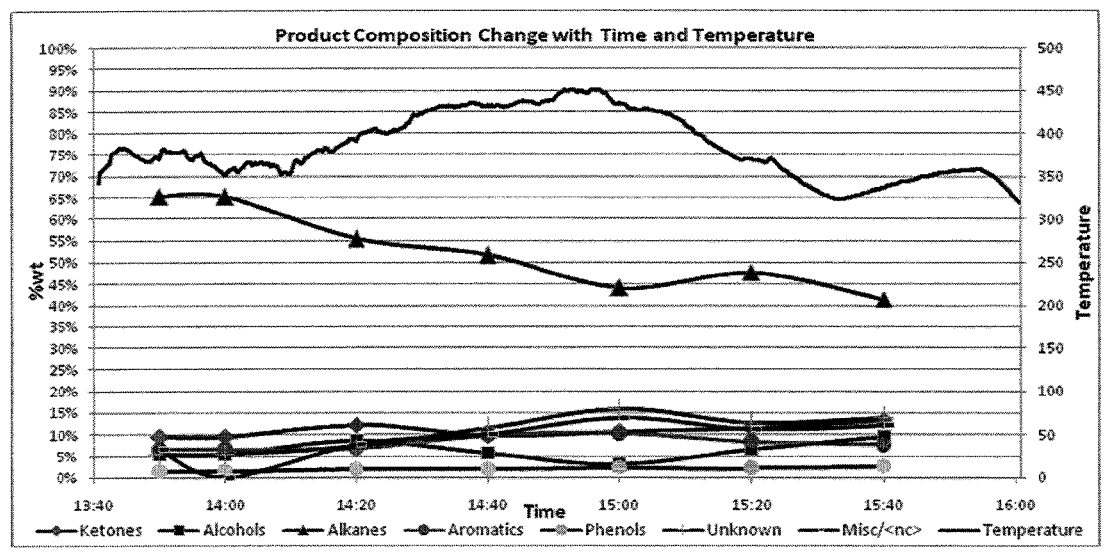
Figure 19: Graph 1. Product composition change with time and temperature in Run 11 DHAA hydrogenation.

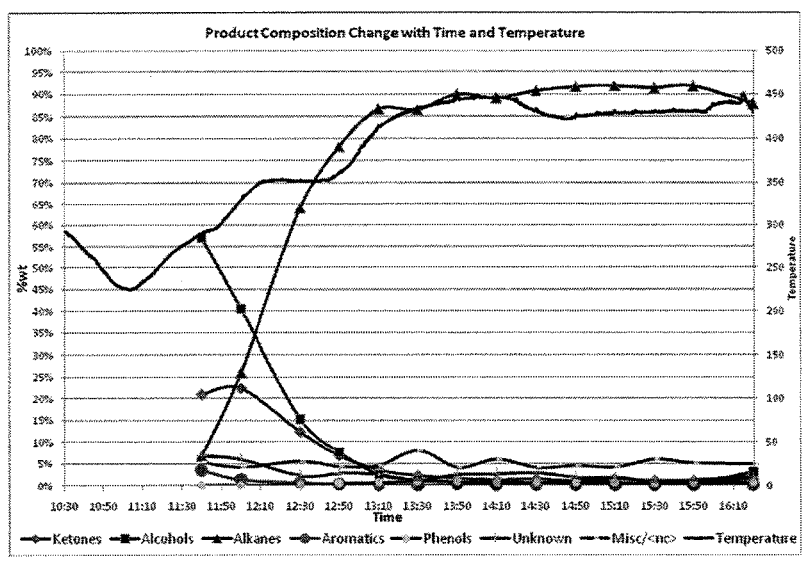
Figure 20. Graph 2 Distribution of products over time as temperature is varied for butyric acid ketonization-hydrogenation run 3.

SYNTHESIS OF HIGH CALORIC FUELS AND CHEMICALS VIA KETENE AND DIKETENE INTERMEDIATES

RELATED APPLICATIONS

This application claims the benefit of U.S. Provisional Application No. 61/558,321 filed Nov. 10, 2011 entitled "Synthesis of Higher Alcohols", U.S. Provisional Application No. 61/577,903 filed Dec. 20, 2011 entitled "Higher Calorific Alcohol and Alkane Fuels and Industrial Chemicals", U.S. Provisional Application No. 61/614,937 filed Mar. 23, 2012 entitled "Synthesis of Hydrocarbon and Oxygenated Fuels and Chemicals", U.S. Provisional Application No. 61/643,447 filed May 7, 2012 entitled "Selective Syngas Conversion to Butanol" and U.S. Provisional Application No. 61/667,093 filed Jul. 2, 2012, entitled "Synthesis of C5 and C6 Fuels and Chemicals", all of which are incorporated herein by reference.

BACKGROUND OF THE INVENTION

Petroleum is a vital source of fuels for transportation, industrial chemicals that produce polymers, plastics, pharmaceuticals, paints and other important chemicals. However, due to economic, environmental and political factors, new sources besides petroleum are being sought for the production of these materials.

Technologies to manufacture industrial commodities such as methanol are mature and used to produce the world's supply from synthesis gas that comes from methane, coal, etc. Ethanol is produced by fermentation and hydration of ethylene produced from petroleum. Technology to produce ethanol from cellulose is still in development. Efforts have been made to develop a synthesis of ethanol from synthesis gas but no satisfactory technologies have materialized yet. There has been increased use of ethanol as a fuel additive and also as an automotive fuel itself. Ethanol does not have a high heat of combustion (30 MJ/kg ethanol vs 45 MJ/kg gasoline) thus yielding significantly lower mileage than gasoline. Another issue with ethanol is the difficulty of ethanol transport by pipeline due to its corrosivity.

Various efforts are underway to find economic fermentation processes to produce butanol which is also an important fuel alternative and industrial chemical. However the economy of these processes due to the time required for each fermentation cycle, environmental problems from large amounts of water consumption for these processes and difficulty of isolation of butanol from broths along with its toxicity to microbes are challenges that have not been overcome.

The present invention avoids these issues and is a novel method to synthesize fuels and chemicals from non-petroleum sources such as biomass, coal and natural gas. The synthetic manufacture of fuels and chemicals, for example alcohols and alkanes with four or more carbons, offers the potential for higher energy fuels that are readily compatible with existing automotive and transportation infrastructure.

BRIEF DESCRIPTION OF DRAWINGS

FIG. 1 shows a representative method for the synthesis of butanol from acetic acid via diketene.

FIG. 2 shows a representative method for the synthesis of higher alcohols and hydrocarbons from acetic acid via a diketene.

FIG. 3 shows a representative method for the synthesis of butanol from diketene via a beta-butyrolactone intermediate.

FIG. 4 shows a representative method for the synthesis of butanols from acetic acid via an acetoacetate ester intermediate.

FIG. 5 shows a representative method for the synthesis of dehydroacetic acid from synthesis gas.

FIG. 6 shows a representative method for the synthesis of seven carbon alcohol from ketene via dehydroacetic acid.

FIG. 7 shows a representative method for the synthesis of alcohols and hydrocarbons from ketene via dehydroacetic acid.

FIG. 8 shows a representative method for the synthesis of heptanol and heptanes via ketonization of butyric acid formed by reduction of diketene.

FIG. 9 shows a representative method for the synthesis 2-methyl pentanol from ethanol.

FIG. 10 shows a representative method for the synthesis of hydrocarbons from methyl ketene.

FIG. 11 shows a representative method for the synthesis of pentanol from ethanol.

FIG. 12 shows a representative method for the synthesis of butanol-propanol fuel from ethanol or methanol.

FIG. 13 shows a representative method for the synthesis of higher alcohols from methanol via reductive carbonylation.

FIG. 14 shows a representative hydrogenation reactor system.

FIG. 15 shows a representative reactor system for lab scale synthesis of diketene.

FIG. 16 shows a representative reactor system for lab scale synthesis of dimer of methyl ketene.

FIG. 17 is a representative description of a reactor system used for hydrogenation of dehydroacetic acid.

FIG. 18 is a representative description of a reactor system used for ketonization and hydrogenation reaction steps.

FIG. 19, Graph 1, is a representative graph of the product composition change with time and temperature in Run 11 DHAA hydrogenation.

FIG. 20, Graph 2, is a representative graph of the distribution of products over time as temperature is varied for butyric acid ketonization-hydrogenation run 3.

DETAILED DESCRIPTION OF THE INVENTION

In one embodiment of the present application, there is provided a process of using a ketene to form a diketene which is then reduced by hydrogen to form alcohol and hydrocarbon fuel and chemical raw materials. In one aspect, an acid, such as a two carbon acetic acid, is converted to a ketene which is dimerized and reduced to products with four or more carbons such as butanol, heptanol and other alcohols. The alcohols produced include compounds, such as alcohols, with three to nine carbons including butanol and its isomers, pentanol and its isomers, hexanol and its isomers, heptanol and its isomers, etc may be used as fuels which have a calorific values closer to gasoline.

In another embodiment, there is provided a process of using syngas as a feedstock to produce diketene which is then selectively hydrogenated to butanol via intermediate beta-butyrolactone. Ketene may be prepared from methanol, which may be carbonylated to form acetic acid and dehydrated to form ketene. In another aspect, the process provides diketene which is then selectively hydrogenated to butanol via an intermediate acetoacetate ester such as methyl acetoacetate. Diketene is readily produced from acetic acid by dimerization of ketene, ketene is produced by pyrolysis of acetic acid and acetic acid is manufactured from syngas via carbonylation of methanol. The alcohol products produced, such as 2-butanol and 1-butanol and heptanols have a calorific value closer to gasoline than ethanol. The 1-butanol and 2-butanol product of the present invention may be used individually or as mixtures.

Also disclosed is a process for converting ketene to diketene, converting diketene to dehydroacetic acid (3-acetyl-2-hydroxy-6-methyl-4H-pyran-4-one, "DHAA") and reduction of DHAA to heptanols, heptanones or heptanes and other useful higher alcohols and alkanes. Diketene is prepared from acetic acid which can in turn be synthesized by the carbonylation of methanol or the oxidation of ethanol. The alcohols produced, such as 4-heptanol and some of its isomers and other products such as pentanol and its isomers, hexanol and its isomers, butanol and its isomers, heptanes and other alkanes, etc which may be used as fuels, have significantly higher calorific values close to gasoline and higher than ethanol and butanol fuel.

Another aspect, there is provided a process to convert two carbon acetic acid to seven carbon products like heptane, heptanone and heptanol using ketene, ketonization and hydrogenation chemistry. Synthesis gas is converted to acetic acid which is dehydrated to form ketene which is dimerized to form diketene. Diketene is converted to butyric acid which is ketonized to form 4-heptanone. 4-Heptanone may be reduced to 4-heptanol or heptanes and other useful higher alcohols and alkanes. The resulting products, such as 4-heptanol, heptane, etc. . . . which may be used as fuels, have significantly higher calorific values close to gasoline and higher than ethanol and butanol fuel. In another aspect, the heptanol prepared according to the processes are highly selective, and produces at least 60%, 65% or 80% heptanol. The products comprising mixtures of four or more carbon alcohols and alkanes are much more amenable to transport through existing pipeline structures.

Yet another aspect of the present invention is a process to convert ethanol to $C_{5-6}$ alcohols, including 3-pentanol and 2-methylpentanol. In one embodiment ethanol is carbonylated to form propanoic acid which is dehydrated to form methyl ketene, methyl ketene is dimerized to form 2-methyl-4-ethylidene-oxetanone which is hydrogenated to form 2-methyl pentanol. In one embodiment, ethanol is carbonylated to form propanoic acid, propanoic acid is ketonized to form 3-pentanone and 3-pentanone is reduced to form 3-pentanol. In one aspect of the method, the fuel composition is blended with an automotive fuel.

In each of the product or product mixtures prepared according to the above processes, the products may also be used as solvents and chemicals in industry. In addition, the products may be blended with fuels such as gasoline, diesel or like fossil fuels or with a biofuel or synthetic fuels, and combinations thereof.

DEFINITIONS

Unless specifically noted otherwise herein, the definitions of the terms used are standard definitions used in the art. Exemplary embodiments, aspects and variations are illustrated in the figures and drawings, and it is intended that the embodiments, aspects and variations, and the figures and drawings disclosed herein are to be considered illustrative and not limiting.

As used herein, an "alkyl" group is a straight, branched, cyclic, acylic, saturated or unsaturated, aliphatic group or alcoholic group having a chain of carbon atoms. A $C_1$-$C_{20}$ alkyl or $C_1$-$C_{20}$ alkanol, for example, may include alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —$(CR^1R^2)_m$— group where $R^1$ and $R^2$ are independently hydrogen or are independently absent, and for example, m is 1 to 8, and such representation is also intended to cover both saturated and unsaturated alkyl groups.

An "alkyl compound(s)" as used herein, is an alkyl containing 1 to 20 carbons ($C_1$-$C_{20}$ alkyl), and includes cyclic and acyclic alkanes, alkenes, alcohols, ketones and aromatics (e.g., benzene, toluene, ethyl benzene etc.) and mixtures thereof. The alkyl compound may be used as a raw material for chemical processing, a solvent or the alkyl compound may be used as a fuel or mixtures of fuels. Such fuel or mixtures of fuels may be further combined with other fuel or fuel products to form a gasoline. Non-exclusive examples of an alkyl compound include butane, 1-butanol, 2-butanol, 2-pentanol, 1-hexanol, 2-hexanol, 2-heptanol, 4-heptanol, 4-heptanone, 3-methyl cyclohexanol, 2,6-dimethyl-4-heptanol and mixtures thereof. Alkyl compounds of the present application exclude saturated beta-lactones.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partially saturated or aromatic.

An alkanol or an alcohol is a compound with an alkyl or cyclic alkyl group bearing a hydroxyl group. Examples of alcohols are methanol, ethanol, propanol, isopropanol, butanol (including 1-butanol, 2-butanol, isobutanol, tert-butanol), pentanol (and its isomers including 1-pentanol, 2-pentanol, 3-pentanol, isopentanol, neopentanol, cyclopentanol, etc) and straight chain, branched and cyclic isomers of other higher alcohols such as hexanol, cyclohexanol, methylcyclohexanol, heptanol (including 1-heptanol, 2-heptanol, 3-heptanol, 4-heptanol, iso-heptanol and other isomers), nonanol, etc. A higher alcohol is an alcohol having two or more carbons.

"Gasoline" is known to comprise of a complex mixture of volatile hydrocarbons suitable for use as a fuel in a spark-ignition internal combustion engine. Typically, gasoline boils over a range of about 27° C. to about 225° C. Gasoline may consist of a single blendstock, such as the product from a refinery alkylation unit, or it may comprise of a blend of several blendstocks. The blending of gasoline is well known in the art and may include a combination of three to twelve or more different blendstocks. Optimization of the blending process takes into account a plurality of characteristics of both the blendstocks and the resulting gasoline, and may include such characteristics as cost and various measurements of volatility, octane, boiling point characteristics and chemical composition. While hydrocarbons usually represent a major component of gasoline, certain oxygen containing organic compounds may be included as gasoline components. In one aspect, such oxygen containing organic compounds are referred to as "oxygenate" or "oxygenates," and are important gasoline substitutes such as ethanol and butanol. Oxygenates are also useful as components in gasoline because they are usually of high octane and can be a more economical source of gasoline octane than a high octane hydrocarbon blending component such as alkylate or reformate. Oxygenates that may be used as gasoline blending agents include, but are not limited to, methanol, ethanol, tertiary-butyl alcohol, methyl tertiary-butyl ether, ethyl tertiary-butyl ether and methyl tertiary-amyl ether. Various catalysts may be used in reduction or hydrogenation reactions of the present application. The catalyst used may contain one or more transition metal such as ruthenium, palladium, platinum, rhodium, nickel, iridium, rhenium, copper, zinc, chromium, nickel, iron, cobalt or combinations of thereof. The catalyst may contain a combination of one or more transition metals with main group elements such as for example platinum and tin or ruthenium and tin. The catalyst may contain promoters such as barium hydroxide, magnesium hydroxide, etc. Reduction or hydrogenation may also be done using Raney type sponge catalysts such as Raney nickel, copper, cobalt, etc optionally bearing promoters such as iron, molybdenum, chromium, palladium, etc.

Catalysts used in reductions may be supported or unsupported. A supported catalyst is one in which the active metal or metals are deposited on a support material; e.g. prepared by soaking or wetting the support material with a metal solution, spraying or physical mixing followed by drying, calcination and finally reduction with hydrogen if necessary to produce the active catalyst. Catalyst support materials used frequently are porous solids with high surface areas such as silica, alumina, titania, magnesia, carbon, zirconia, zeolites etc.

The methods of the present invention can comprise, consist of, or consist essentially of the essential elements and limitations of the method described herein, as well as any additional or optional ingredients, components, or limitations described herein or otherwise useful in synthetic organic chemistry.

"Synthesis gas" or "syngas" is a mixture of varying amounts of carbon monoxide and hydrogen. Syngas maybe produced by the partial oxidation of materials such as methane, liquid hydrocarbons, coal, biomass, etc.

"Biomass" is material obtained from living or recently living organisms.

Acetic acid may be made by oxidation of ethanol produced by fermentation or conversion of synthesis gas to methanol followed by its carbonylation. Synthesis gas may be obtained in large quantities from biomass, coal, natural gas, etc.

In one embodiment acetic acid used in the invention is made from syngas. Syngas may be made from coal, natural gas or like fossil fuel. In another embodiment the acetic acid used in the invention is synthesized from syngas made from a renewable source such as biomass from corncobs, switchgrass, wood chips, recyclable materials like agricultural waste, land fill materials, industrial waste, municipal solid waste, sewage and the like.

Ketene maybe synthesized by various methods described in literature such as dehydration of acetic acid, pyrolysis of acetone or acetic anhydride, etc. In one embodiment ketene is synthesized from acetone. In another embodiment ketene is synthesized from acetic acid. In one embodiment, the ketene produced is dimerized to produce diketene which can be used directly in reduction steps or stored before reduction.

In various embodiments, there is provided methods to prepare alcohols from ketene and diketene. Ketene is dimerized to form diketene which is reduced to produce alcohols and carbon compounds such as hydrocarbons which can be used as fuels and chemicals for industry. In another embodiment diketene is hydrogenated to form a four carbon alcohol. In one embodiment, the product of hydrogenation is a mixture of 2-butanol and 1-butanol. In another embodiment, the hydrogenation product of diketene reduction is a mixture of alcohols including isomers of butanols, pentanols, hexanols, heptanol and higher and lower alcohols. These products may be used as a fuel directly or after purification.

Products such as butyric acid seen in the products of the invention (see Table 5a below) have lower calorific values than alcohols and hydrocarbons but are highly useful for conversion to seven carbon heptanol and heptanes and other high energy fuels and useful chemicals by ketonization and hydrogenation reactions.

In other embodiments, there is provided methods for preparing alcohols from ketene and diketene via beta-butyrolactone (BBL). Ketene is dimerized to form diketene, diketene is hydrogenated to form BBL which is hydrogenated to form butanols. In one embodiment, diketene is hydrogenated to form BBL which is hydrogenated to form butyric acid or a mixture of butanols, butyric acid and its esters. In one embodiment, diketene is hydrogenated to form a mixture of higher alcohols including three carbon and higher alcohols. In a variation of this embodiment, diketene is hydrogenated to form a mixture of higher alcohols and alkanes. In another embodiment diketene is reacted with an alcohol to form an acetoacetate ester which is hydrogenated to form butanol. In one embodiment diketene is converted to methyl acetoacetate and reduced to form a butanol based product such as a mixture of 2-butanol and 1-butanol along with methanol. In one embodiment diketene is converted to butyl acetoacetate by reaction of butanol and diketene and reduced to form a butanol based product such as a mixture of 2-butanol and 1-butanol. In one embodiment diketene is converted to methyl acetoacetate and reduced in situ to form a butanol based product such as a mixture of 2-butanol, 1-butanol and methanol.

In one embodiment diketene is converted to butyl acetoacetate by reaction of butanol and diketene and reduced in situ to form a butanol based product such as a mixture of 2-butanol and 1-butanol. BBL may be made by the reduction of diketene, by oxidation and carbonylation of propylene or by reaction of acetaldehyde with ketene. In one embodiment the reduction of diketene to BBL and then to butyric acid is done with Raney nickel.

In one embodiment the reduction of diketene to BBL and then to butanol is done with a Copper Zinc catalyst commercially available from Johnson Matthey called the CZ29/2T catalyst. In one embodiment the reduction of diketene to BBL and then to butanol is done with Ni/alumina catalyst. In one embodiment, the reduction of the diketene is done at a temperature between 50 and 350° C. in the presence of a catalyst. In one embodiment the reduction of diketene is done with a copper zinc catalyst commercially available from Johnson Matthey called the CZ29/2T catalyst. Hydrogen pressures required for reduction of diketene maybe from 10 psi to 1600 psi. In one embodiment the reduction of diketene is done at a pressure range of 200 to 500 psi.

In one embodiment the reduction of BBL to butanols is done with a Copper Zinc catalyst commercially available from Johnson Matthey called the CZ29/2T catalyst. In another aspect, the reduction BBL to butanols is done with Ni/alumina catalyst. In another aspect, the reduction of BBL is done at a temperature between 50 and 350° C. in the presence of a catalyst. Hydrogen pressures required for reduction of BBL maybe from 10 psi to 1600 psi. In one embodiment the reduction of BBL is done at a pressure range of 200 to 500 psi or more preferably 300 to 500 psi.

In one embodiment, the ketene produced is dimerized to produce diketene which can be converted to dehydroacetic acid (DHAA) in situ and hydrogenated to form higher alcohols and hydrocarbons. In one variation, methanol is used as a source of hydrogen using a copper based catalyst, such as a copper chromite based catalyst. In another aspect, diketene is converted to DHAA in a separate process step which is then reduced to form a heptanol product, which may be purified to a fuel grade composition. In another aspect, the alcohol mixture product synthesized from diketene starting material is dehydrated to yield a mixture of unsaturated hydrocarbons which is in turn hydrogenated to produce a mixture of hydrocarbons. In another aspect, DHAA is hydrogenated in the presence of a catalyst to form a mixture of alcohols and hydrocarbons. In one aspect of the above, the fuel composition is a mixture of ketones, alcohols and alkanes. In one variation of the above, the relative ratios of the ketones, alcohols and alkanes may be adjusted by varying the temperature of the hydrogenation and/or dehydration reaction. In another aspect of the above, the reduction of 4-heptanone, the dehydration of the 4-heptanol and the reduction to form heptane are all performed over the same catalyst bed.

In another embodiment, the alcohol mixture product synthesized from reduction of DHAA is converted directly in a single process step to hydrocarbons. In one embodiment the reduction of DHAA is done with a copper chromite, barium promoted catalyst ($Cr_2CuO_4$, CuO, BaO, Graphite, $CrO_3$, $Cr_2O_3$). In another aspect, the reduction may be done by a copper zinc catalyst. An example of the later is commercially available from Johnson Matthey called the CZ29/2T catalyst. In another aspect, the hydrogenation of DHAA may be done over a 2% ruthenium on alumina catalyst. In another aspect, the reduction of DHAA is done at a temperature between 50 and 350° C. in the presence of a catalyst. Hydrogen pressures required for reduction of DHAA may be from 10 psi to 1600 psi. In one embodiment, the reduction of DHAA is done at a pressure range of 200 to 500 psi. In another aspect, reduction of DHAA is done at 300 psi hydrogen pressure at 300° C.; or at 300 psi hydrogen pressure at 200° C. In another embodiment DHAA can be hydrogenated to 4-heptanone, mixture of 4-heptanone and 4-heptanol or to 4-heptanol. In one embodiment, alcohols are dehydrated to yield a mixture of unsaturated hydrocarbons using gamma-alumina, ZSM-5 or like agents to form unsaturated hydrocarbon products which are in turn hydrogenated to produce a mixture of hydrocarbons.

In another embodiment, there is provided methods to prepare alcohols, ketones and alkanes. Ketene is dimerized to form diketene which is hydrogenated to form butyric acid. Butyric acid is ketonized to produce 4-heptanone which is reduced to form 4-heptanol which may be further converted to heptane, which can be used individually or as mixtures of compounds as fuels, solvents and chemicals for industry. In another aspect, ketonization provides 4-heptanone with conversion of at least 85%, 95%, 98% or 99%. In another aspect, the hydrogenation of the composition comprising 4-heptanone provides a mixture comprising butanol and 4-heptanol. In one aspect of the above, the hydrogenation of 4-heptanone provides a composition that is rich in 4-heptanol. In another aspect, the hydrogenation catalyst, such as the hydrogenation of 4-heptanone, comprises a transition metal or a mixture of two or more transition metals. In another aspect, the catalyst is a copper chromite barium promoted catalyst, or a copper and zinc based catalyst. In one aspect of the above, the mixture comprising 4-heptanone, 4-heptanol, 3-heptene or isomers thereof and heptanes, or mixtures thereof, may be used as a fuel, or further blended with gasoline to form a blended fuel mixture. In one aspect of the above method, the linear and branched heptanes formed comprise of 1-heptene, 2-heptene, 3-heptene, 3-methyl-3-hexene, 3-methyl-2-hexene, 3-methyl-1-hexene, 3-methyl-4-hexene and mixtures thereof. In another aspect, the zeolite is a ZSM-5 catalyst. In another aspect of the method, the catalyst is a nickel on alumina catalyst. In another aspect of the above method, the reduction or hydrogenation, the dehydration, the hydrogenation and the isomerization steps are performed in a single reactor or reaction vessel using the same catalyst and catalyst bed, or mixture of catalyst and using the same catalyst bed.

In another embodiment butyric acid is ketonized to form a product containing 4-heptanone and some unreacted butyric acid which is hydrogenated to form 4-heptanol and butanol. This product may be used as a fuel, solvent or useful industrial chemical product directly or after purification into useful chemical products. In another aspect, diketene is reduced to form butyric acid which is converted to 4-heptanone. The 4-heptanone is reduced to form 4-heptanol. The 4-heptanol may be dehydrated and reduced to form heptanes. In another aspect, the 4-heptanone is hydrogenated to 4-heptanol, dehydrated to form heptenes and the heptenes reduced to form heptanes in the same reactor using a catalyst and hydrogen.

In another embodiment, butyric acid is synthesized from beta-butyrolactone which is synthesized from other starting materials such as propylene, acetaldehyde and ketene, etc. In one embodiment, butyric acid is synthesized by carbonylation of n-propanol. In another embodiment, butyric acid is synthesized by carbonylation of n-propanol and n-propanol is obtained from the carbonylation and subsequent reduction of the propanoic acid product from ethanol. In one aspect of the above, the alkyl compound is further purified to produce a fuel with a higher caloric value than ethanol.

In one embodiment, 4-heptanone is hydrogenated to 4-heptanol, 4-heptanol converted to heptanes and the heptanes formed isomerized to form a mixture of branched hydrocarbons. In a variation of the embodiment, the branched hydrocarbon rich product is used as a fuel. In another embodiment, the catalyst used in the reduction/dehydration/hydrogenation of 4-heptanone to form heptane is a copper/zinc oxide catalyst.

In one embodiment, alcohols are dehydrated to yield a mixture of unsaturated hydrocarbons which are in turn hydrogenated to produce a mixture of hydrocarbons. In another embodiment, alcohols are dehydrated to yield a mixture of unsaturated hydrocarbons using gamma-alumina, ZSM-5 or like agents to form unsaturated hydrocarbon products which are in turn hydrogenated to produce a mixture of branched hydrocarbons. In another embodiment, alcohols are dehydrated and reduced to form a product that contains straight chain saturated hydrocarbons that are isomerized over a zeolite catalyst to yield a mixture of branched hydrocarbons. In another embodiment, heptanol is dehydrated and reduced to form a product that contains straight chain hydrocarbons such as heptane that are reacted over a zeolite catalyst such as ZSM-5 to yield a mixture of $C_{14}$ hydrocarbons. In one embodiment the reduction of 4-heptanone is done with a copper chromite, barium promoted catalyst (62-64% $Cr_2CuO_4$, 22-24% CuO, 6% BaO, 0-4% Graphite, 1% $CrO_3$, 1% $Cr_2O_3$). In another aspect, the reduction of 4-heptanone may be done by a copper zinc catalyst. An example of the later is commercially available from Johnson Matthey called the CZ29/2T catalyst. Pressures required for reduction of 4-heptanone maybe from 10 psi to 1600 psi. In another aspect, the reduction of 4-heptanone is done at a pressure range of 200 to 500 psi. In another aspect, the reduction of 4-heptanone is done at a temperature between 50 and 350° C. in the presence of a catalyst. In one aspect, the reaction is run at a temperature between 175 and 350° C. In one embodiment, reduction of 4-heptanone is done using hydrogen at 300 psi pressure and 300° C. or at 300 psi and 200° C.

In one embodiment, butyric acid is reacted over a solid catalyst to form 4-heptanone. In a variation, butyric is reacted over gamma-alumina to form 4-heptanone. In another variation, the solid support is doped by a metal oxide. An example of this variation is a gamma-alumina catalyst doped with lanthanum oxide. In other embodiments, butyric acid is reacted over ceria, magnesia, hydrotalcites, zeolites and the like to form 4-heptanone.

In one embodiment 4-heptanone can be converted by means of hydrogenation-dehydration step process over bifunctional Pt/Nb$_2$O$_5$ catalyst to linear heptanes. In another embodiment, 4-heptanol can be dehydrated using a gamma-alumina catalyst to heptene, which can reduced in the presence of palladium catalyst to form hydrocarbons. In one embodiment, branched hydrocarbons can be obtained by dehydration-isomerization of 4-heptanol over a zeolite catalyst. In another embodiment 4-heptanone can be oligomerized in the presence of Amberlyst catalyst to produce a mixture of C$_{14}$ unsaturated compounds which are converted to diesel fuel and jet fuel. In one aspect of the above method, the zeolite is a ZSM-5 catalyst. In another aspect, the above method provides a mixture of linear and branched hydrocarbons.

In one embodiment, 4-heptanol is prepared by synthesizing ketene, dimerizing ketene to form diketene and hydrogenating diketene to produce butyric acid. The butyric acid is ketonized by means of ceria-zirconia catalyst to form 4-heptanone which is reduced to heptanol. In another embodiment, the formed 4-heptanol above may be dehydrated to form a hydrocarbon fuel.

In various embodiments, there is provided methods to prepare C$_5$ and C$_6$ alcohols and other products such as alkanes and ketones. In one embodiment ethanol is carbonylated to form propanoic acid which is dehydrated to form methylketene. Methylketene is dimerized and hydrogenated to form alcohol products. In one aspect, ethanol is converted to 2-methyl pentanol by the use of ketene and hydrogenation chemistry. Ethanol is carbonylated to form propanoic acid, the propanoic acid maybe dehydrated to form methyl ketene which is dimerized to form a methyl ketene dimer. The dimer of methyl ketene is hydrogenated to form 2-methyl pentanol. In another aspect, the alcohol product 2-methyl pentanol is dehydrated to yield a mixture of unsaturated hydrocarbons which are in turn hydrogenated to produce a mixture of hydrocarbons.

In one embodiment, ethanol is carbonylated to form propanoic acid which is ketonized to form 3-pentanone. The 3-pentanone is hydrogenated to form 3-pentanol. In one aspect, ethanol used in the process is manufactured from synthesis gas by carbonylation of methanol and hydrogenation of the resulting acetic acid to form ethanol. In another embodiment, the ethanol used in the process is made from fermentation of sugars, starches or biomass. Ethanol may also be manufactured from a cellulosic feedstock or from a petroleum feedstock.

Pressures required for hydrogenation reactions may be from 10 psia to 1600 psia. In one aspect, the reduction is done at a pressure range of 200 to 500 psi. In another aspect, the reduction is done at a temperature between 50 and 350° C. in the presence of a catalyst. In another aspect, hydrogenation is done using hydrogen at 300 psi pressure and 300° C. or at 300 psi and 200° C. In another embodiment 2-methylpentanol can be dehydrated by means of gamma-alumina catalyst to 2-methyl pentene which is reduced in the presence of a hydrogenation catalyst to form hydrocarbons.

In one embodiment, branched hydrocarbons for use as a gasoline component can be obtained by dehydration step of 2-methyl pentanol over a zeolite catalyst. In one embodiment, a method to synthesize a fuel includes the steps of carbonylation of ethanol to form propionic acid, the propionic acid is dehydrated to form methylketene, methyl ketene is dimerized to form a diketene analog. The diketene analog is further dimerized to form a tetraketene adduct, the tetraketene adduct is reduced to form C$_{11}$ and C$_{12}$ alcohols, the alcohols that can be dehydrated to form a fuel. In one aspect of the above process, the methyl ketene is prepared from propanoic acid. In another aspect, the propanoic acid is prepared by the carbonylation of ethanol. In one aspect of the above process, the ethanol may be obtained by a fermentation process, or by the hydrogenation of acetic acid. In another aspect, the catalyst used for the hydrogenation of (E) and (Z)-4-ethylidene-3-methyloxetan-2-one is a transition metal, or a mixture of two or more transition metals. In another aspect, the catalyst is a copper and zinc based catalyst or a copper chromite barium promoted catalyst. In another aspect of the above method, the method provides C$_{6-7}$ ketones, alcohols, alkanes and mixtures thereof. In another aspect, the ratio of the ketones, alcohols and alkanes may be varied by adjusting the temperatures of the hydrogenation reaction.

In a variation, there is provided a method to prepare a fuel including the steps of carbonylating ethanol to form propanoic acid which is hydrogenated to form propanol and fed into the reaction mixture carbonylating ethanol to form a mixture of propanoic and butyric acids which are reduced to form a fuel mixture of propanol and butanol. In another aspect, ethanol is homologated with carbon monoxide and hydrogen to form propanol, propanol is homologated with carbon monoxide and hydrogen to form butanol by feeding the propanol product from the first step back into the ethanol homologation mixture resulting in a product mixture of propanol and butanol which is used as a fuel. In another embodiment butanol can be obtained by the reductive carbonylation cascade of methanol to ethanol to propanol to butanol.

In one variation, the compounds may be synthesized by the steps outlined in FIG. 1, FIG. 2, FIG. 3, FIG. 4, FIG. 5, FIG. 6, FIG. 7, FIG. 8, FIG. 9, FIG. 10, FIG. 11, FIG. 12 or FIG. 13.

EXPERIMENTAL

The following procedures may be employed for the preparation of the compounds of the present application. The starting materials and reagents used in preparing these compounds are either available from commercial suppliers such as SigmaAldrich, Alfa Aesar, etc or are prepared by methods well known to a person of ordinary skill in the art, following procedures described in such references as *Fieser and Fieser's Reagents for Organic Synthesis*, vols. 1-17, John Wiley and Sons, New York, N.Y., 1991; *Rodd's Chemistry of Carbon Compounds*, vols. 1-5 and supps., Elsevier Science Publishers, 1989; *Organic Reactions*, vols. 1-40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989. Standard organic chemical reactions can be achieved by using a number of different reagents, for example, as described in Larock: *Comprehensive Organic Transformations*, VCH Publishers, New York, 1989.

Samples were analyzed on a Agilent 6890 5973 GCMS system equipped with a JW1 DB624 column with dimensions of 30 m×250µ×1.4µ. The method ran at 1 ml/min flow, with oven temperature at 40° C. for the first two minutes followed by temperature ramp at 10° C./min to a temperature of 240° C. which was held for 10 minutes. The solvent delay was set at 5 minutes. Chemical identities of compounds were confirmed by mass spectroscopic qualitative analysis on GCMS against a NIST 2011 library as well as by comparison of retention time against commercial standards. Analysis of samples with volatile alcohols was done on a Gowmac GC system using a Hayesep Q column with He and nitrogen carrier gases. Column temperature was 180° C., detector temp. was 150° C., injector temperature was 150° C., sample valve temperature was 105° C. detector current was 107 mA and injection volume was 1 microliter. Gas samples were analyzed on Varian Micro-GC instruments. Additionally, some product mixtures were analyzed for presence of lower alcohols by derivatizing the alcohol mixture by dissolving in methylene chloride, adding excess of diisopropylethylamine (DIEA), dimethylamino pyridine (DMAP) and acetyl chloride or acetic anhydride. After standing for 30 minutes the reaction mixture was analyzed by GCMS. An experiment for lower molecular weight alcohol analysis was done as follows: The liquid product (30 µl) of the reaction was dissolved in 1 ml of methylene chloride, DIEA was added with a 10 µl syringe in increments until the medium was basic, 2 mg of DMAP was added followed by acetyl chloride. The solution was allowed to stand for about a half hour until the alcohols were esterified to their acetyl derivatives. The resulting mixture was analyzed on the GCMS giving a mixture with ethyl acetate, isopropyl acetate, butyl acetate and sec-butyl acetate. These values represented the approximate percentages of ethyl, isopropyl, butyl alcohols in a sample.

Some tables below show a theoretical estimate of calorific values of a mixture shown. Analysis used calorific values published in literature available on the NIST website at www.nist.gov. For calorific values of molecules like 2-heptanol and 4-heptanol that were not readily available (an isomer's heat of combustion) like the 1-heptanol isomer's calorific value was used in calculations. The quality of GCMS NIST library matches are listed on the last column of tables. Apparatus used for hydrogenation reactions was fabricated in house using standard pipes and parts and instruments available from companies such as Swagelok, Omega engineering, etc. Glassware was purchased commercially or fabricated.

Diketene is manufactured on an industrial scale by the dehydration of acetic acid to ketene. It can be synthesized from various other starting materials including acetic anhydride, acetone, acetyl halides, etc. Ketene was generated by thermal decomposition of acetone and dimerized to diketene at low temperature. DHAA is manufactured on commercial scale from diketene and is commercially available.

Experiment 1

Synthesis of diketene: The reactor system (FIG. 15) was installed inside of a good working fume hood. The feed stream of acetone vapor was generated by passing argon through a glass bubbler filled up with acetone which was then passed to the top of a vertical hollow quartz tube with length of 47 cm and internal diameter of 22 mm. At the lower part of the quartz tube (5 cm from the bottom) was placed the removable silica foam monolith disk with 45 pores per inch, 20 mm diameter and 0.1 cm thickness. The disk was supported inside of the reactor by a built-in quartz frit and temperature of the disk was measured with an external thermocouple placed in a glass pocket located under the frit. The quartz tube was placed in a cylindrical furnace where the temperature was controlled with a PID controller. The ketene from the quartz tube was passed through a condenser cooled with cold water (bearing a graduated cylinder attached at the bottom receiver for liquid condensate) followed by three cylindrical gas traps connected in series filled with acetone and immersed in a dry ice/acetone baths. At the end of the line was installed the fourth glass trap filled up with acetone kept at room temperature with the outlet tube placed into the hood's exhausting vent.

The bubbler and three glass cylinder traps were charged with 300 ml of dry acetone (99.5%) each and the traps were immersed in a dry ice/acetone bath at a temperature of minus 72° C. The fourth glass trap was charged with 150 ml of acetone at room temperature. The condenser was connected to circulating cold water (8-12° C.) from a separate water/ice bath. The furnace temperature was set to 620° C. and argon was passed through the bubbler with acetone at a flow rate 0.7-1.0 l/min to deliver acetone vapour to the quartz tube reactor. Temperature of acetone in the bubbler was maintained by a water bath at about 40° C. The furnace temperature was kept at range of 620-670° C. to maintain temperature of the silica foam disk in the reactor at 470-510° C. After 4 hours of the continuous passing of acetone stream vapour through the quartz reactor the furnace was turned off and the argon flow was reduced to 0.1 l/min. When the quartz tube reached room temperature the argon flow was stopped and the reactor system including three glass cylinder traps immersed in a dry ice/acetone bath was left to stand overnight. The acetone solutions from the three traps were collected and the solvent was evaporated under vacuum at a temperature range of 25-30° C. The resulting dark red concentrate was distilled under vacuum at 55-70° C. using a cold finger (cooled with acetone/dry ice) and the formed white solid was melted into a separate flask to give a yellowish liquid weighing 16.5 g, including 75% of diketene, 16% of acetic anhydride and 5% of acetic acid. The diketene was taken forward into the next step without further purification.

Reduction of Diketene:

Experiment 2

Reduction of diketene 62 hour (batch reactor): The reduction reaction was performed in a hydrogenation reactor consisting of a ½" diameter stainless steel tube fitted with a ball valve at the bottom and a cross (Swagelok parts) on the top. A thermocouple (top arm), side arms bearing a pressure gauge and pressure relief valve and a ball valve were attached to three arms of the cross and the fourth (bottom) arm was attached to the top of the stainless steel tube. The tube was wrapped with heating rope and insulation was wrapped around the heating rope. The ball valve on the bottom of the reactor is connected to a 3" length of ⅛" tube immersed in a cold water bath is connected to a 1/16" tube bearing a ball valve and needle valve to collect liquid samples from the reactor.

Procedure: 10.5 g of copper/zinc catalyst CZ 29/2T (Johnson Matthey) was weighed and loaded into the hydrogenation reactor. A 5% hydrogen in argon mixture was passed over the catalyst bed at 0.8 lit/min at a temperature of 180° C. for about 18 hours to reduce the catalyst. The heating was shut off and the catalyst allowed to cool. The catalyst was removed from the reactor under an argon atmosphere in a glove bag and placed in a porcelain dish and 0.7 ml of diketene was added dropwise to the catalyst pellets. The wetted catalyst pellets were poured back into the reactor, the reactor was sealed, removed from the glove bag and purged with argon and hydrogen three times each and then hydrogen filled to a pressure of about 1100 psi. Heating was started and temperature of the catalyst bed was about 209° C. The hydrogenation was continued for about 62 hours after which the reactor was cooled and a sample of liquid collected from the reactor bottom. GCMS analysis of the sample showed the formation of higher alcohols including 1-butanol, 2-butanol, 2-pentanol, hexanol isomers, methyl cyclohexanol, heptanol isomers, etc in the reaction. GCMS qualitative analysis of higher alcohols formed is shown in Table 1 also presents a theoretical estimation of the calorific value of a mixture. Besides the major alcohol peaks in the GCMS, peaks were also observed indicating formation of esters, hydrocarbons and other oxygenated carbon compounds.

purged thrice with argon, twice with hydrogen and then filled with hydrogen to 1100 psi. Temperature was raised to 67° C. and allowed to stand for 4 hours. A gas sample was taken for $CO_2$ and CO analysis indicating 2.55% CO and 0.5% $CO_2$. Heating was shut off and the reactor was allowed to stand at room temperature overnight. Next morning, heating was resumed and temperature was raised to 210° C.

TABLE 1

Products in 62 hr diketene reduction with an energy estimation of the mixture.

| Compound | GC Ret. Min. | Area % | Mol. Wt. | Δc liq. kJ/gm | Normlzd Wt. | Wt. Fraction | Δc liq. kJ/Kg | Energy/ comp | NIST Δc liq. kJ/mol |
|---|---|---|---|---|---|---|---|---|---|
| 2-Butanol | 5.6 | 6.5 | 74 | 35.9 | 481 | 7.6 | 35946 | 17290000 | 2660 |
| 1-Butanol | 6.9 | 8.2 | 74 | 36.1 | 606.8 | 9.6 | 36081 | 21894000 | 2670 |
| 2-Pentanol | 7.5 | 15.8 | 88 | 37.8 | 1390.4 | 22.0 | 37841 | 52614000 | 3330 |
| 2-Hexanol | 8.7 | 2.2 | 102 | 39.1 | 224.4 | 3.5 | 39059 | 8764800 | 3984 |
| Hexanol | 11 | 1.37 | 102 | 39.1 | 139.74 | 2.2 | 39059 | 5458080 | 3984 |
| 4-heptanol | 11.2 | 4.4 | 116 | 40.0 | 510.4 | 8.1 | 39974 | 20402800 | 4637 |
| 2-heptanol | 11.5 | 4.3 | 116 | 40.0 | 498.8 | 7.9 | 39974 | 19939100 | 4637 |
| 3-methyl cyclohexano | 12.5 | 17.7 | 116 | 40.0 | 2053.2 | 32.5 | 39974 | 82074900 | 4637 |
| 2,6-dimethyl-4-heptanol | 13.2 | 2.9 | 144 | 41.3 | 417.6 | 6.6 | 41292 | 17243400 | 5946 |
| Total | | | | | 6322.34 | 100.0 | 349200 | 2.46E+08 | |
| Average Energy/Kg of fuel | | | | | | | | 38859.2 | |

Experiment 3

Diketene reduction 1 day: 10 g of copper/zinc catalyst pellets CZ29/2T (Johnson Matthey) was loaded into a stainless steel tube, fixed bed hydrogenation reactor (described above) and reduced overnight in a stream of 5:95 hydrogen: argon at 180° C. After 18 hours the catalyst was cooled to room temperature and poured into a flat porcelain dish in a glove bag under argon. 1 gm of diketene was added dropwise to the catalyst pellets to wet them as evenly as possible. The reactor was resealed, removed from the glovebag, The reaction absorbed hydrogen with pressure dropping from 1200 psi to 940 psi so hydrogen was filled as required to keep pressure in the range of 1045 to 1240 psi. After 4.5 hours of heating at 210° C. a liquid sample was taken by cooling the sampling port with ice water bath and the heating was shut off. GCMS qualitative analysis of higher alcohols formed is shown in Table 2 and also presents a theoretical estimation of the calorific value of a mixture. Mixture of products indicated complete conversion of diketene, 48% by area of higher alcohols formed of which 9.4% were 1-butanol and 2-butanol combined.

TABLE 2

Products in 4.5 hr diketene reduction mixture with an energy estimation of the same.

| Compound | GC Ret. Min. | Area % | Mol. Wt. | Δc liq. kJ/gm | Normlzd Wt. | Wt. Fract. | Δc liq. kJ/Kg | Energy/ comp | NIST Δc liq. kJ/mol |
|---|---|---|---|---|---|---|---|---|---|
| 2-Butanol | 5.6 | 5 | 74 | 35.9 | 370 | 7.6 | 35946 | 13300000 | 2660 |
| 1-Butanol | 6.9 | 4.4 | 74 | 36.1 | 325.6 | 6.6 | 36081 | 11748000 | 2670 |
| 2-Pentanol | 7.5 | 11.9 | 88 | 37.8 | 1047.2 | 21.4 | 37841 | 39627000 | 3330 |
| 2-Hexanol | 8.7 | 3.7 | 102 | 39.1 | 377.4 | 7.7 | 39059 | 14740800 | 3984 |
| Hexanol | 11 | 0.54 | 102 | 39.1 | 55.08 | 1.1 | 39059 | 2151360 | 3984 |
| 4-heptanol | 11.2 | 3.14 | 116 | 40.0 | 364.24 | 7.4 | 39974 | 14560180 | 4637 |
| 2-heptanol | 11.5 | 2.6 | 116 | 40.0 | 301.6 | 6.2 | 39974 | 12056200 | 4637 |
| 3-methyl cyclohexanol | 12.5 | 12.4 | 116 | 40.0 | 1438.4 | 29.4 | 39974 | 57498800 | 4637 |
| 2,6-dimethyl 4-heptanol | 13.2 | 4.3 | 144 | 41.3 | 619.2 | 12.6 | 41292 | 25567800 | 5946 |
| Total | | | | | 4898.72 | 100.0 | 349200 | 191250140 | |
| Average Energy/Kg of fuel | | | | | | | | 39040.8392 | |

Experiment 4

Diketene reduction 30 minutes: 8.44 g of a copper-zinc oxide based catalyst Pricat CZ29/2T (Johnson Matthey) was placed in the hydrogenation reactor and purged with argon thrice followed by a stream of 5% $H_2$/argon at 1 l/min overnight. The temperature of the reactor (catalyst bed) was in the 170 to 210° C. range during the reduction. The 5% hydrogen in argon was replaced by a stream of pure hydrogen at 0.4 l/min at a temperature of 160 to 180° C. for 40 minutes. Heating was stopped and the reactor cooled down with the 5% hydrogen stream. The reactor was placed in a glove bag under argon and catalyst removed and carefully wetted dropwise with 1 ml of diketene. The catalyst wetted with the diketene was then placed back in the reactor and the reactor sealed, removed from the glove bag and purged thrice with argon. Hydrogen pressure was set to 1100 psi and heating was started. The temperature rose rapidly from room temperature to around 188° C. as hydrogen was absorbed by the reaction. Heating was switched off about 30 minutes after temperature was reached. The pressure was between 1180 to 930 psi. The reactor vapors were condensed into a liquid using an ice water bath, collected and sampled on the GCMS. GCMS analysis of the sample showed the formation of higher alcohols including 1-butanol, 2-butanol, 2-pentanol, hexanols, heptanols and methyl cyclohexanol, etc in the reaction. GCMS qualitative analysis of higher alcohols formed is shown in Table 3, also presents a theoretical estimation of the calorific value of a mixture. Besides the major alcohol peaks in the GCMS, peaks were also observed indicating formation of esters, hydrocarbons and other oxygenated carbon compounds. GCMS qualitative analysis of higher alcohols formed is shown in Table 3 and also presents a theoretical estimation of the calorific value of a mixture. Complete conversion of diketene was observed, 44% of higher alcohols of which 1-butanol and 2-butanol were 9%.

a ball valve. The other side arm of the ¼" union cross was connected to a ¹⁄₁₆" tube which was attached to a Gilson 307 HPLC pump. The ¹⁄₁₆" tube entered the reactor and extended down till it was just above the catalyst bed. The bottom arm of the cross was attached to the top of the ½" stainless steel tube. A second thermocouple was installed in the middle section to measure internal temperature. The tube was wrapped with heating rope and insulation was wrapped around the heating rope. A third thermocouple was placed under the heating rope. All three thermocouples were connected to a digital display. The ball valve on the bottom of the reactor is connected to a coil of ⅛" stainless steel tube that was connected to 2" length of ¼ inch tube with a drain at its bottom for liquid condensate and a vent near its top that carried out non-condensing gases. This coiled tube and lower portion were cooled with ice water and served as a trap to collect liquid. The end of the gas vent had a ball valve and the liquid collecting end had a needle valve so that it could be opened slowly to collect liquid samples. The gas outlet of the condenser, including a port for gas sampling was connected to a back pressure gauge that enabled control of reactor pressure which was in turn connected to a flow meter that vented reactor gases to the hood via a tube.

Procedure: 6.5 g of the CuO—ZnO catalyst (Unicat, LS-402, 5×2 mm) was placed in the reactor and covered on top with 1.0 g glass beads. The reactor was purged with nitrogen followed by a stream of 5% $H_2$/nitrogen at 0.4 l/min overnight with temperature of the reactor 190-195° C. and then 5% $H_2$/nitrogen was replaced by a stream of pure hydrogen at 0.4 l/min at 195° C. for 1 h. The reactor was initially heated to 210° C., hydrogen pressure was set up to 300 psi at hydrogen flow rate of 0.3 l/min and HPLC pump was turned on to pump diketene (GC: 95.1% diketene, 3.5% acetic acid, 0.7% acetic anhydride) at a rate of 0.05 ml/min. The experiment was run for 2.3 h at temperature gradient from 210 to 230° C. (catalyst temp at middle of the reactor) and samples of the reaction mixture were collected for GS-MS analysis (in methyl acetate). GC analysis for volatile products on a Gowmac GC against quantitative standards showed samples S3, S5, S8 contained about 31 to 32% isopropanol and about 4% ethanol each by volume. GCMS qualitative analysis of products formed is shown in Table 4, also an estimation of the calorific value of a sample mixture 2 (S2) based on the GCMS chromatogram is shown in Table 4a.

TABLE 3

Products in a 0.5 hr diketene reduction mixture with an energy estimation of the same.

| Compound | GC Ret. Min. | Area Percent | Mol. Wt. | Δc liq. kJ/gm | Normlzd Wt. | Wt. Fract | Δc liq. kJ/Kg | Energy/ comp | NIST Δc liq. kJ/mol |
|---|---|---|---|---|---|---|---|---|---|
| 2-Butanol | 5.6 | 3.8 | 74 | 35.9 | 281.2 | 6.4 | 35946 | 10108000 | 2660 |
| 1-Butanol | 6.9 | 4.8 | 74 | 36.1 | 355.2 | 8.1 | 36081 | 12816000 | 2670 |
| 2-Pentanol | 7.6 | 11.3 | 88 | 37.8 | 994.4 | 22.5 | 37841 | 37629000 | 3330 |
| 2-Hexanol | 8.8 | 0.93 | 102 | 39.1 | 94.86 | 2.2 | 39059 | 3705120 | 3984 |
| Hexanol | 11 | 0.4 | 102 | 39.1 | 40.8 | 0.9 | 39059 | 1593600 | 3984 |
| 4-heptanol | 11.3 | 3.7 | 116 | 40.0 | 429.2 | 9.7 | 39974 | 17156900 | 4637 |
| 2-heptanol | 11.5 | 2.2 | 116 | 40.0 | 255.2 | 5.8 | 39974 | 10201400 | 4637 |
| 3-methyl-cyclohexanol | 12.6 | 16.9 | 116 | 40.0 | 1960.4 | 44.4 | 39974 | 78365300 | 4637 |
| 2,6-Dimethyl-4-heptanol | 13.3 | | 144 | 41.3 | | | 41292 | | 5946 |
| Total | | | | | 4411.26 | 100.0 | 349200 | 171575320 | |
| Average Energy/Kg of fuel | | | | | | | | 38894.8554 | |

Experiment 5

Diketene reductions in continuous flow reactor system on a copper-zinc catalyst: The hydrogenation was performed in a steel tube reactor (see FIG. 14) (made from Swagelok parts, volume 16 ml) consisting of a ½" diameter stainless steel tube fitted with a ball valve at the bottom and a ¼" union stainless steel cross on the top. A thermocouple was attached to the top arm of the cross with one of the (cross) side arms bearing a pressure gauge, pressure relief valve and

TABLE 4

Products seen in a Cu—ZnO diketene hydrogenation GCMS analysis.

| Reactor temp., ° C. | 205 | 217 | 224 | 224 | 209 |
|---|---|---|---|---|---|
| Process time, min | 59 | 79 | 99 | 119 | 139 |
| (sample no.) | (S2) | (S4) | (S6) | (S8) | (S10) |
| (sample weight gms) | (0.33 g) | (0.32 g) | (0.43 g) | (0.40 g) | (0.54 g) |
| | GCMS Area % | | | | |
| 2-Butanone | 1.3 | 1.1 | 1.0 | 0.8 | 0.8 |
| 2-Butanol | 29.5 | 26.7 | 25.1 | 22.3 | 20.7 |
| 1-Butanol | 42.9 | 46.2 | 43.9 | 39.8 | 37.2 |
| 2-Pentanol | 2.1 | 1.8 | 1.7 | 1.8 | 1.7 |
| Diketene | 0.6 | 0.9 | 0.7 | trace | 0.4 |
| Butyric acid i-propyl ester | 2.5 | 2.6 | 9.7 | 5.3 | 5.7 |
| 4-Heptanol | 4.4 | 4.4 | 3.9 | 4.7 | 4.8 |
| 2-Heptanol | 3.1 | 3.0 | 2.6 | 2.8 | 2.7 |
| Butyric acid sec-butyl ester | 0.9 | 0.9 | 1.1 | 1.4 | 1.4 |
| 3-Methyl cyclohexanol | — | 1.3 | 1.5 | 1.8 | 1.7 |
| Butyric acid butyl ester | 2.2 | 2.6 | 3.2 | 4.3 | 4.4 |
| 1-Butanol + 2-Butanol | 72.4 | 72.9 | 69.0 | 62.1 | 57.9 |

Samples showed over 99% of diketene was reacted, included 69-83% higher alcohols, of which 58-73% was 1-butanol and 2-butanol. The product mixture was also observed to contain esters and a ketone which combined with the alcohols was 82-94% of product.

TABLE 4a

Products in Cu—ZnO diketene reduction reaction sample 2 with an energy estimation of the same.

| | | Acids | | | Alcohols | | | Esters | | | Ketones | | | TOTAL | |
|---|---|---|---|---|---|---|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG |
| 1 | 0.00% | | 0.00 | 0.00% | | 0.00 | 0.00% | | 0.00 | 0.00% | | 0.00 | 0.00% | 0.00 |
| 2 | 0.45% | 14.50 | 0.07 | 0.00% | | 0.00 | 0.00% | | 0.00 | 0.00% | | 0.00 | 0.45% | 14.50 |
| 3 | 0.00% | | 0.00 | 0.00% | | 0.00 | 0.00% | | 0.00 | 0.00% | | 0.00 | 0.00% | 0.00 |
| 4 | 0.00% | 0.00 | 0.00 | 68.91% | 35.90 | 24.74 | 0.00% | | 0.00 | 1.84% | 33.90 | 0.62 | 70.75% | 35.85 |
| 5 | 0.00% | | 0.00 | 2.32% | 37.80 | 0.88 | 0.00% | 0.00 | 0.00 | 0.00% | 0.00 | 0.00 | 2.32% | 37.80 |
| 6 | 0.00% | | 0.00 | 2.50% | 39.10 | 0.98 | 0.00% | 0.00 | 0.00 | 0.00% | | 0.00 | 2.50% | 39.10 |
| 7 | 0.00% | | 0.00 | 12.73% | 40.10 | 5.10 | 4.17% | 32.18 | 1.34 | 1.35% | 39.10 | 0.53 | 18.24% | 38.22 |
| 8 | 0.00% | | 0.00 | 0.00% | | 0.00 | 5.74% | 33.60 | 1.93 | 0.00% | | 0.00 | 5.74% | 33.60 |
| 9 | 0.00% | | 0.00 | 0.00% | | 0.00 | 0.00% | | 0.00 | 0.00% | | 0.00 | 0.00% | 0.00 |
| 10 | 0.00% | | 0.00 | 0.00% | | 0.00 | 0.00% | | 0.00 | 0.00% | | 0.00 | 0.00% | 0.00 |
| 11 | 0.00% | | 0.00 | 0.00% | | 0.00 | 0.00% | | 0.00 | 0.00% | | 0.00 | 0.00% | 0.00 |
| 12 | 0.00% | | 0.00 | 0.00% | | 0.00 | 0.00% | | 0.00 | 0.00% | | 0.00 | 0.00% | 0.00 |
| 13 | 0.00% | | 0.00 | 0.00% | | 0.00 | 0.00% | | 0.00 | 0.00% | | 0.00 | 0.00% | 0.00 |
| 14 | 0.00% | | 0.00 | 0.00% | | 0.00 | 0.00% | | 0.00 | 0.00% | | 0.00 | 0.00% | 0.00 |
| 15 | 0.00% | | 0.00 | 0.00% | | 0.00 | 0.00% | | 0.00 | 0.00% | | 0.00 | 0.00% | 0.00 |
| 16 | 0.00% | | 0.00 | 0.00% | | 0.00 | 0.00% | | 0.00 | 0.00% | | 0.00 | 0.00% | 0.00 |
| 17 | 0.00% | | 0.00 | 0.00% | | 0.00 | 0.00% | | 0.00 | 0.00% | | 0.00 | 0.00% | 0.00 |
| 18 | 0.00% | | 0.00 | 0.00% | | 0.00 | 0.00% | | 0.00 | 0.00% | | 0.00 | 0.00% | 0.00 |
| 19 | 0.00% | | 0.00 | 0.00% | | 0.00 | 0.00% | | 0.00 | 0.00% | | 0.00 | 0.00% | 0.00 |
| 20 | 0.00% | | 0.00 | 0.00% | | 0.00 | 0.00% | | 0.00 | 0.00% | | 0.00 | 0.00% | 0.00 |
| TOTAL | 0.45% | 14.50 | 0.07 | 86.46% | 36.66 | 31.70 | 9.90% | 33.00 | 3.27 | 3.19% | 36.10 | 1.15 | 100.00% | 36.18 |

Experiment 6

Diketene reductions in continuous flow reactor system on a nickel-alumina catalyst: 5.3 g of the NiO—Al$_2$O$_3$ catalyst (Unicat, NH-100, extruded) was placed in the reactor described in experiment 5 above and covered on top with 1.3 g glass beads. The reactor was purged with nitrogen followed by a stream of 5% H$_2$/nitrogen at 0.4 l/min overnight at temperature of the reactor at 190° C. and then 5% H$_2$/nitrogen was replaced by a stream of pure hydrogen at 0.4 l/min at 190-195° C. for 2 h. The reactor was initially heated to 193° C., hydrogen pressure was set up to 300 psi at hydrogen flow rate of 0.3 l/min and HPLC pump was turned on to pump diketene (GC: 95.1% diketene, 3.5% acetic acid, 0.7% acetic anhydride) at a rate of 0.05 ml/min. The experiment was run for 1.5 h at temperature gradient from 195 to 240° C. (catalyst temp at middle of the reactor) and samples of the reaction mixture were collected and analyzed by GC-MS analysis (in methyl acetate). GCMS qualitative analysis of products formed is shown in Table 5 and also a theoretical estimation of the calorific value of a sample mixture 3 (S3) is shown in Table 5a. 100% of diketene was reacted with product showing 41-51% higher alcohols of which 35-43% was 1-butanol and 2-butanol. The mixture was observed to also contain other products including butyrate esters, acetic acid which along with higher alcohols were about 88%.

| Reactor temp., ° C. | 225 | 232 | 237 | 242 | 213 |
|---|---|---|---|---|---|
| Process time, min | 48 | 58 | 68 | 80 | 93 |
| (sample no.) | (S1) | (S2) | (S3) | (S4) | (S5) |
| Sample weight | 0.48 g | 0.39 g | 0.32 g | 0.34 g | 0.10 g |
| | GCMS Area % | | | | |
| 2-Butanol | 2.7 | 1.7 | 2.0 | 2.0 | 1.3 |
| Acetic acid | 1.7 | 1.6 | 1.3 | 1.1 | 1.2 |

-continued

| Reactor temp., ° C. | 225 | 232 | 237 | 242 | 213 |
|---|---|---|---|---|---|
| 1-Butanol | 40.2 | 37.8 | 37.6 | 38.3 | 33.4 |
| 2-Pentanol | 1.9 | 1.2 | 1.1 | 1.0 | 0.9 |

-continued

| Reactor temp., °C. | 225 | 232 | 237 | 242 | 213 |
|---|---|---|---|---|---|
| Butyric acid i-propyl ester | 1.2 | 1.1 | 1.2 | 1.3 | 0.7 |
| Butyric acid | 19.2 | 22.6 | 22.5 | 20.9 | 25.4 |
| 3-Hydroxybutyric acid methyl ester | 1.7 | 1.9 | 1.6 | 1.1 | 1.1 |
| 4-Heptanol | 3.4 | 2.8 | 2.7 | 2.6 | 3.0 |
| 2-Heptanol | 2.4 | 2.0 | 2.0 | 1.9 | 2.0 |
| Butyric acid butyl ester | 13.4 | 15.0 | 16.4 | 18.2 | 19.0 |
| 1-Butanol + 2-Butanol | 42.9 | 39.5 | 39.6 | 40.3 | 34.7 |

3.9% acetic anhydride) at a rate of 0.05 ml/min. The experiment was run for 1.7 h at temperature gradient from 190 to 220° C. (catalyst temp at middle of the reactor) and samples of the reaction mixture were collected and analyzed by GC-MS analysis (in methyl acetate). GCMS qualitative analysis of products formed is shown in Table 6 and also a theoretical estimation of the calorific value of a sample mixture 5 (S5) is shown in Table 6a. 100% of diketene was reacted, samples showed 91-96% of product included a mixture of higher alcohols, butyrate esters and acetic acid, higher alcohols were in 34-77% range of which 33-77% was 1-butanol and 2-butanol.

TABLE 5a

Products in Ni-alumina diketene reduction mixture sample 3 with an energy estimation of the same.

| | Acids | | | Alcohols | | | Esters | | | Ketones | | | TOTAL | |
|---|---|---|---|---|---|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG |
| 1 | 0.00% | | 0.00 | 0.00% | | 0.00 | 0.00% | | 0.00 | 0.00% | | 0.00 | 0.00% | 0.00 |
| 2 | 0.90% | 14.50 | 0.13 | 0.00% | | 0.00 | 0.00% | | 0.00 | 0.00% | | 0.00 | 0.90% | 14.50 |
| 3 | 0.00% | | 0.00 | 0.00% | | 0.00 | 0.00% | | 0.00 | 0.00% | | 0.00 | 0.00% | 0.00 |
| 4 | 22.53% | 24.80 | 5.59 | 33.43% | 35.90 | 12.00 | 0.00% | | 0.00 | 0.36% | 33.90 | 0.12 | 56.31% | 31.45 |
| 5 | 0.00% | | 0.00 | 1.10% | 37.80 | 0.42 | 3.27% | 28.40 | 0.93 | 0.00% | 0.00 | 0.00 | 4.37% | 30.77 |
| 6 | 0.00% | | 0.00 | 2.71% | 39.10 | 1.06 | 0.81% | 30.56 | 0.25 | 0.00% | | 0.00 | 3.52% | 37.14 |
| 7 | 0.00% | | 0.00 | 6.13% | 40.10 | 2.46 | 1.80% | 32.18 | 0.58 | 0.00% | 0.00 | 0.00 | 7.93% | 38.30 |
| 8 | 0.00% | | 0.00 | 0.00% | | 0.00 | 26.97% | 33.60 | 9.06 | 0.00% | | 0.00 | 26.97% | 33.60 |
| 9 | 0.00% | | 0.00 | 0.00% | | 0.00 | 0.00% | | 0.00 | 0.00% | | 0.00 | 0.00% | 0.00 |
| 10 | 0.00% | | 0.00 | 0.00% | | 0.00 | 0.00% | | 0.00 | 0.00% | | 0.00 | 0.00% | 0.00 |
| 11 | 0.00% | | 0.00 | 0.00% | | 0.00 | 0.00% | | 0.00 | 0.00% | | 0.00 | 0.00% | 0.00 |
| 12 | 0.00% | | 0.00 | 0.00% | | 0.00 | 0.00% | | 0.00 | 0.00% | | 0.00 | 0.00% | 0.00 |
| 13 | 0.00% | | 0.00 | 0.00% | | 0.00 | 0.00% | | 0.00 | 0.00% | | 0.00 | 0.00% | 0.00 |
| 14 | 0.00% | | 0.00 | 0.00% | | 0.00 | 0.00% | | 0.00 | 0.00% | | 0.00 | 0.00% | 0.00 |
| 15 | 0.00% | | 0.00 | 0.00% | | 0.00 | 0.00% | | 0.00 | 0.00% | | 0.00 | 0.00% | 0.00 |
| 16 | 0.00% | | 0.00 | 0.00% | | 0.00 | 0.00% | | 0.00 | 0.00% | | 0.00 | 0.00% | 0.00 |
| 17 | 0.00% | | 0.00 | 0.00% | | 0.00 | 0.00% | | 0.00 | 0.00% | | 0.00 | 0.00% | 0.00 |
| 18 | 0.00% | | 0.00 | 0.00% | | 0.00 | 0.00% | | 0.00 | 0.00% | | 0.00 | 0.00% | 0.00 |
| 19 | 0.00% | | 0.00 | 0.00% | | 0.00 | 0.00% | | 0.00 | 0.00% | | 0.00 | 0.00% | 0.00 |
| 20 | 0.00% | | 0.00 | 0.00% | | 0.00 | 0.00% | | 0.00 | 0.00% | | 0.00 | 0.00% | 0.00 |
| TOTAL | 23.43% | 24.40 | 5.72 | 43.37% | 36.74 | 15.93 | 32.85% | 32.93 | 10.82 | 0.36% | 33.90 | 0.12 | 100.00% | 32.59 |

Experiment 7

Diketene reductions in continuous flow reactor system on a Cu—Zn and nickel-alumina catalyst: First 5.1 g of the CuO—ZnO catalyst (Unicat, LS-402, 5×2 mm) and then 1.97 g of the NiO—Al$_2$O$_3$ catalyst (Unicat, NH-100, extruded) was placed in the reactor described in experiment 5 above covered on top with 1.4 g glass beads were placed in the reactor. The reactor was purged with nitrogen followed by a stream of 5% H$_2$/nitrogen at 0.4 l/min overnight at temperature of the reactor at 230-240° C. and then 5% H$_2$/nitrogen was replaced by a stream of pure hydrogen at 0.4 l/min at 210° C. for 2 h. The reactor was initially heated to 212° C., hydrogen pressure was set up to 300 psi at hydrogen flow rate of 0.3 l/min and HPLC pump was turned on to pump diketene (GC: 91.6% diketene, 2.9% acetic acid,

TABLE 6

Products seen in GCMS samples of Cu—ZnO + Ni-alumina diketene reduction samples taken over time.

| Reactor temp., °C. | 197 | 194 | 190 | 189 | 195 |
|---|---|---|---|---|---|
| Process time, min (sample #) | 60 (S1) | 70 (S2) | 80 (S3) | 90 (S4) | 101 (S5) |
| Sample weight | 0.31 g | 0.36 g | 0.30 g | 0.24 g | 0.34 g |
| | GCMS Area % | | | | |
| 2-Butanol | 11.5 | 1.7 | 1.3 | 1.5 | 1.0 |
| Acetic acid | 9.4 | 0.9 | 0.7 | 0.7 | 0.8 |
| 1-Butanol | 65.8 | 56.5 | 49.0 | 42.4 | 32.3 |
| 2-Pentanol | — | — | 0.3 | — | — |
| Butyric acid methyl ester | — | 1.0 | 1.1 | 1.0 | 1.0 |
| Butyric acid ethyl ester | — | 0.7 | 0.9 | 1.1 | 1.4 |
| Butyric acid i-propyl ester | — | 0.7 | 0.9 | 1.1 | 1.4 |
| Butyric acid | 4.7 | 11.5 | 13.9 | 14.3 | 17.1 |

TABLE 6-continued

Products seen in GCMS samples of Cu—ZnO + Ni-alumina diketene reduction samples taken over time.

| Reactor temp., ° C. | 197 | 194 | 190 | 189 | 195 |
|---|---|---|---|---|---|
| 3-Hydroxybutyric acid methyl ester | 4.0 | 1.7 | 2.0 | 2.1 | 2.1 |
| 4-Heptanol | — | 0.7 | 0.6 | 0.5 | 0.5 |
| Butyric acid butyl ester | — | 20.1 | 23.3 | 28.3 | 33.3 |
| 1-Butanol + 2-Butanol | 77.3 | 58.2 | 50.3 | 43.9 | 33.3 |

TABLE 6a

Products in sample 5 Cu—ZnO + Ni-alumina diketene reduction mixture with an energy estimation of the same

| | Acids | | | Alcohols | | | Esters | | | TOTAL | | |
|---|---|---|---|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG |
| 1 | 0.00% | | 0.00 | 0.00% | | 0.00 | 0.00% | | 0.00 | 0.00% | 0.00 | 0.00 |
| 2 | 0.46% | 14.50 | 0.07 | 0.00% | | 0.00 | 0.00% | | 0.00 | 0.46% | 14.50 | 0.07 |
| 3 | 0.00% | | 0.00 | 0.00% | | 0.00 | 0.00% | | 0.00 | 0.00% | 0.00 | 0.00 |
| 4 | 15.29% | 24.80 | 3.79 | 25.11% | 35.90 | 9.01 | 0.00% | | 0.00 | 40.41% | 31.70 | 12.81 |
| 5 | 0.00% | | 0.00 | 0.00% | 0.00 | 0.00 | 3.47% | 28.40 | 0.99 | 3.47% | 28.40 | 0.99 |
| 6 | 0.00% | | 0.00 | 2.58% | 39.10 | 1.01 | 1.70% | 30.56 | 0.52 | 4.27% | 35.71 | 1.53 |
| 7 | 0.00% | | 0.00 | 0.64% | 40.10 | 0.26 | 1.81% | 32.18 | 0.58 | 2.46% | 34.25 | 0.84 |
| 8 | 0.00% | | 0.00 | 0.00% | | 0.00 | 48.93% | 33.60 | 16.44 | 48.93% | 33.60 | 16.44 |
| 9 | 0.00% | | 0.00 | 0.00% | | 0.00 | 0.00% | | 0.00 | 0.00% | 0.00 | 0.00 |
| 10 | 0.00% | | 0.00 | 0.00% | | 0.00 | 0.00% | | 0.00 | 0.00% | 0.00 | 0.00 |
| 11 | 0.00% | | 0.00 | 0.00% | | 0.00 | 0.00% | | 0.00 | 0.00% | 0.00 | 0.00 |
| 12 | 0.00% | | 0.00 | 0.00% | | 0.00 | 0.00% | | 0.00 | 0.00% | 0.00 | 0.00 |
| 13 | 0.00% | | 0.00 | 0.00% | | 0.00 | 0.00% | | 0.00 | 0.00% | 0.00 | 0.00 |
| 14 | 0.00% | | 0.00 | 0.00% | | 0.00 | 0.00% | | 0.00 | 0.00% | 0.00 | 0.00 |
| 15 | 0.00% | | 0.00 | 0.00% | | 0.00 | 0.00% | | 0.00 | 0.00% | 0.00 | 0.00 |
| 16 | 0.00% | | 0.00 | 0.00% | | 0.00 | 0.00% | | 0.00 | 0.00% | 0.00 | 0.00 |
| 17 | 0.00% | | 0.00 | 0.00% | | 0.00 | 0.00% | | 0.00 | 0.00% | 0.00 | 0.00 |
| 18 | 0.00% | | 0.00 | 0.00% | | 0.00 | 0.00% | | 0.00 | 0.00% | 0.00 | 0.00 |
| 19 | 0.00% | | 0.00 | 0.00% | | 0.00 | 0.00% | | 0.00 | 0.00% | 0.00 | 0.00 |
| 20 | 0.00% | | 0.00 | 0.00% | | 0.00 | 0.00% | | 0.00 | 0.00% | 0.00 | 0.00 |
| TOTAL | 15.75% | 24.50 | 3.86 | 28.33% | 36.29 | 10.28 | 55.92% | 33.14 | 18.53 | 100.00% | 32.67 | 32.67 |

Experiment 8

Hydrogenation of beta-butyrolactone (BBL) with a Cu—Cr catalyst in a batch reactor: The reduction reaction was performed in a hydrogenation reactor consisting of a ½" diameter stainless steel tube fitted with a ball valve at the bottom and a cross on the top. A thermocouple, side arm bearing a pressure gauge and pressure relief valve and a ball valve were attached to three arms of the cross and the third arm was attached to the top of the stainless steel tube. The tube was wrapped with heating rope and insulation was wrapped around the heating rope. The ball valve on the bottom of the reactor is connected to a 3" length of ⅛" tube immersed in a cold water bath which is connected to a 1/16" tube bearing a ball valve and needle valve to collect liquid samples from the reactor. Procedure: 15.3 g of the barium promoted copper chromite catalyst (Stream Chemicals, (62-64% $Cr_2CuO_4$, 22-24% CuO, 6% BaO) was placed in the hydrogenation reactor and purged with nitrogen followed by a stream of 5% $H_2$/nitrogen at 0.2 l/min overnight at temperature of the reactor 180° C. The 5% $H_2$/nitrogen was replaced by a stream of pure hydrogen at 0.2 l/min for 1 h. The hydrogen stream was replaced with nitrogen and the reactor was cooled down to room temperature and under continuous nitrogen flow 0.50 ml of BBL was injected into the catalyst bed. The reactor was washed 3 times with hydrogen and then filled with hydrogen to a pressure of 600 psi. Heating was started and temperature of the catalyst bed was maintained at 180-190° C. and hydrogen pressure at 500-700 psi for 3 h. The reactor was cooled down to room temperature, washed with nitrogen and the catalyst was removed and washed with 2 ml of methyl acetate. The wash was filtered and directly analyzed by GC-MS. Similar experiments were performed using CuO/ZnO, Ni/alumina and Ru/alumina catalysts. The obtained results are summarized in Table 7.

TABLE 7

Products from GCMS analysis of BBL hydrogenation

| | | GC/MS: area % [1] | | | |
|---|---|---|---|---|---|
| Catalyst | Conditions | 1-Butanol | 2-Butanol | Σ Butanols | Σ Butyrates [2] |
| Cu chromite | 180°-190° C., 500-700 psi, 3 h | 47.1 | 2.6 | 49.7 | 17.4 |
| 35%CuO—65%ZnO | 180°-190° C., 600-700 psi, 3 h | 37.4 | 20.7 | 58.1 | 8.8 |

TABLE 7-continued

Products from GCMS analysis of BBL hydrogenation

| | | GC/MS: area % [1] | | | |
|---|---|---|---|---|---|
| Catalyst | Conditions | 1-Butanol | 2-Butanol | Σ Butanols | Σ Butyrates [2] |
| 50%NiO/alumina | 180°-200° C., 600-760 psi, 5 h | 33.2 | 16.7 | 49.9 | 14.4 |
| 2%Ru/alumina | 180°-195° C., 500-640 psi, 4 h | 4.7 | 5.0 | 9.7 | 21.2 |

[1] Peaks related to the solvent component (ethyl acetate and acetic acid) are excluded.
[2] Butyrates include butyric acid and its esters, esters of 3-hydroxybutyric acid and 1,3-butanediol.

Continuous Flow Reactor Experiments BBL:

Experiment 9

Hydrogenation of BBL with a Ni-alumina catalyst: Continuous flow reactor setup: The reduction reaction was performed in a steel tube reactor (made from Swagelok parts) consisting of a ½" diameter stainless steel tube fitted with a ball valve at the bottom and a ¼" union stainless steel cross on the top. A thermocouple was attached to the top arm of the cross with one of the (cross) side arms bearing a pressure gauge, pressure relief valve and a ball valve. The other side arm of the ¼" union cross was connected to a 1/16" tube which was attached to a Gilson 307 HPLC pump. The 1/16" tube entered the reactor and extended down till it was just above the catalyst bed. The bottom arm of the cross was attached to the top of the ½" stainless steel tube. The tube was wrapped with heating rope and insulation was wrapped around the heating rope. Another thermocouple was placed under the heating rope. Both the thermocouples were connected to a digital display. The ball valve on the bottom of the reactor is connected to a coil of ⅛" stainless steel tube that was connected to 2" length of ¼ inch tube with a drain at its bottom for liquid condensate and a vent near its top that carried out non-condensing gases. This coiled tube and lower portion are cooled with ice water and served as a trap to collect liquid. The end of the gas vent had a ball valve and the liquid collecting end had a needle valve so that it could be opened slowly to collect liquid samples. Procedure: 7.0 g of the NiO/alumina catalyst (Unicat, 50% NiO/Al$_2$O$_3$) was placed in the reactor and covered on top with 0.9 g glass beads. The reactor was purged with nitrogen followed by a stream of 5% H$_2$/nitrogen at 0.3 l/min overnight at temperature of the reactor 180° C. and then 5% H$_2$/nitrogen was replaced by a stream of pure hydrogen at 0.3 l/min for 1 h. The reactor was initially heated to 260° C., hydrogen pressure was set up to 300 psi at hydrogen flow rate of 0.40 l/min, HPLC pump was turned on and BBL was pumped at a rate of 0.04 ml/min. The experiment was run for 6 h at temperature gradient from 260 to 170° C. and samples of the reaction mixture were collected and analyzed by GC-MS analysis (in methyl acetate). The obtained results are summarized in the Table 8.

TABLE 8

Products in GCMS analysis of Ni-alumina BBL hydrogenation taken over time.

| Sample No. | S2 | S3 | S4 | S6 | S7 | S8 | S9 | S10 | S11 | S12 | S13 | S15 | S16 | S17 |
|---|---|---|---|---|---|---|---|---|---|---|---|---|---|---|
| Reactor temp., ° C. | 260 | 259 | 259 | 254 | 251 | 257 | 253 | 242 | 196 | 180 | 180 | 185 | 187 | 174 |
| Process time, min | 60 | 75 | 100 | 140 | 165 | 190 | 205 | 220 | 230 | 245 | 255 | 305 | 325 | 355 |
| Sample wt. gms. | .13 g | .21 g | .31 g | .24 g | .41 g | .40 g | .27 g | .24 g | .17 g | .22 g | .10 g | .20 g | .65 g | .85 g |
| | | | | | GCMS Area % | | | | | | | | | |
| Acetic acid | 77.7 | 85.1 | 81.7 | 87.8 | 69.4 | 5.7 | 8.8 | 9.4 | 9.0 | 13.4 | 21.2 | 2.3 | 0.4 | 1.2 |
| 1-Butanol | — | — | — | — | 19.1 | 74.4 | 86.8 | 87.3 | 88.0 | 83.7 | 74.3 | 40.5 | 13.9 | 4.7 |
| Butyric acid | — | — | — | — | — | — | — | — | — | — | — | 44.1 | 80.0 | 90.7 |
| Butyl butyrate | — | — | — | — | — | — | — | — | — | — | — | 10.5 | 3.7 | 1.9 |
| BBL | — | — | — | — | — | — | — | — | — | — | — | — | — | — |

Experiment 10

Hydrogenation of BBL with a Ni-alumina catalyst at around 250° C.: 9.5 g of the NiO/alumina catalyst (Unicat, 50% NiO/Al$_2$O$_3$) was placed in the reactor described in experiment above and covered on top with 1.2 g glass beads. The reactor was purged with nitrogen followed by a stream of 5% H$_2$/nitrogen at 0.3 l/min overnight at temperature of the reactor 180° C. and then 5% H$_2$/nitrogen was replaced by a stream of pure hydrogen at 0.3 l/min for 1 h. The reactor was initially heated to 250° C., hydrogen pressure was set up to 400 psi at hydrogen flow rate of 0.40 l/min, HPLC pump was turned on and BBL was pumped at a rate of 0.03-0.04 ml/min. The experiment was run for 6.7 h at temperature gradient from 250 to 180° C. and samples of the reaction mixture were collected and analyzed by GC-MS analysis (in methyl acetate). The obtained results are summarized in the Table 9.

TABLE 9

Products seen in GCMS of products from Ni-alumina hydrogenation of BBL over time.

| Reactor temp., °C. | 254 | 256 | 225 | 228 | 227 | 227 | 225 | 252 | 254 | 180 |
|---|---|---|---|---|---|---|---|---|---|---|
| Process time, min | 165 | 195 | 220 | 245 | 265 | 285 | 305 | 330 | 350 | 400 |
| BBL flow, ml/min | 0.03 | 0.03 | 0.03 | 0.04 | 0.04 | 0.04 | 0.04 | 0.04 | 0.04 | 0.04 |
| Sample no. | S3 | S4 | S5 | S7 | S8 | S9 | S10 | S11 | S12 | S15 |
| Sample wt. gms | .24 g | .35 g | .17 g | .15 g | .44 g | .45 g | .35 g | .73 g | .74 g | .14 g |
| GCMS Area % | | | | | | | | | | |
| Acetic acid | 35.7 | 31.6 | 26.0 | 14.8 | 1.5 | 0.9 | — | 0.9 | 0.2 | — |
| 1-Butanol | 16.5 | 25.1 | 43.8 | 66.4 | 66.6 | 61.9 | 57.2 | 33.8 | 30.6 | 26.6 |
| 2-Butanol | 30.9 | 29.9 | 20.5 | 11.6 | 1.6 | 0.9 | 0.9 | 0.4 | 0.5 | — |
| Σ Butanols | 47.4 | 55.0 | 64.3 | 78.0 | 68.2 | 62.8 | 58.1 | 34.2 | 31.1 | 26.6 |
| Butyric acid | — | — | — | — | — | 7.7 | 17.5 | 47.6 | 49.1 | 54.3 |
| Butyl buytyrate | — | trace | trace | — | 20.9 | 22.3 | 19.8 | 13.7 | 14.7 | 13.8 |
| BBL | 1.6 | trace | trace | — | — | — | — | — | — | — |

Experiment 11

Hydrogenation of BBL with a Ni-alumina catalyst as temperature was varied: 7.25 g of the NiO/alumina catalyst (Unicat, 50% NiO/Al$_2$O$_3$) was placed in the reactor and covered on top with 2.5 g glass beads. The reactor was purged with nitrogen followed by a stream of 5% H$_2$/nitrogen at 0.3 l/min overnight at temperature of the reactor 180° C. and then 5% H$_2$/nitrogen was replaced by a stream of pure hydrogen at 0.3 l/min for 1 h. The reactor was initially heated to 220° C., hydrogen pressure was set up to 300 psi at hydrogen flow rate of 0.40 l/min, HPLC pump was turned on and BBL was pumped at a rate of 0.05 ml/min. The experiment was run for 6.5 h at temperature gradient from 220 to 200° to 240° C. and samples of the reaction mixture were collected and analyzed by GC-MS analysis (in methyl acetate). The obtained results are summarized in the Table 10.

a digital display. The top of the reactor was connected to a T-union one side arm of the union was connected to a 1/16" tube that was connected to a waters HPLC pump. The intake of the pump was dipped in MAA contained in a 50 ml measuring cylinder. The other arm of the T-union on the top of the reactor was connected to a pressure transducer, hydrogen supply and a differential pressure gauge to adjust pressure and flow rate. The bottom end of the reactor was connected to a liquid condenser cooled by circulating ice water by a 1/4" stainless steel tube. The condenser had a ball valve at its bottom to open and collect liquid samples. The gas outlet of the condenser was connected to a back pressure gauge that enabled control of reactor pressure which was in turn connected to a flow meter that vented reactor gases to the hood via a tube. Procedure: 95 g of copper/zinc oxide catalyst from Unicat (LS-402) was loaded into the reactor and reduced overnight at 180 to 190° C. over a stream of 5% hydrogen 95% nitrogen flowing at about 500 ml/min Next

TABLE 10

Products seen in GCMS analysis of BBL Ni-alumina hydrogenation over time.

| Reactor temp., °C. | 221 | 224 | 224 | 224 | 199 | 201 | 201 | 233 | 247 | 232 | 224 | 239 |
|---|---|---|---|---|---|---|---|---|---|---|---|---|
| Process time, min | 112 | 127 | 147 | 182 | 222 | 247 | 287 | 327 | 340 | 352 | 368 | 389 |
| Sample no. | S2 | S3 | S4 | S5 | S7 | S8 | S9 | S10 | S11 | S12 | S13 | S14 |
| Sample wt. gms | .03 | .32 g | .43 g | 1.01 g | .58 g | .83 g | 1.56 g | 1.77 g | 1.05 g | .43 g | .55 g | |
| GCMS Area % | | | | | | | | | | | | |
| 1-Butanol | 56.6 | 69.0 | 70.9 | 49.1 | 26.5 | 13.4 | 6.9 | 3.3 | 2.6 | 3.5 | 3.7 | 2.5 |
| 2-Butanol | 10.6 | 3.1 | 1.4 | — | 0.5 | — | — | — | — | — | — | — |
| Σ Butanols | 67.2 | 72.1 | 72.3 | 49.1 | 27.0 | 13.4 | 6.9 | 3.3 | 2.6 | 3.5 | 3.7 | 2.5 |
| Butyric acid | — | — | — | 30.1 | 61.4 | 78.7 | 77.6 | 93.8 | 94.2 | 91.4 | 91.0 | 92.7 |
| Butyl buytyrate | — | 13.8 | 17.4 | 15.1 | 8.5 | 4.7 | 2.3 | 1.3 | 1.5 | 2.6 | 3.4 | 2.6 |
| BBL | 4.3 | 1.9 | 0.6 | 0.5 | — | — | — | — | — | — | — | — |

%—GCMS area percent; the peak related to the solvent component, ethyl acetate was excluded.

Reduction of Methyl Acetoacetate (MAA) Experiments:

Experiment 12

Hydrogenation of MAA with a copper-zinc catalyst; continuous flow reactor set up: The reduction reaction was performed in a hydrogenation reactor (made from Swagelok parts using the required unions, port connectors, reducers and valves as needed) consisting of a 1" diameter stainless steel tube reactor chamber that held catalyst. The reactor tube was wrapped in heat tape and insulation surrounded the heating tape. Five thermocouples were affixed to the reactor to monitor catalyst bed temperatures along the length of the reactor catalyst bed. The thermocouples were connected to morning, the nitrogen/hydrogen mixture was replaced by hydrogen and reduction continued for another 2 hours. Hydrogen flow rate was set to around 500 ml/min and the catalyst bed temperatures were at 200, 261 and 251° C. for up, middle and bottom reactor zones respectively. 50 ml of MAA (purchased from Alfa Aesar) was poured into the HPLC pump reservoir, the pump purged for air bubbles and flow commenced onto the reactor catalyst bed at 0.7 ml/min Liquid sample was taken after about 30 minutes had passed and taken at about 10 minute intervals. GCMS of the samples (Table 1) indicated 2-butanol and 1-butanol as major products. Samples were analyzed for lower boiling solvents on a Gowmac GC system indicating ethanol, acetone, isopropanol, 1-propanol, 2-butanol and 1-butanol were in ratios of 7.7:0.6:18.9:0.7:45.1:26.9, respectively. The obtained results are summarized in the Table 11. 100% MAA was converted. 84-91% of products included higher alcohols and smaller amounts of methyl butyrate, 82-89% was higher alcohols of which 71-79% was 1-butanol and 2-butanol.

TABLE 11

Products observed from GCMS analysis Cu—ZnO MAA hydrogenation.

| | Sample No. | | |
|---|---|---|---|
| | S3 | S4 | S5 |
| Time (minutes) | 80 | 90 | 110 |
| Reaction Temperatures ° C. | | | |
| T1 | 67 | 70 | 67 |
| T2 | 119 | 120 | 116 |
| T3 | 183 | 185 | 176 |
| T4 | 272 | 270 | 265 |
| T5 | 262 | 265 | 265 |
| GCMS Area Percent | | | |
| 2-Butanol area | 51.5 | 42.7 | 46.8 |
| 1-Butanol area | 27.7 | 28.4 | 30.2 |
| Methyl butyrate | 2.0 | 2.4 | 2.5 |
| 3-Hexanol | 1.8 | 2.4 | 1.8 |
| 4-Heptanol | 1.9 | 2.0 | 2.0 |
| 2-Heptanol | 1.2 | 1.4 | 1.3 |
| Ocatanol isomer | 1.4 | 1.4 | 1.2 |
| 4-Octanol | 1.6 | 1.8 | 1.7 |
| 3-Octanol | 1.5 | 1.7 | 1.7 |

Experiment 13

Hydrogenation of MAA with a copper-zinc catalyst as temperature was varied: To the reduced catalyst bed used in the experiment above heated to temperature range of 193 to 218° C., MAA was added via the HPLC pump at 0.7 ml/min. Liquid sample was collected after 18 minutes after the start of the pump and samples were analyzed on GCMS. Temperature of the reactor rose after initial liquid input and was controlled by decreasing heating from the heat tape. The top of the reactor was cooled to around 115° C. and the bottom zone had a temperature of around 245° C. The obtained results of GCMS qualitative analysis are summarized in the Table 12. 100% of MAA was reacted. 84-89% of product included higher alcohols and methyl butyrate of which 79-86% was higher alcohols and 74-80% are 1-butanol and 2-butanol.

TABLE 12

Products seen in GCMS analysis of products from MAA Cu—ZnO below 250 C. hydrogenation over time.

| | Sample No. | | | | |
|---|---|---|---|---|---|
| | S3 | S7 | S9 | S12 | S14 |
| Time (minutes) | 35 | 60 | 80 | 184 | 232 |
| Reaction Temperatures ° C. | | | | | |
| T1 | 63 | 61 | 61 | 63 | 71 |
| T2 | 116 | 107 | 108 | 112 | 128 |
| T3 | 179 | 159 | 155 | 167 | 183 |
| T4 | 254 | 229 | 230 | 233 | 223 |
| T5 | 254 | 249 | 249 | 248 | 226 |

TABLE 12-continued

Products seen in GCMS analysis of products from MAA Cu—ZnO below 250 C. hydrogenation over time.

| | Sample No. | | | | |
|---|---|---|---|---|---|
| | S3 | S7 | S9 | S12 | S14 |
| GCMS Area Percent | | | | | |
| 2-Butanol | 50.6 | 46.5 | 47.5 | 46.1 | 43.5 |
| 1-Butanol | 29.4 | 30.1 | 28.1 | 29.8 | 30.8 |
| Methyl butyrate | 3.2 | 4.7 | 5.6 | 4.8 | 5.2 |
| 3-Hexanol | 1.2 | 0.9 | 0.5 | 0.6 | 0.6 |
| 4-Heptanol | 0.9 | 0.9 | 0.7 | 0.7 | 0.9 |
| 2-Heptanol | 0.6 | 0.6 | 0.4 | 0.4 | 0.6 |
| Ocatanol isomer | 1.0 | 0.9 | 0.7 | 0.8 | 0.9 |
| 4-Octanol | 1.2 | 1.0 | 0.8 | 0.8 | 0.9 |
| 3-Octanol | 1.0 | 0.9 | 0.5 | 0.4 | 0.6 |

Experiment 14

Hydrogenation of MAA with a copper-zinc catalyst as temperature was varied near 200° C.: 11.9 g of the CuO—ZnO catalyst (Unicat, LS-402, 5×2 mm) was placed in the reactor and covered on top with 1.9 g glass beads. The reactor was purged with nitrogen followed by a stream of 5% $H_2$/nitrogen at 0.4 l/min overnight at temperature of the reactor at 150° C. and then 5% $H_2$/nitrogen was replaced by a stream of pure hydrogen at 0.4 l/min at 200° C. for 2 h. The reactor was initially heated to 204° C., hydrogen pressure was set up to 300 psi at hydrogen flow rate of 0.4 l/min and HPLC pump was turned on to pump MAA (Alfa-Aesar, 99%) at a rate of 0.1 ml/min. The experiment was run for 3.2 h at temperature gradient from 190 to 200° C. and samples of the reaction mixture were collected for GS-MS analysis. GCMS qualitative analysis of higher alcohols formed is shown in Table 13 and also a theoretical estimation of the calorific value of a sample mixture 8 (S8) is shown in Table 13a. 100% of MAA was reacted. 81-89% of the product showed higher alcohols, ketones and butyric acid esters. 64-71% was higher alcohols of which 51-60% was 1-butanol and 2-butanol.

TABLE 13

Products seen in GCMS of product samples from Cu—ZnO below 200° C. hydrogenation of MAA.

| Reactor temp., ° C. | 188 | 189 | 189 | 190 | 194 | 194 |
|---|---|---|---|---|---|---|
| Process time, min | 65 | 86 | 105 | 125 | 145 | 165 |
| (sample #) | (S4) | (S6) | (S8) | (S10) | (S12) | (S14) |
| Sample weight gms | 0.73 | 0.90 | 0.72 | 0.91 | 0.54 | 0.71 |
| GCMS Area % | | | | | | |
| 2-Butanone | 2.6 | 2.4 | 2.2 | 2.4 | 2.5 | 2.6 |
| 2-Butanol | 32.9 | 30.7 | 29.0 | 29.6 | 30.5 | 34.4 |
| 1-Butanol | 26.1 | 23.4 | 22.9 | 22.4 | 22.6 | 25.4 |
| 2-Pentanone | 1.7 | 1.3 | 1.2 | 1.1 | 1.5 | 1.3 |
| 2-Pentanol | 3.8 | 3.9 | 3.8 | 3.7 | 3.7 | 4.0 |
| Butyric acid methyl ester | 3.1 | 2.5 | 2.3 | 2.8 | 2.8 | 3.5 |
| Butyric acid ethyl ester | 4.7 | 5.3 | 5.4 | 5.3 | 5.3 | 4.6 |
| Butyric acid i-propyl ester | 1.2 | 1.0 | 1.0 | 1.0 | 1.0 | — |
| 4-Heptanone | 1.0 | 1.0 | 1.1 | 1.0 | 1.0 | — |
| 4-Heptanol | 4.3 | 4.4 | 4.4 | 4.3 | 4.2 | 3.6 |
| 2-Heptanol | 2.7 | 3.0 | 3.1 | 2.8 | 2.7 | 2.4 |
| Butyric acid sec-butyl ester | 1.7 | 1.6 | 1.7 | 1.8 | 1.7 | 1.9 |

TABLE 13-continued

Products seen in GCMS of product samples from Cu—ZnO below 200° C. hydrogenation of MAA.

| Reactor temp., ° C. | 188 | 189 | 189 | 190 | 194 | 194 |
|---|---|---|---|---|---|---|
| 3-Methyl cyclohexanol | 1.4 | 1.3 | 1.5 | 1.2 | 1.2 | 1.1 |
| Butyric acid butyl ester | 1.6 | 1.6 | 1.7 | 1.7 | 1.7 | 1.6 |
| 1-Butanol + 2-Butanol | 59.0 | 54.1 | 51.9 | 52.0 | 53.1 | 59.8 |

TABLE 13a

Products in GCMS for Cu—ZnO below 200 C. reaction sample 8 of methyl acetoacetate reduction mixture with an energy estimation of the same.

| | Acids | | | Alcohols | | | Esters | |
|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG |
| 1 | 0.00% | | 0.00 | 0.00% | | 0.00 | 0.00% | |
| 2 | 1.29% | 14.50 | 0.19 | 0.00% | | 0.00 | 0.00% | |
| 3 | 0.00% | | 0.00 | 0.00% | | 0.00 | 0.00% | |
| 4 | 1.19% | 24.80 | 0.30 | 51.67% | 35.90 | 18.55 | 0.00% | |
| 5 | 0.00% | | 0.00 | 4.40% | 37.80 | 1.66 | 3.13% | 28.40 |
| 6 | 0.00% | | 0.00 | 10.63% | 39.10 | 4.16 | 1.38% | 30.56 |
| 7 | 0.00% | | 0.00 | 13.75% | 40.10 | 5.51 | 1.62% | 32.18 |
| 8 | 0.00% | | 0.00 | 0.00% | | 0.00 | 6.26% | 33.60 |
| 9 | 0.00% | | 0.00 | 0.00% | | 0.00 | 0.00% | |
| 10 | 0.00% | | 0.00 | 0.00% | | 0.00 | 0.00% | |
| 11 | 0.00% | | 0.00 | 0.00% | | 0.00 | 0.00% | |
| 12 | 0.00% | | 0.00 | 0.00% | | 0.00 | 0.00% | |
| 13 | 0.00% | | 0.00 | 0.00% | | 0.00 | 0.00% | |
| 14 | 0.00% | | 0.00 | 0.00% | | 0.00 | 0.00% | |
| 15 | 0.00% | | 0.00 | 0.00% | | 0.00 | 0.00% | |
| 16 | 0.00% | | 0.00 | 0.00% | | 0.00 | 0.00% | |
| 17 | 0.00% | | 0.00 | 0.00% | | 0.00 | 0.00% | |
| 18 | 0.00% | | 0.00 | 0.00% | | 0.00 | 0.00% | |
| 19 | 0.00% | | 0.00 | 0.00% | | 0.00 | 0.00% | |
| 20 | 0.00% | | 0.00 | 0.00% | | 0.00 | 0.00% | |
| TOTAL | 2.48% | 19.45 | 0.48 | 80.46% | 37.14 | 29.89 | 12.39% | 31.76 |

| | Esters | Ketones | | TOTAL | |
|---|---|---|---|---|---|
| # of C's | weighted Net Energy MJ/KG | % by wt | Net Energy MJ/KG | weighted Net Energy MJ/KG | % by wt | Net Energy MJ/KG |
| 1 | 0.00 | 0.00% | | 0.00 | 0.00% | 0.00 |
| 2 | 0.00 | 0.00% | | 0.00 | 1.29% | 14.50 |
| 3 | 0.00 | 0.00% | | 0.00 | 0.00% | 0.00 |
| 4 | 0.00 | 3.07% | 33.90 | 1.04 | 55.94% | 35.55 |
| 5 | 0.89 | 0.00% | 0.00 | 0.00 | 7.53% | 33.90 |
| 6 | 0.42 | 0.00% | | 0.00 | 12.02% | 38.12 |
| 7 | 0.52 | 1.60% | 39.10 | 0.63 | 16.96% | 39.25 |
| 8 | 2.10 | 0.00% | | 0.00 | 6.26% | 33.60 |
| 9 | 0.00 | 0.00% | | 0.00 | 0.00% | 0.00 |
| 10 | 0.00 | 0.00% | | 0.00 | 0.00% | 0.00 |
| 11 | 0.00 | 0.00% | | 0.00 | 0.00% | 0.00 |
| 12 | 0.00 | 0.00% | | 0.00 | 0.00% | 0.00 |
| 13 | 0.00 | 0.00% | | 0.00 | 0.00% | 0.00 |
| 14 | 0.00 | 0.00% | | 0.00 | 0.00% | 0.00 |
| 15 | 0.00 | 0.00% | | 0.00 | 0.00% | 0.00 |
| 16 | 0.00 | 0.00% | | 0.00 | 0.00% | 0.00 |
| 17 | 0.00 | 0.00% | | 0.00 | 0.00% | 0.00 |
| 18 | 0.00 | 0.00% | | 0.00 | 0.00% | 0.00 |
| 19 | 0.00 | 0.00% | | 0.00 | 0.00% | 0.00 |
| 20 | 0.00 | 0.00% | | 0.00 | 0.00% | 0.00 |
| TOTAL | 3.94 | 4.67% | 35.68 | 1.67 | 100.00% | 35.97 |

Reduction of Dehydroacetic Acid (DHAA):

Experiment 15

Hydrogenation of DHAA in dioxane solvent with a Ru-alumina catalyst: Batch reactor system setup: The reduction reaction was performed in a hydrogenation reactor (made from Swagelok parts) consisting of a ½" diameter stainless steel tube fitted with a ball valve at the bottom and a cross on the top. A thermocouple attached to the top arm, the side arms bearing a pressure gauge and pressure relief valve and a ball valve were attached to three arms of the cross and the bottom arm was attached to the top of the stainless steel tube. The tube was wrapped with heating rope and insulation was wrapped around the heating rope. The ball valve on the bottom of the reactor is connected to a ⅛" stainless steel tube that had provision for cooling and collecting liquid samples that could be collected via a ball valve connected to a needle valve.

0.41 g of DHAA was dissolved in 1.5 mL of hot dioxane (99.8%) and the resulting homogenic solution was immediately pipetted evenly over 4.62 g of 2% Ru-alumina catalyst pellets (Alfa-Aesar). The resulting wetted catalyst was left to air for 30 minutes and then was poured into the reactor. The reactor was sealed and purged with argon and hydrogen three times each and then hydrogen was filled to a pressure of 1010 psi. Heating was started and temperature of the catalyst bed was maintained at about 200° C. (180-207° C.) for 2.5 hours. After 0.5 h the pressure in the reactor was dropped to 720 psi and was refilled with hydrogen to 1080 psi and it was 920 psi in the end of hydrogenation. The reactor was cooled down and a sample of liquid was collected from the reactor bottom and analyzed by GC/MS. The analysis indicated formation of compounds described in Table 1 below. Tables show an analysis of products using calorific values published from literature available on the National Institute of Standards and Technology website at nist.gov. For calorific values of molecules like 2-heptanol and 4-heptanol that were not readily available an isomer's heat of combustion like the 1-heptanol isomer's calorific value was used in calculations. The GCMS peaks were matched by agilent GCMS software to the NIST 2011 library of MS spectra. The quality of matches are listed on the last column of the table. The average energy of a fuel produced from the selected products of an experiment is on the last line of the tables. GCMS qualitative analysis of higher alcohols formed is shown in Table 14 and also presents a theoretical estimation of the calorific value of a mixture. 100% of DHAA was reacted. 33% of product observed was higher alcohols and some ketones. 18% higher alcohols were formed of which 16% was heptanols.

TABLE 14

Products in Ru cat. DHAA reduction at 180-207° C. mixture with an energy estimation of the same.

| Compound | GC Ret. Min. | GC Area % | Mol. Wt. | Δc liq. kJ/gm | Normlzd Wt. | Wt. Fraction | Δc liq. kJ/Kg | Energy/ comp | NIST Δc liq. kJ/mol | Lib. Match Qual. |
|---|---|---|---|---|---|---|---|---|---|---|
| 1-Butanol | 7 | 0.9 | 74 | 36.1 | 66.6 | 1.8 | 36081 | 66.06367 | 2670 | 90 |
| 2-Pentanone | 7.2 | 2.7 | 86 | 36.0 | 232.2 | 6.4 | 36035 | 230.0352 | 3099 | |
| 2-Pentanol | 0 | 0 | 88 | 37.8 | 0 | 0.0 | 37841 | 0 | 3330 | 78 |
| 4-Heptanone | 10.9 | 11.6 | 114 | 35.3 | 1322.4 | 36.4 | 35333 | 1284.566 | 4028 | 78 |
| 4-heptanol | 11.3 | 12.6 | 116 | 40.0 | 1461.6 | 40.2 | 39974 | 1606.263 | 4637 | 78 |
| 2-heptanol | 11.5 | 3.7 | 116 | 40.0 | 429.2 | 11.8 | 39974 | 471.6803 | 4637 | |
| 3-Methyl cyclohexanol | 12.6 | 1.1 | 114 | 38.3 | 125.4 | 3.4 | 38263 | 131.9129 | 4362 | 83 |
| Total | | | | | 3637.4 | 100.0 | 263502 | 3790.521 | | |
| | | | | | | | Average Energy/Kg of fuel | | 37.90521 | |

Experiment 16

Hydrogenation of DHAA with a Ru-alumina catalyst: In the stainless steel inset was put 3.20 g of 2% Ru-alumina catalyst (Afa-Aesar) and 0.51 g of DHAA and the inset was placed inside of the reactor. The reactor was sealed and purged with argon and hydrogen three times each and then hydrogen filled to a pressure of 1100 psi. Heating was started and temperature of the catalyst bed was maintained at 200-220° C. for 3.3 hours. The pressure drop related to hydrogen consumption was observed and in the end of hydrogenation it was 900 psi. The reactor was cooled down, purged with argon, the inset was removed and the catalyst was washed with 5 mL of methyl acetate. The resulting wash was filtered and analyzed by GC/MS. GCMS qualitative analysis of products formed is shown in Table 15 and also presents a theoretical estimation of the calorific value of a mixture. 100% DHAA reacted. 41% was a mixture of higher alcohols and ketones of which 27.7% was higher alcohols and 23.4% of that was heptanols.

TABLE 15

Products in a Ru-alumina DHAA reduction at 200-220° C., 3.3 hrs mixture sample with an energy estimation of the same.

| Compound | GC Ret. Min. | GC Area % | Mol. Wt. | Δc liq. kJ/gm | Normlzd Wt. | Wt. Fractn. | Δc liq. kJ/Kg | Energy/ comp | NIST Δc liq. kJ/mol | Lib. Match Qual. |
|---|---|---|---|---|---|---|---|---|---|---|
| 1-Butanol | 7 | 0 | 74 | 36.1 | 0 | 0.0 | 36081 | 0 | 2670 | 90 |
| 2-Pentanone | 7.2 | 2.3 | 86 | 36.0 | 197.8 | 4.4 | 36035 | 157.6297 | 3099 | |
| 2-Pentanol | 7.5 | 4.3 | 88 | 37.8 | 378.4 | 8.4 | 37841 | 316.6659 | 3330 | 78 |

TABLE 15-continued

Products in a Ru-alumina DHAA reduction at 200-220° C., 3.3 hrs mixture sample with an energy estimation of the same.

| Compound | GC Ret. Min. | GC Area % | Mol. Wt. | Δc liq. kJ/gm | Normlzd Wt. | Wt. Fractn. | Δc liq. kJ/Kg | Energy/ comp | NIST Δc liq. kJ/mol | Lib. Match Qual. |
|---|---|---|---|---|---|---|---|---|---|---|
| 4-Heptanone | 10.8 | 10.8 | 114 | 35.3 | 1231.2 | 27.2 | 4042 | 962.0594 | 4028 | 78 |
| 4-heptanol | 11.2 | 17.7 | 116 | 40.0 | 2053.2 | 45.4 | 39974 | 1815.094 | 4637 | 78 |
| 2-heptanol | 11.4 | 5.7 | 116 | 40.0 | 661.2 | 14.6 | 39974 | 584.5217 | 4637 | |
| 3-Methyl cyclohexanol | 12.5 | 0 | 114 | 38.3 | 0 | | 38263 | 0 | 4362 | 83 |
| Total | | | | | 4521.8 | 100.0 | 232210 | 3835.97 | | |
| | | | | | | | Average Energy/Kg of fuel | 38.3597 | | |

Experiment 17

Hydrogenation of DHAA in dioxane over a copper-zinc catalyst: 8.5 g of Copper zinc catalyst tablets were loaded into the steel tube hydrogenation reactor. A stream of 5% hydrogen/95% argon was passed over the catalyst at 0.5 lit/min as the catalyst was heated at 175° C. After reducing for about 18 hours overnight, the reactor was cooled and the catalyst was poured into a porcelain dish at room temperature under an argon atmosphere in a glove bag. 600 mg of DHAA was suspended in 1.2 ml of dioxane and heated with a heat gun. The hot dioxane was immediately added to the catalyst beads to wet the beads, the DHAA began to fall out of solution as the catalyst cooled. The catalyst beads were poured back into the hydrogenation reactor and it was sealed and removed from the glove bag. The reactor was then purged thrice with argon, twice with hydrogen and then filled to 1000 psi. The reactor was heated with the temperature rising to 210° C. Hydrogen was refilled as it was absorbed by the reaction and pressure varied between 900 and 1220 psi. After 2.5 hours an ice bath was placed to cool the liquid sampling tube, heating switched off and a liquid sample collected. GCMS of the sample indicated peaks for 4-heptanone, 4-heptanol, 2-heptanol and 1-butanol in a ratio of 14.2:71.4:12.6:1.5 respectively. Other products like 2,6-dimethyl-4-heptanol, n-heptane and 2,6-dimethylheptane were observed as lesser products.

All DHAA starting material was consumed. GCMS qualitative analysis of higher alcohols formed is shown in Table 16 and also presents a theoretical estimation of the calorific value of a mixture. 27% of products included higher alcohols, ketone and alkane products. 23% was higher alcohols of which 21% was heptanols.

TABLE 16

Products in Cu—ZnO DHAA reduction mixture with an energy estimation of the same.

| Compound | GC Ret. Min. | GC Area % | Mol. Wt. | Δc liq. kJ/gm | Normlized Wt. | Wt. Fractn. | Δc liq. kJ/Kg | Energy/ comp | NIST Δc liq. kJ/mol | Lib. Match Qual. |
|---|---|---|---|---|---|---|---|---|---|---|
| 2-Butanol | 5.6 | 0 | 74 | 35.9 | 0 | 0.0 | 35946 | 0 | 2660 | 83% |
| Heptane | 6.5 | 0.4 | 100 | 48.2 | 40 | | 48170 | 0 | 4817 | 91 |
| 1-Butanol | 6.9 | 0.5 | 74 | 36.1 | 37 | 1.3 | 36081 | 45.300305 | 2670 | 90 |
| Pentanol | 7.5 | 0 | 88 | 37.8 | 0 | 0.0 | 37841 | 0 | 3330 | 78 |
| Hexanol | 8.7 | 0 | 102 | 39.1 | 0 | 0.0 | 39059 | 0 | 3984 | 90 |
| 2,6,-Dimethyl-heptane | 9.2 | 0.4 | 128 | 47.9 | 51.2 | | 47852 | 0 | 6125 | 80 |
| 4-Heptanone | 10.9 | 3.6 | 102 | 39.0 | 367.2 | 12.5 | 39000 | 485.94503 | 4028 | 78 |
| 4-heptanol | 11.3 | 18 | 116 | 40.0 | 2088 | 70.9 | 39974 | 2832.2362 | 4637 | 78 |
| 2-heptanol | 11.5 | 3.3 | 116 | 40.0 | 382.8 | 13.0 | 39974 | 519.2433 | 4637 | |
| Heptanol isomer (methylcyclo hexanol) | 12.5 | 0 | 114 | 38.3 | 0 | 0.0 | 38263 | 0 | 4362 | 83 |
| 2,6-Dimethyl-4-heptanol | 13.2 | 0.5 | 144 | 41.3 | 72 | 2.4 | 41292 | 100.88225 | 5946 | 74 |
| 2-Ethyl1-hexanol | 13.9 | 0.6 | 130 | 40.7 | 78 | 2.6 | 40723 | 107.78419 | 5294 | |
| Total | | | | | 2947 | 100.0 | 443451 | 3983.6071 | | |
| | | | | | | | Average Energy MJ/Kg of fuel | 39.83607 | | |

Experiment 18

Hydrogenation of DHAA over Cu—Cr for 3 hours: 13 g of a copper chromite barium promoted catalyst containing about 62-64% $Cr_2CuO_4$, 22-24% CuO, 6% BaO, 0-4% Graphite, 1% $CrO_3$, was weighed and added to the hydrogenation reactor described above. The reactor was sealed and a mixture of 5% hydrogen/95% nitrogen mixture was passed over the catalyst for about 18 hours at a temperature range of 155 to 180° C. The nitrogen/hydrogen gas mixture was replaced by a hydrogen gas stream and reduction was continued for another one hour at 180° C. The heating was shut off and system allowed to cool to room temperature. 0.5 g of DHAA was suspended in 1.5 ml of methanol and 1.5 ml of isopropanol and warmed gently with a heat gun until a clear solution was formed. The solution was quickly added to the catalyst bed and the reactor was sealed up. The reactor was pressurized with hydrogen at 1100 psi and was heated. Temperature rose to 271° C. and the pressure rose to 1170 psi. Heating was decreased and temperature fell to 224° C. $H_2$ pressure dropped to 970 psi over about one and half hour and was refilled to 1140 psi. After running for 3 hours the sampling tube was cooled, sample was taken and heating was shut off. GCMS of the sample indicated formation of 4-heptanol and n-heptane as major products in a ratio of 18.8:16.7 area percents respectively. Other alcohols such as 2-butanol, 1-butanol, 2-pentanol, etc and alkanes such as 3-methyl heptanes, 2,6-dimethyl heptanes, etc were observed in lesser amounts. All starting material was consumed. GCMS qualitative analysis of higher alcohols formed is shown in Table 17 and also presents a theoretical estimation of the calorific value of a mixture. 100% of DHAA was reacted. 63% of product mixture was observed to contain higher alcohols and alkanes. 32% were higher alcohols of which 17% was heptanols.

common line conveying liquid from the reservoir and hydrogen gas from the hydrogen supply line which had a mass flow controller and thermocouple. The bottom of the reactor was connected to a chilled condenser that condensed liquids that were drained under pressure, collected and analyzed. The uncondensed gases and vapors exited the condenser through a tube that was equipped with a back pressure regulator that was used to maintain reactor system pressure.

Experiment 19

Hydrogenation of DHAA over a copper chromite catalyst: The hydrogenation reactor was filled with 297 g of copper chromite barium hydroxide catalyst and reduced with 5% hydrogen 95% nitrogen overnight at 195° C. The reduction was continued by replacing the hydrogen/argon mixture with hydrogen for another two hours to ensure proper reduction. The reactor was heated to about 350° C. at the

TABLE 17

DHAA reduction over Cu—Cr catalyst mixture with an energy estimation of the sample.

| Compound | GC Ret. Min. | GC Area % | Mol. Wt. | Δc liq. kJ/gm | Normalzed Wt. | Wt. Fractn. | Δc liq. kJ/Kg | Energy/comp | NIST Δc liq. kJ/mol | Lib. Match Qual. |
|---|---|---|---|---|---|---|---|---|---|---|
| 2-Butanol | 5.6 | 1 | 74 | 35.9 | 74 | 1.0 | 35946 | 36.85436 | 2660 | 83% |
| Heptane | 6.5 | 18.8 | 100 | 48.2 | 1880 | 26.0 | 48170 | 1254.705 | 4817 | 91 |
| 1-Butanol | 6.9 | 1.7 | 74 | 36.1 | 125.8 | 1.7 | 36081 | 62.88794 | 2670 | 90 |
| Pentanol | 7.5 | 1.2 | 88 | 37.8 | 105.6 | 1.5 | 37841 | 55.36466 | 3330 | 78 |
| 3-methyl heptane | 8 | 3.2 | 114 | 48.0 | 364.8 | 5.1 | 47965 | 242.4296 | 5468 | 94 |
| 2,6,-Dimethyl-heptane | 9.2 | 5 | 128 | 47.9 | 640 | 8.9 | 47852 | 424.31 | 6125 | 80 |
| 4-methyl-2-pentanol | 8.7 | 5.9 | 102 | 39.1 | 601.8 | 8.3 | 39059 | 325.6706 | 3984 | 78 |
| 4-heptanol | 11.3 | 16.7 | 116 | 40.0 | 1937.2 | 26.8 | 39974 | 1072.904 | 4637 | 78 |
| 2-heptanol | 11.5 | 0 | 116 | 40.0 | 0 | 0.0 | 39974 | 0 | 4637 | |
| pent Diol | 12.4 | 0 | | | 0 | 0.0 | | 0 | | 91 |
| 3-methyl-4-heptanol | 12.7 | 1.9 | 130 | 40.7 | 247 | 3.4 | 40723 | 139.3621 | 5294 | 72 |
| 3-methyl-4-heptanol | 12.78 | 1.6 | 130 | 40.7 | 208 | 2.9 | 40723 | 117.3576 | 5294 | 83 |
| 2,6-Dimethyl decane | 13.7 | 4 | 170 | 47.6 | 680 | 9.4 | 47565 | 448.1268 | 8086 | 74 |
| 2,6,8-trimethyl-4-nonanol | 17 | 1.9 | 186 | 42.7 | 353.4 | 4.9 | 42742 | 209.2801 | 7950 | |
| Total | | | | | 7217.6 | 100.0 | 544614 | 4389.253 | | |
| | | | | | | | Average Energy MJ/Kg of fuel | 43.89253 | | |

Continuous flow Reactions. Reaction systems used (shown in FIG. 17) consisted of an upper liquid reservoir designed to melt any solid DHAA. It was made of stainless steel and fitted with a pressure transducer at the top, a tube connection to a helium cylinder to apply pressure and control flow of liquid and a tube at the bottom for liquid flow to the reactor chamber below. The reservoir was immersed in a heat bath equipped with heating oil, means for heating the bath and thermocouples to monitor the temperature. The reservoir bottom tube was a 0.02" ID tube connected to another tube leading into the steel pipe reactor equipped with four thermocouples along its length and a pressure transducer. The top of the reactor was connected to a mid section of the reactor and hydrogen and DHAA flow started. Table 18 below describes some temperatures, pressure and flow rates for the reaction. Seven samples collected weighing 151 g. Total DHAA feed was 297 g. Reaction parameters and products seen in GCMS are shown in Tables 18 and 19 respectively. 100% of DHAA was hydrogenated. 53% of product was observed to contain higher alcohols, alkanes and ketones. 30% was hydrocarbons, 9% was higher alcohols of which 6% was heptanols. Samples were collected and analyzed by GCMS. Table 20 below describes compounds seen in the GCMS qualitative analysis and gives an estimation of the calorific value of a product sample of the reaction.

TABLE 18

Reaction conditions in DHAA Cu—Cr cat. continuous flow reduction reaction.

| Time | Reactor pressure, psi | He pressure, psi | DHAA Flow rate, ml/min | H2 flow rate, l/min | DHAA Temp. °C. | Temp. Top, °C. | Temp. Mid, °C. | Temp bottom, °C. |
|---|---|---|---|---|---|---|---|---|
| 1:23 | 297 | 309 | 8 | 18 | 164 | 459 | 350 | 304 |
| 1:34 | 302 | 310 | 4 | 14 | 161 | 167 | 357 | 415 |
| 1:45 | 276 | 292 | 6 | 6 | 156 | 311 | 299 | 411 |
| | | | Run halted for hydrogen cylinder switch. | | | | | |
| 2:00 | 307 | 320 | 6 | 17 | 150 | 217 | 334 | 324 |
| 2:10 | 311 | 323 | 5.6 | 17.6 | 146 | 214 | 278 | 297 |
| 2:20 | 311 | 323 | 5.1 | 16.6 | 144 | 227 | 234 | 238 |
| 2:30 | 312 | 322 | 4.8 | 17 | 139 | 237 | 256 | 258 |

Calorific values of samples collected are S2-41.5 MJ/kg, S3-9.8 MJ/KG, S5-33.9 MJ/KG, S6-32.6 MJ/KG.

TABLE 19

Products seen in GCMS samples of DHAA Cu—Cr cat. continuous flow reduction Run 2 sample #2.

| Compound | Ret Time, min | CCMS Area % |
|---|---|---|
| Heptane | 6.51 | 16.46% |
| 2-Pentanone | 7.15 | 2.18% |
| 2 Methylheptane | 7.88 | 2.20% |
| Nonane | 10.59 | 4.45% |
| 4-Heptanone | 10.86 | 6.13% |
| 4-Heptanol | 11.23 | 6.06% |
| 4-Methylnonane | 11.78 | 4.91% |
| 4-Nonanone | 14.46 | 2.14% |
| 4-Nonanol | 14.76 | 2.90% |
| 4-Methylundecane | 15.18 | 2.84% |
| 2,6,10-Trimethylpentadecane | 16.04 | 2.42% |

52.7% of sample is shown here

TABLE 20

GCMS data of DHAA Cu—Cr hydrogenation run2 sample 2 products with estimation of calorific value of the mixture

| # of C's | Alcohols % by wt | Alcohols Net Energy MJ/KG | Alcohols weighted Net Energy MJ/KG | Alkanes % by wt | Alkanes Net Energy MJ/KG | Alkanes weighted Net Energy MJ/KG | Aromatics % by wt | Aromatics Net Energy MJ/KG | Aromatics weighted Net Energy MJ/KG | Ketones % by wt | Ketones Net Energy MJ/KG | Ketones weighted Net Energy MJ/KG |
|---|---|---|---|---|---|---|---|---|---|---|---|---|
| 1 | | | | | | | | | | | | |
| 2 | | | | | | | | | | | | |
| 3 | | | | | | | | | | | | |
| 4 | | | | | | | | | | | | |
| 5 | 1.84% | 37.80 | 0.69 | | | | | | | 0.70% | 36.00 | 0.25 |
| 6 | 1.11% | 39.10 | 0.43 | | | | | | | 0.44% | 37.45 | 0.16 |
| 7 | 7.16% | 41.08 | 2.94 | 15.79% | 48.17 | 7.61 | 0.64% | 42.10 | 0.27 | 7.67% | 39.00 | 2.99 |
| 8 | | | | 11.19% | 47.60 | 5.32 | 0.74% | 42.60 | 0.32 | 2.43% | 39.40 | 0.96 |
| 9 | 2.79% | 41.30 | 1.15 | 5.84% | 47.80 | 2.79 | 5.50% | 42.90 | 2.36 | 0.55% | 40.20 | 0.22 |
| 10 | | | | 8.21% | 47.70 | 3.92 | 6.16% | 42.30 | 2.61 | | | |
| 11 | | | | 1.91% | 47.60 | 0.91 | 4.87% | 41.50 | 2.02 | | | |
| 12 | | | | 4.22% | 47.50 | 2.01 | 3.38% | 41.50 | 1.40 | | | |
| 13 | | | | 0.83% | 47.40 | 0.39 | | | | | | |
| 14 | | | | 1.87% | 47.50 | 0.89 | | | | | | |
| 15 | | | | | | | | | | | | |
| 16 | | | | | | | | | | | | |
| 17 | | | | | | | | | | | | |
| 18 | | | | 0.97% | 45.89 | 0.44 | | | | | | |
| 19 | | | | | | | | | | | | |
| 20 | | | | | | | | | | | | |
| TOTAL | 12.89% | 40.49 | 5.22 | 50.84% | 47.77 | 24.28 | 21.30% | 42.15 | 8.98 | 11.79% | 38.90 | 4.59 |

| # of C's | MISC % by wt | MISC Net Energy MJ/KG | MISC weighted Net Energy MJ/KG | Phenols % by wt | Phenols Net Energy MJ/KG | Phenols weighted Net Energy MJ/KG | TOTAL % by wt | TOTAL Net Energy MJ/KG | TOTAL weighted Net Energy MJ/KG |
|---|---|---|---|---|---|---|---|---|---|
| 1 | | | | | | | | | |
| 2 | | | | | | | | | |
| 3 | | | | | | | | | |
| 4 | 0.25% | 28.84 | 0.07 | | | | 0.25% | 28.84 | 0.07 |

TABLE 20-continued

GCMS data of DHAA Cu—Cr hydrogenation run2 sample 2 products with estimation of calorific value of the mixture

|   |       |       |      |       |       |      |        |       |       |
|---|-------|-------|------|-------|-------|------|--------|-------|-------|
| 5 |       |       |      |       |       |      | 2.53%  | 37.31 | 0.94  |
| 6 |       |       |      |       |       |      | 1.55%  | 38.63 | 0.60  |
| 7 |       |       |      | 1.56% | 33.18 | 0.52 | 32.83% | 43.65 | 14.33 |
| 8 |       |       |      | 0.44% | 34.48 | 0.15 | 14.80% | 45.61 | 6.75  |
| 9 | 0.32% | 45.30 | 0.14 |       |       |      | 14.99% | 44.46 | 6.66  |
| 10 |      |       |      | 0.61% | 32.21 | 0.20 | 14.99% | 44.85 | 6.72  |
| 11 |      |       |      |       |       |      | 6.79%  | 43.22 | 2.93  |
| 12 |      |       |      |       |       |      | 7.61%  | 44.83 | 3.41  |
| 13 |      |       |      |       |       |      | 0.83%  | 47.40 | 0.39  |
| 14 |      |       |      |       |       |      | 1.87%  | 47.50 | 0.89  |
| 15 |      |       |      |       |       |      |        |       |       |
| 16 |      |       |      |       |       |      |        |       |       |
| 17 |      |       |      |       |       |      |        |       |       |
| 18 |      |       |      |       |       |      | 0.97%  | 45.89 | 0.44  |
| 19 |      |       |      |       |       |      |        |       |       |
| 20 |      |       |      |       |       |      |        |       |       |
| TOTAL | 0.57% | 38.01 | 0.21 | 2.62% | 33.17 | 0.87 | 100.0% | 44.15 | 44.15 |

Experiment 20

Hydrogenation of DHAA over a copper zinc catalyst: The reactor was filled with 544 g of copper zinc catalyst and reduced with 5% hydrogen 95% nitrogen overnight at 195° C. The reduction was continued by replacing the hydrogen/argon mixture with hydrogen for another two hours to ensure proper reduction. The reactor was heated to about 247° C. at the mid section of the reactor and hydrogen and DHAA flow started. Table 21 below describes some temperatures, pressure and flow rates for the reaction. Total product collected was 182 g. Samples were collected and analyzed by GCMS. Reaction parameters and products seen in GCMS are shown in Tables 21 and 22 respectively. Table 23 below describes compounds seen in the GCMS qualitative analysis and gives an estimation of the calorific value of a product sample of the reaction. 100% of DHAA was hydrogenated. 73% of product was observed to contain higher alcohols, alkanes and ketone products, 14% was higher alcohols.

Experimental calorific values of samples run gave S4 34.2 MJ/Kg, S8 34.5 MJ/Kg, S11 34.5 MJ/Kg.

| Compound | Ret Time, min | GCMS Area % |
|---|---|---|
| Heptane | 6.51 | 3.87% |
| 1-Butanol | 6.92 | 4.72% |
| 2-Pentanone | 7.18 | 6.48% |
| 2-Pentanol | 7.51 | 7.25% |
| 4-Heptanone | 10.89 | 16.14% |
| 2-Heptanone | 11.28 | 18.29% |
| 4-Propylheptane | 11.47 | 10.82% |
| 4-Nonanone | 14.47 | 3.40% |
| 4-Nonanol | 14.72 | 2.10% |

73.1% of sample is shown here

TABLE 21

Reaction parameters for Cu—Zn run 4 hydrogenation of DHAA

| Time | Reactor pressure psi | He pressure psi | DHAA Flow rate | H2 flow rate | DHAA Temp. ° C. | Temp. Top ° C. | Temp. Mid ° C. | Temp bottom ° C. |
|---|---|---|---|---|---|---|---|---|
| 1:51 | 305 | 311 | 3.1 | 12.2 | 138 | 200 | 247 | 219 |
| 2:03 | 304 | 311 | 3.6 | 18.2 | 142 | 195 | 236 | 220 |
| 2:14 | 303.6 | 308 | 3.0 | 20 | 142 | 201 | 262 | 314 |
| 2:24 | 301 | 306 | 3.0 | 20.8 | 141 | 213 | 243 | 373 |
| 2:37 | 302 | 307 | 3.0 | 16.8 | 137 | 234 | 299 | 345 |
| 2:48 | 299 | 292 | 3.0 | 17.4 | 138 | 261 | 385 | 356 |
| 2:58 | 300 | 306 | 3.1 | 17.2 | 141.9 | 241 | 332 | 351 |
| 3:09 | 297 | 303 | 3.1 | 16.4 | 140.9 | 259 | 369 | 353 |
| Hydrogen cylinder replaced. | | | | | | | | |
| 3:22 | 303.9 | 309 | 3.4 | 16.1 | 143 | 306 | 356 | 281 |
| 3:35 | 305 | 310 | 3.3 | 16.5 | 144 | 147 | 202 | 265 |
| 3:47 | 92 | 309 | −7 | 16.9 | 146 | 221 | 267 | 368 |

TABLE 22

Products in GCMS samples of DHAA Cu—Zn reduction experiment run 4 sample #8.

| | Alcohols | | | Alkanes | | | Aromatics | | | Ketones | | |
|---|---|---|---|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG |
| 1 | | | | | | | | | | | | |
| 2 | | | | | | | | | | | | |
| 3 | | | | | | | | | | | | |
| 4 | 4.46% | 36.00 | 1.61 | | | | | | | | | |
| 5 | | | | | | | | | | 6.71% | 36.00 | 2.42 |
| 6 | 0.80% | 39.10 | 0.31 | | | | | | | 1.33% | 37.45 | 0.50 |
| 7 | 1.75% | 41.08 | 0.72 | 6.99% | 48.17 | 3.37 | 0.33% | 42.10 | 0.14 | 16.45% | 39.00 | 6.42 |
| 8 | 1.30% | 40.70 | 0.53 | 0.59% | 47.60 | 0.28 | 0.34% | 42.60 | 0.14 | 1.42% | 39.40 | 0.56 |
| 9 | | | | 16.65% | 47.80 | 7.96 | 4.02% | 42.90 | 1.73 | | | |
| 10 | | | | 10.69% | 47.70 | 5.10 | 9.40% | 42.30 | 3.98 | | | |
| 11 | | | | | | | 3.13% | 41.50 | 1.30 | | | |
| 12 | | | | | | | | | | | | |
| 13 | | | | | | | | | | | | |
| 14 | | | | | | | | | | | | |
| 15 | | | | | | | | | | | | |
| 16 | | | | | | | | | | | | |
| 17 | | | | | | | | | | | | |
| 18 | | | | | | | | | | | | |
| 19 | | | | | | | | | | | | |
| TOTAL | 8.31% | 38.10 | 3.17 | 34.91% | 47.84 | 16.70 | 17.23% | 42.30 | 7.29 | 25.91% | 38.17 | 9.89 |

| | MISC | | | Phenols | | | TOTAL | | |
|---|---|---|---|---|---|---|---|---|---|
| # of C's | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG |
| 1 | | | | | | | | | |
| 2 | | | | | | | | | |
| 3 | | | | | | | | | |
| 4 | | | | | | | 4.46% | 36.00 | 1.61 |
| 5 | 7.71% | 32.82 | 2.53 | | | | 14.42% | 34.30 | 4.95 |
| 6 | 0.50% | 27.94 | 0.14 | | | | 2.63% | 36.14 | 0.95 |
| 7 | 1.64% | 47.53 | 0.78 | 0.49% | 33.18 | 0.16 | 27.65% | 41.89 | 11.58 |
| 8 | 0.75% | 35.24 | 0.27 | 1.69% | 34.39 | 0.58 | 6.08% | 38.74 | 2.35 |
| 9 | | | | 0.86% | 36.66 | 0.32 | 21.54% | 46.44 | 10.00 |
| 10 | | | | | | | 20.09% | 45.17 | 9.07 |
| 11 | | | | | | | 3.13% | 41.50 | 1.30 |
| 12 | | | | | | | | | |
| 13 | | | | | | | | | |
| 14 | | | | | | | | | |
| 15 | | | | | | | | | |
| 16 | | | | | | | | | |
| 17 | | | | | | | | | |
| 18 | | | | | | | | | |
| 19 | | | | | | | | | |
| TOTAL | 10.60% | 35.04 | 3.71 | 3.04% | 34.84 | 1.06 | 100.0% | 41.82 | 41.82 |

Experiment 21

Hydrogenation of DHAA over a copper zinc catalyst at lower DHAA flow rates: The reactor was filled with 580 g of copper zinc catalyst and reduced with 5% hydrogen 95% nitrogen overnight at 195° C. The reduction was continued by replacing the hydrogen/argon mixture with hydrogen for another two hours to ensure proper reduction. The reactor was heated to about 300° C. at the mid section of the reactor and hydrogen and DHAA flow started. Table 24 below describes some temperatures, pressure and flow rates for the reaction. 301 g of DHAA was reacted. Sixteen liquid samples were collected over the reaction amounting to 117 g of product collected. Samples were collected and analyzed by GCMS. Reaction parameters and products seen in GCMS are shown in Tables 24 and 25 respectively and graph 1 below. Table 26 below describes compounds seen in the GCMS qualitative analysis and gives an estimation of the calorific value of a product sample of the reaction. 100% of DHAA was converted. 75% of product included hydrocarbons and 2% of 4-nonanol. Graph 1 shows composition change of the mixture of the formed products with time and temperature.

TABLE 24

Reaction conditions for DHAA Cu—ZnO hydrogenation run 11 as flow of DHAA was varied.

| Time | Reactor pressure psi | He pressure psi | DHAA Flow rate | H₂ flow rate | DHAA Temp. °C. | Temp. Top °C. | Temp. Mid °C. | Temp bottom °C. |
|---|---|---|---|---|---|---|---|---|
| 1:40 | 300 | 308 | 2.3 | 21.3 | 151 | 216 | 298 | 309 |
| 1:50 | 304 | 311 | 1.8 | 19.8 | 150 | 218 | 354 | 383 |
| 2:00 | 306 | 311 | 1.9 | 20.8 | 150 | 219 | 360 | 361 |
| 2:10 | 306 | 311 | 1.2 | 21.6 | 148 | 216 | 336 | 379 |
| 2:20 | 308 | 314 | 2.0 | 22.1 | 147 | 220 | 276 | 327 |
| 2:30 | 306 | 311 | 1.6 | 20.2 | 147 | 233 | 329 | 311 |
| 2:40 | 302 | 306 | 2.1 | 19.3 | 146 | 224 | 416 | 309 |
| 2:50 | 303 | 308 | 1.9 | 20.0 | 144 | 219 | 434 | 304 |
| 3:00 | 299 | 306 | 2.2 | 27.6 | 145 | 189 | 400 | 315 |
| 3:10 | 302 | 308 | 2.1 | 27.9 | 145 | 139 | 283 | 342 |
| 3:20 | 300 | 308 | 2.6 | 23.1 | 144 | 167 | 311 | 349 |
| 3:30 | 298 | 303 | 1.9 | 22.4 | 144 | 210 | 294 | 301 |
| 3:40 | 299 | 303 | 1.8 | 19.8 | 145 | 249 | 334 | 267 |
| 3:50 | 299 | 301 | 1.4 | 20.6 | 145 | 254 | 347 | 287 |
| 4:00 | 299 | 304 | 1.2 | 20.6 | 145 | 218 | 311 | 295 |

TABLE 26

GCMS data of DHAA Cu—Zn hydrogenation run 11 sample 1 products with estimation of calorific value of th emixture

| # of C's | Alcohols | | | Alkanes | | | Aromatics | | | Ketones |
|---|---|---|---|---|---|---|---|---|---|---|
| | % by wt | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG | % by wt |
| 1 | | | | | | | | | | |
| 2 | | | | | | | | | | |
| 3 | | | | | | | | | | |
| 4 | | | | | | | | | | |
| 5 | 0.24% | 37.80 | 0.09 | | | | | | | |
| 6 | | | | | | | 0.29% | 41.90 | 0.12 | |
| 7 | | | | 38.85% | 48.17 | 18.71 | 0.65% | 42.10 | 0.28 | 1.17% |
| 8 | | | | 17.34% | 47.60 | 8.25 | | | | |
| 9 | 2.32% | 41.30 | 0.96 | 11.66% | 47.80 | 5.58 | 2.55% | 42.90 | 1.09 | 1.53% |
| 10 | | | | 8.46% | 47.70 | 4.03 | 4.14% | 42.30 | 1.75 | |
| 11 | | | | 0.37% | 47.60 | 0.17 | 1.80% | 41.50 | 0.75 | |
| 12 | | | | 2.75% | 47.50 | 1.31 | 0.44% | 41.50 | 0.18 | |
| 13 | | | | | | | | | | |
| 14 | | | | 1.13% | 47.50 | 0.54 | | | | |
| 15 | | | | | | | | | | |
| 16 | | | | | | | | | | |
| 17 | | | | | | | | | | |
| 18 | | | | | | | | | | |
| 19 | | | | | | | | | | |
| 20 | | | | | | | | | | |
| TOTAL | 2.56% | 40.97 | 1.05 | 80.55% | 47.91 | 38.59 | 9.89% | 42.25 | 4.18 | 2.70% |

| # of C's | Ketones | | MISC | | | TOTAL | | |
|---|---|---|---|---|---|---|---|---|
| | Net Energy MJ/KG | weighted Net Energy MJ/KG | % by wt | Net Energy MJ/KG | weighted Net Energy MJ/KG | % by wt | Net Energy MJ/KG | weighted Net Energy MJ/KG |
| 1 | | | | | | | | |
| 2 | | | | | | | | |
| 3 | | | | | | | | |
| 4 | | | 0.25% | 28.84 | 0.07 | 0.25% | 28.84 | 0.07 |
| 5 | | | 1.47% | 38.78 | 0.57 | 1.71% | 38.64 | 0.66 |
| 6 | | | 0.33% | 27.94 | 0.09 | 0.62% | 34.54 | 0.21 |
| 7 | 39.00 | 0.46 | | | | 40.68% | 47.81 | 19.45 |
| 8 | | | 1.23% | 38.32 | 0.47 | 18.57% | 46.99 | 8.72 |
| 9 | 40.20 | 0.61 | 1.03% | 45.30 | 0.46 | 19.09% | 45.61 | 8.71 |
| 10 | | | | | | 12.60% | 45.92 | 5.79 |
| 11 | | | | | | 2.17% | 42.53 | 0.92 |
| 12 | | | | | | 3.19% | 46.67 | 1.49 |
| 13 | | | | | | | | |

TABLE 26-continued

GCMS data of DHAA Cu—Zn hydrogenation run 11 sample 1
products with estimation of calorific value of th emixture

| | | | | | | | | |
|---|---|---|---|---|---|---|---|---|
| 14 | | | | | | 1.13% | 47.50 | 0.54 |
| 15 | | | | | | | | |
| 16 | | | | | | | | |
| 17 | | | | | | | | |
| 18 | | | | | | | | |
| 19 | | | | | | | | |
| 20 | | | | | | | | |
| TOTAL | 39.68 | 1.07 | 4.30% | 38.81 | 1.67 | 100.0% | 46.56 | 46.56 |

TABLE 25

Products seen in GCMS samples of
DHAA reduction run 11 sample #1

| Compound | Ret Time, min | GCMS area % |
|---|---|---|
| Heptane | 6.51 | 37.80% |
| 2-Methylheptane | 7.87 | 2.51% |
| 3-Methylheptane | 8.04 | 6.87% |
| Ethylcyclohexane | 9.48 | 2.90% |
| 3-Ethylheptane | 10.03 | 3.25% |
| Nonane | 10.57 | 7.51% |
| 4-Propylheptane | 11.46 | 3.12% |
| 4-Methylnonane | 11.77 | 3.47% |
| 6-Methyltridecane | 13.34 | 2.82% |
| Undecane | 14.17 | 2.60% |
| 4-Nonanol | 14.74 | 2.30% |

Butyric Acid Ketonization and Hydrogenation:

Experiment 22

Ketonization of butyric acid over gamma-alumina in a continuous flow reactor: Ketonization and Hydrogenation Reactor system setup: The ketonization reaction was performed in a steel tube reactor (made from Swagelok parts) consisting of a ½" diameter stainless steel tube fitted with a ball valve at the bottom and a ¼" union stainless steel cross on the top. A thermocouple was attached to the top arm of the cross with one of the (cross) side arms bearing a pressure gauge, pressure relief valve and a ball valve. The other side arm of the ¼" union cross was connected to a 1/16" tube which was attached to a Gilson 307 HPLC pump. The 1/16" tube entered the reactor and extended down till it was just above the catalyst bed. The bottom arm of the cross was attached to the top of the ½" stainless steel tube. The tube was wrapped with heating rope and insulation was wrapped around the heating rope. Another thermocouple was placed under the heating rope. Both the thermocouples were connected to a digital display. The ball valve on the bottom of the reactor is connected to a coil of ⅛" stainless steel tube that was connected to 2" length of ¼ inch tube with a drain at its bottom for liquid condensate and a vent near its top that carried out non-condensing gases. This coiled tube and lower portion are cooled with ice water and served as a trap to collect liquid. The end of the gas vent had a ball valve and the liquid collecting end had a needle valve so that it could be opened slowly to collect liquid samples.

4.1 g of gamma-alumina was loaded into the reactor and three different runs were done for the ketonization.

Run a) The reactor was heated to 350° C. The HPLC pump was turned on and butyric acid was pumped at a rate of 0.25 ml/min After the reaction had run for 15 minutes liquid samples were drawn. GCMS of the samples indicated formation of 6.5% 4-heptanone with 80% butyric acid remaining indicating a conversion of about 7.5% by GCMS.

Run b) The experiment was run with the flow rate of butyric acid decreased to 0.1 ml/min from 0.25 ml/min with temperature raised to 420 to 460° C. GCMS samples indicated 49% heptanone and 40% butyric acid indicating a conversion of about 55%.

Run c) The experiment was run with a flow rate of 0.05 ml/min, the temperatures ranged from 410 to 460° C. Samples of the reaction were collected. GCMS analysis of the product indicated 72.5% 4-heptanone was formed and 5.4% butyric remained indicating a conversion of about 93%.

Results are summarized in the Table 26 below:

TABLE 27

Heptanone product vs butyric acid starting material
GCMS analysis as flow rate is varied.

| Exp. No. | Reaction Temp. ° C. | Butyric acid flow rate ml/mm | 4-Heptanone Area % | Butyric acid Area % | Conversion |
|---|---|---|---|---|---|
| Run a | 350 | 0.25 | 6.5 | 80 | 7.5 |
| Run b | 420-460 | 0.10 | 49 | 40 | 55 |
| Run c | 410-460 | 0.05 | 72.5 | 5.4 | 93 |

Reduction of 4-heptanone to 4-heptanol:

Experiment 23

Reduction of 4-Heptanone to 4-heptanol over a copper-zinc catalyst in a continuous flow reactor: The reduction reaction was performed in a hydrogenation reactor (FIG. 14) (made from Swagelok parts using the required unions, port connectors, reducers and valves as needed) consisting of a ½" diameter stainless steel tube reactor wrapped in heat tape and insulation fitted with a ball valve at the bottom and a cross on the top. A thermocouple 6 was attached to the top arm of the cross. One of the side arms was connected to a pressure gauge 5, pressure relief valve and a ball valve to feed hydrogen to the reactor. To control the flow rate of hydrogen, the ball valve was connected via 5 foot length of fine 0.005" id tubing 3 connected by additional flexible tubing to a pressure gauge and a hydrogen cylinder. A 1/16" tube for liquid feed to a Gilson 307 HPLC pump was fed from a reactant reservoir. The 1/16" tube entered the reactor and extended down until it was just above the catalyst bed. The bottom arm of the cross union was attached to the top of the ½" stainless steel reactor tube. The tube was wrapped with heating rope and insulation was wrapped around the heating rope. Another thermocouple was placed under the heating rope. Both the thermocouples were connected to a digital display. The ball valve on the bottom of the reactor is connected to a coil of ⅛" stainless steel tube 7 that was connected to short length of ¼ inch tube with a drain at its bottom for liquid condensate and a vent near its top that carried out non-condensing gases. This coiled tube and lower portion are cooled with ice water and served as a trap to collect liquid. The end of the gas vent coming out of the top of the trap had a back pressure valve to control reactor pressure and maintain the required flow rate of hydrogen through the reactor which was calibrated for flow rates at different pressures before the reaction. The liquid collecting vent tube coming out of the bottom of the trap had a needle valve so that it could be opened slowly to collect liquid samples.

Procedure: The reactor tube was filled with about 13 g of zinc copper oxide catalyst (Unicat MTS401) and the catalyst reduced in 95:5 $N_2$/hydrogen stream at 0.2 liters/min overnight at a temperature of 180° C. The $N_2$/hydrogen mixture was replaced by a hydrogen line and reduction continued for another hour and then stopped. The reactor pressure was set to 300 psi hydrogen with temperature at 175° C. Hydrogen flow was at 400 cc/min and the HPLC pump was started, pumping 4-heptanone at a rate of 0.2 ml/min. Reaction was continued for about 90 minutes at this flow rate as samples were taken and analyzed by GCMS indicating 83.7% heptanol and 9.2% heptanone remaining (~90% conversion by GCMS). Flow rate of 4-heptanone was lowered to 0.15 ml/min as temperature, reactor pressure and hydrogen flow rate were in the range of 180-190° C., 300 psi and 400 cc/min respectively. GCMS at the lower flow rate indicated 77.8% 4-heptanol and 5.3% heptanone which is about 93% conversion by GC. A total of 22 grams of 4-heptanone were pumped through the reactor and 20 g of liquid product mixture was collected.

Experiment 24

Synthesis of Hydrocarbons from butyric acid on larger scale-reactor setup: A reaction system (shown in FIG. 18) consisting of two steel pipes, reactor 1 (R1) and reactor 2 (R2) connected in series was built to prepare heptane, 4-heptanol, and 4-heptanone. The first reactor R1, contained catalyst to ketonize butyric acid and pass the resulting product containing heptanone to the second reactor R2 containing catalyst which reduced 4-heptanone to form 4-heptanol, heptane, etc. R1 was made of a 1" diameter ASA schedule 40 pipe, 12 inches in length having connections for thermocouples (6, 7, 8, 9) on its side that measured catalyst bed temperatures along with a pressure transducer (5). The top of the tube was connected to a ⅛ inch tube which fed butyric acid onto the catalyst bed. The ⅛" tube was connected via a 1/16 inch tube (3) to a steel bottle containing butyric acid under a pressure using differential pressure transducer (4) used to deliver butyric acid a different rates. The bottom of the tube R1 was connected via a ¼" inch tube to R2 which was ASA schedule 40 about 13 inches in length and diameter of 1.5 inches having connections for thermo-couples (14, 15, 16, 17, 18, 19) on its side that measured catalyst bed temperatures along with a pressure transducer (13). A hydrogen line with a 0.09" orfice (10) connected to flow controller (11) entered R2 at the top. The bottom of R2 was connected to a trap that condensed the liquid products of the reactors and conveyed the gaseous products out to a vent. The trap was cooled by circulating chilled liquid and contained an outlet at the bottom that was connected to a ball valve and needle valve in series so that liquid samples could be drawn off slowly. The gas outlet from the trap was connected to a back pressure valve (21) so that reactor pressure could be set at 300 psi or other pressures as desired. A gas flow meter (22) was added down stream from back pressure control valve (21). Reactor R1 was filled with 80 g of gamma-alumina and R2 was filled with 570 g of copper zinc oxide catalyst (MTS-401 Unicat). The catalyst bed in R2 was heated to 180° C. and a stream of 5% hydrogen in nitrogen was passed over the catalyst for about 16 hours to reduce it. Pure hydrogen was passed for an additional hour to complete reduction.

Reactions were run as butyric acid was fed into R1 at 1 ml/min and after ketonization occurred the output of R1 was fed along with hydrogen flow rates at 4 SLPM through R2. Reactor pressure was at around 300 psi and temperature was raised. Samples of the reaction were drawn and analyzed by GCMS.

Five experiments were run with typically more than 25 samples for each run. Thus more than 125 samples were taken. For instance, data from run 3 was charted in graph 2 below showing product composition of samples as the temperature changed and experiment progressed over time. Table 28 shows an example of deeper analysis of data points from graph 4 for sample 30 taken at around 15:14 on the x-axis. GCMS qualitative analysis shows the important compounds found in sample 30 listed along with their percentage. 100% of starting materials were converted. Product mixture shows above 95% hydrocarbons of which 72.5% is heptane and minor ketone products. Table 29 lists experimental calorific values of samples from different runs.

Table 30 shows a theoretical energy calculation for the same sample 30 based on GCMS qualitative analysis. The table shows distribution of classes of compounds in the sample such as alcohols (such as 1-butanol, 4-heptanol, etc), ketones (such as 4-heptanone), alkanes (such as heptane, nonane, etc).

TABLE 28

GCMS data of products in run 3 sample 30 of butyric acid Ketonization-hydrogenation reaction.

| GC Ret. Time | Compound | Area % |
|---|---|---|
| 6.50 | Heptane | 72.5% |
| 7.90 | 4-Methylheptane | 1.3% |
| 8.03 | 3-Methylheptane, | 4.8% |
| 8.56 | Octene | 0.54% |
| 9.41 | Acetylacetone | 0.54% |
| 10.03 | 3-Ethylheptane | 1.1% |
| 10.56 | Nonane | 1.8% |
| 11.46 | 4-Propylheptane | 4.0% |
| 13.13 | 2,4-Heptanedione | 0.54% |
| 13.33 | Tridecane, 6-methyl- | 9.9% |

TABLE 29

Butyric acid ketonization-hydrogenation reaction experimental calorific values of samples, composition and calculated values

| Expt. Run No. and Sample No. | Avg. of Top Three Temps. ° C. | Sample weight gms. | Alcohols Area % | Alkanes Area % | Ketones Area % | Aromatics Area % | Estimated Calorific Value KJ/Kg | Experimental Calorific Value KJ/Kg |
|---|---|---|---|---|---|---|---|---|
| BR01 S05 | 222 | 4.1 gm | 28.54 | 4.55 | 24.4 | — | 32,330 | 26,484 |

TABLE 29-continued

Butyric acid ketonization-hydrogenation reaction experimental calorific values of samples, composition and calculated values

| Expt. Run No. and Sample No. | Avg. of Top Three Temps. ° C. | Sample weight gms. | Alcohols Area % | Alkanes Area % | Ketones Area % | Aromatics Area % | Estimated Calorific Value KJ/Kg | Experimental Calorific Value KJ/Kg |
|---|---|---|---|---|---|---|---|---|
| BR 01 S09 | 281 | 8.8 gm | 45.87 | 24.23 | 15.8 | 1.14 | 37,570 | 35,766 |
| BR 02 S17 | 305 | 4.1 gm | 40.22 | 31.44 | 18.4 | — | 38,400 | 36,196 |
| BR 02 S23 | 317 | 1.3 gm | 14.82 | 63.48 | 12.4 | 4.01 | 41,590 | 40.524 |
| BR 03 S07 | 251 | 9.4 gm | 57.00 | 7.56 | 17.2 | 8.18 | 36,710 | 35,494 |
| BR 04 S05 | 184 | 8.3 gm | 28.97 | 4.55 | 26.34 | 33.88 | 37,870 | 30,580 |
| BR 04 S07 | 244 | 20.9 gm | 54.59 | 3.99 | 30.4 | — | 36,420 | 34,052 |
| BR 05 S07 | 155 | 3.50 gm | 7.79 | 8.73 | 68.9 | — | 36,850 | 37,100 |
| BR 05 S13 | 254 | 9.40 gm | 24.49 | 6.41 | 56.8 | 0.67 | 35,930 | 30,108 |
| BR 05 S15 | 308 | 10.1 gm | 18.33 | 22.43 | 51.7 | — | 37,650 | 35,977 |

| | Ketones | | | Alcohols | | | Alkanes | | |
|---|---|---|---|---|---|---|---|---|---|
| # of C's | % by wt | Net Energy KJ/KG | weighted Net Energy KJ/KG | % by wt | Net Energy KJ/KG | weighted Net Energy KJ/KG | % by wt | Net Energy KJ/KG | weighted Net Energy KJ/KG |
| ? | | | | | | | | | |
| 1 | | | | | | | | | |
| 2 | | | | | | | | | |
| 3 | | | | | | | | | |
| 4 | | | | 0.06% | 36.00 | 0.02 | | | |
| 5 | 0.45% | 36.00 | 0.16 | | | | | | |
| 6 | | | | | | | | | |
| 7 | 0.57% | 39.10 | 0.22 | | | | 60.18% | 48.20 | 29.01 |
| 8 | | | | | | | 6.32% | 47.60 | 3.01 |
| 9 | | | | 0.30% | 41.32 | 0.12 | 3.23% | 47..8 | 1.54 |
| 10 | | | | | | | 4.96% | 47.70 | 2.37 |
| 11 | | | | | | | 0.29% | 47.60 | 0.14 |
| 12 | | | | | | | | | |
| 13 | | | | | | | 0.20% | 46.11 | 0.09 |
| 14 | | | | | | | 16.17% | 46.05 | 7.45 |
| 15 | | | | | | | | | |
| 16 | | | | | | | | | |
| 17 | | | | | | | | | |
| 18 | | | | | | | | | |
| 19 | | | | | | | | | |
| 20 | | | | | | | | | |
| TOTAL | 1.02% | 37.55 | 0.39 | 0.36% | 38.66 | 0.15 | 91.36% | 47.21 | 43.60 |

| | Phenols | | | Acid | | | TOTAL | | |
|---|---|---|---|---|---|---|---|---|---|
| # of C's | % by wt | Net Energy KJ/KG | weighted Net Energy KJ/KG | % by wt | Net Energy KJ/KG | weighted Net Energy KJ/KG | % by wt | Net Energy KJ/KG | weighted Energy KJ/KG |
| ? | | | | | | | 0.9% | 35.00 | 0.32 |
| 1 | | | | | | | | | |
| 2 | | | | | | | | | |
| 3 | | | | | | | | | |
| 4 | | | | 5.51% | 24.80 | 1.37 | 5.6% | 30.40 | 1.69 |
| 5 | | | | | | | 0.5% | 36.00 | 0.16 |
| 6 | | | | | | | | | |
| 7 | | | | | | | 60.8% | 43.65 | 26.52 |
| 8 | 0.48% | 35.50 | 0.17 | | | | 7.0% | 27.70 | 1.93 |
| 9 | | | | | | | 3.5% | 41.32 | 1.46 |
| 10 | | | | | | | 5.2% | 44.18 | 2.28 |
| 11 | | | | | | | 0.3% | 47.60 | 0.14 |
| 12 | | | | | | | | | |

-continued

|  |  |  |  |  |  |  |  |  |
|---|---|---|---|---|---|---|---|---|
| 13 |  |  |  |  |  | 0.2% | 46.11 | 0.09 |
| 14 |  |  |  |  |  | 16.2% | 46.05 | 7.45 |
| 15 |  |  |  |  |  |  |  |  |
| 16 |  |  |  |  |  |  |  |  |
| 17 |  |  |  |  |  |  |  |  |
| 18 |  |  |  |  |  |  |  |  |
| 19 |  |  |  |  |  |  |  |  |
| 20 |  |  |  |  |  |  |  |  |
| TOTAL | 0.48% | 35.50 | 0.17 | 5.51% | 24.80 | 1.37 | 100% | 40.33 | 42.04 |

Experiment 25

Lab scale synthesis of Methyl Ketene: The reactor system (FIG. 16 in drawings) was installed inside of a good working fume hood. The feed stream of propanoic anhydride vapor was generated by addition of the anhydride from the dropping funnel 1 into the hot round bottom flask 2 immersed in an oil bath 3. The resulting vapor was passed to the top of a vertical hollow quartz tube 4 47 cm long and with an internal diameter of 22 mm. At the lower part of the quartz tube (5 cm from the bottom) was placed a removable silica foam monolith disk 6 with porosity 45 pores per inch, 20 mm diameter and 10 mm thickness. The disk was supported inside of the reactor by a built-in quartz frit and temperature of the disk was measured with an external thermocouple placed in a glass pocket located under the frit. The quartz tube was placed in a cylindrical furnace 5 where the temperature was controlled with a PID controller 7. The gaseous products produced from the quartz tube were passed through a reflux condenser 8 with cold water (5° C.) to separate the formed methylketene from propanoic acid and anhydride which were collected by a graduated cylinder 9 attached at the bottom receiver for liquid condensate. The top of the reflux condenser was connected to the Dewar condenser 10 equipped with a round bottom flask 11, immersed in a Dewar flask 12. The flask was connected to the second Dewar condenser 13 also equipped with a round bottom flask 14 and immersed in a Dewar flask 15. The flask 14 was connect to the empty bubbler 16 which was attached to a vacuum pump 17 with the outlet tube placed into the hood's exhausting vent. The furnace temperature was set to 650° C. and temperature of the silica foam disk 6 in the reactor was kept at 550-580° C. The dropping funnel was charged with 100 mL of propionic anhydride and the vacuum pump was turned on to maintain ~80 mbar pressure in the reactor system. The first Dewar condenser 10 and Dewar flask 12 were filled with liquid nitrogen and then the anhydride was added at rate of ~0.8 ml/min to the flask 2 immersed in an oil bath heated at 180-200° C. The process was continued for 2 h and the product was collected in the flask 11. After the process was stopped, the connection between the first Dewar condenser 10 and a reflux condenser 8 was blocked (by pinching a connecting tubing) and the second Dewar condenser 13 and Dewar flask 15 were filled up with liquid nitrogen. Dewar flask 12 was removed and the round bottom flask 11 with attached Dewar condenser 10 was slowly warmed up to room temperature to distill part of the collected methylketene into the second Dewar condenser 13 and round bottom flask 14. After 1 h the connection between flask 11 and Dewar condenser 13 was blocked and the flask was disconnected and protected with a balloon filled with nitrogen and left overnight. The bubbler 16 was filled with 50 ml of acetone including a few drops of triethylamine. The second Dewar flask 15 was removed and the round bottom flask 14 with attached Dewar condenser 13 was slowly warmed up to room temperature. After 1 h the flask 14 was disconnected, protected with a balloon filled with nitrogen and left overnight. In the flask 11 was obtained 10 g of the yellow liquid including: 10.4% of methylketene dimer, 51.4% of methylketene trimer, 5.0% propionic acid and 7.4% of propionic acid anhydride (Mixture A). In the flask 14 was obtained 4 g of the yellow liquid including 8.6% of methylketene dimer, 69.5% of methylketene trimer and 7.9% of propionic acid anhydride (Mixture B). The acetone solution in the bubbler 16 showed the presence of triethylamine and only traces of methylketene dimer and propionic anhydride.

Experiment 26

Hydrogenation of methylketene dimer and trimer over a copper-zinc catalyst: The reduction reaction was performed in a hydrogenation reactor (FIG. 14) (made from Swagelok parts using the required unions, port connectors, reducers and valves as needed) consisting of a ½" diameter stainless steel tube reactor wrapped in heat tape and insulation fitted with a ball valve at the bottom and a cross on the top. A thermocouple 6 was attached to the top arm of the cross. One of the side arms was connected to a pressure gauge 5, pressure relief valve and a ball valve to feed hydrogen to the reactor. To control the flow rate of hydrogen, the ball valve was connected via 5 foot length of fine 0.005" id tubing 3 connected by additional flexible tubing to a pressure gauge and a hydrogen cylinder. A 1/16" tube for liquid feed to a Gilson 307 HPLC pump was fed from a reactant reservoir. The 1/16" tube entered the reactor and extended down till it was just above the catalyst bed. The bottom arm of the cross union was attached to the top of the ½" stainless steel reactor tube. The tube was wrapped with heating rope and insulation was wrapped around the heating rope. Another thermocouple was placed under the heating rope. Both the thermocouples were connected to a digital display. The ball valve on the bottom of the reactor is connected to a coil of ⅛" stainless steel tube 7 that was connected to short length of ¼ inch tube with a drain at its bottom for liquid condensate and a vent near its top that carried out non-condensing gases. This coiled tube and lower portion are cooled with ice water and served as a trap to collect liquid. The end of the gas vent coming out of the top of the trap had a back pressure valve to control reactor pressure and maintain the required flow rate of hydrogen through the reactor which was calibrated for flow rates at different pressures before the reaction. The liquid collecting vent tube coming out of the bottom of the trap had a needle valve so that it could be opened slowly to collect liquid samples.

Procedure: The reactor tube was filled with 8.9 g of copper zinc oxide catalyst (Unicat MTS401) and the catalyst was reduced in 95:5 $N_2$/hydrogen stream at 0.2 liters/min at a temperature of 160° C. for 18 h. The N₂/hydrogen mixture was replaced by a hydrogen line and reduction was continued for another hour at 0.4 liters/min at 200° C. Then the reactor pressure was set to 300 psi hydrogen with temperature at 183° C. and hydrogen flow at 400 cc/min. The HPLC pump was turned on and the Mixture A (from the methyl ketene reaction above) was pumped into the reactor at rate of 0.05 ml/min After 30 min hydrogen flow rate was increased to 660 cc/min and temperature of the reactor to 211° C. and the liquid samples were collected. GCMS analysis for product taken over duration of reaction indicated formation of 2-methylpentanol, 3-pentanol, pentanone, as two major products of the hydrogenation along with 3-pentanone (6%) and other higher alcohols presented in smaller amounts. GCMS qualitative analysis of higher alcohols formed is shown in Table 31. 100% of the methyl ketene dimer/trimer mixture was reduced. 43-50% higher alcohol product was formed of which 16-27% was 3-pentanola and 19-28% was 2-methyl pentanol.

TABLE 31

GCMS product analysis of samples from hydrogenation of methyl ketene dimer.

| Compound | GCMS ret Time (min) | GCMS Area % | | | |
|---|---|---|---|---|---|
| | | S1 | S3 | S5 | S8 |
| 3-Pentanone | 7.3 | 5.7 | 5.8 | 6.1 | 6.4 |
| 3-Pentanol | 7.4 | 27.0 | 18.3 | 16.5 | 15.6 |
| 2-Methyl-3-pentanol | 8.9 | 6.5 | 4.8 | 4.4 | 3.9 |
| Propyl propionate | 9.3 | 4.1 | 5.8 | 6.9 | 6.5 |
| 2-Methyl-1-pentanol | 10.2 | 12.2 | 23.1 | 22.6 | 19.7 |
| 4-Methyl-3-heptanone | 11.9 | 2.0 | 2.3 | 2.6 | 2.7 |
| 4-Methyl-3-heptanol | 12.6 | 2.3 | 2.2 | 2.3 | 2.0 |
| 4-Methyl-3-heptanol | 12.63 | 1.5 | 1.9 | 1.8 | 1.7 |
| 2-Methyl-1-pentyl propanoate | 13.9 | 1.9 | 2.2 | 2.8 | 3.1 |
| 3,5-Dimethyl furanone deriv. | 14.0 | 1.4 | 2.1 | 2.1 | 2.0 |
| 3,5-Dimethyl dihydrofuranone deriv. | 14.2 | 1.4 | 1.5 | 1.4 | 1.4 |
| 3,5-Dimethyl dihydrofuranone deriv. | 14.3 | | 2.2 | 1.9 | 2.7 |
| Propyl 3-hydroxy-2-methyl pentanoate | 16.4 | 1.3 | 0.9 | 1.3 | 1.6 |
| Propyl 3-hydroxy-2-methyl pentanoate | 16.6 | 1.3 | 1.0 | 1.3 | 1.6 |

Experiment 27

Conversion of propanoic acid to 3-pentanol via ketonization and reduction: The continuous flow reactor system (FIG. 18) was installed inside of a good working walk-in-hood. In the liquid reservoir was placed 292 g (300 ml) of propanoic acid. In the reactor 1 (ketonization step) was placed 220 g of gamma-alumina (bed of diameter 1.6" and length 13.0") and in the reactor 2 (reduction step) was placed 570 g copper-zinc oxide catalyst (bed of diameter 1.6" and length 12.4"). Temperature of the reactors 1 and 2 was set at 400° C. and 200° C., respectively, heating begun and the reactor system was pressurized with hydrogen at 300 psi. The reaction was started and flow of propanoic acid was at about 1.0 ml/min. Hydrogen flow was at 4.8 SLPM and reactor pressure at 300 psia hydrogen. The ketonization reactor 1 maximum temperature was at 402° C. and average over its entire length was about 360° C. The hydrogenation reactor 2 maximum temperature was 233° C. and average temperature was 220° C. over its entire length.

Product of the reaction was analyzed on a GCMS indicating a mixture with 65% 3-pentanol including other C₄₋₈ alcohols with about 72% alcohols. Other products were 13% C₇₋₁₄ aromatics and about 4% pentanone. GCMS qualitative analysis of products formed is shown in Table 32 and also presents a theoretical estimation of the calorific value of a mixture.

TABLE 32

GCMS data of propanoic acid Ketonization-hydrogenation products with estimation of calorific value of th emixture

| # of C's | Ketones | | | Alcohols | | | Alkanes | |
|---|---|---|---|---|---|---|---|---|
| | % by wt | Net Energy MJ/KG | weighted Net Energy MJ/KG | % by wt | Net Energy MJ/KG | weighted Net Energy MJ/KG | % by wt | Net Energy MJ/KG |
| ? | | | | | | | | |
| 1 | | | | | | | | |
| 2 | | | | | | | | |
| 3 | | | | | | | | |
| 4 | | | | 2.58% | 36.00 | 0.93 | | |
| 5 | 4.23% | 36.00 | 1.52 | 64.97% | 37.80 | 24.56 | | |
| 6 | | | | 3.78% | 39.10 | 1.48 | | |
| 7 | | | | 0.50% | 40.10 | 0.20 | 1.20% | 48.20 |
| 8 | | | | 1.08% | 40.70 | 0.44 | | |
| 9 | | | | | | | | |
| 10 | | | | | | | | |
| 11 | | | | | | | | |
| 12 | | | | | | | 0.38% | 47.50 |
| 13 | | | | | | | | |
| 14 | | | | | | | | |
| 15 | | | | | | | | |
| 16 | | | | | | | | |
| 17 | | | | | | | | |

TABLE 32-continued

GCMS data of propanoic acid Ketonization-hydrogenation products with estimation of calorific value of th emixture

| 18 | | | | | | | | |
| 19 | | | | | | | | |
| 20 | | | | | | | | |
| TOTAL | 4.23% | 36.00 | 1.52 | 72.91% | 38.74 | 27.61 | 1.58% | 47.85 |

| | Alkanes | Aromatics | | | TOTAL | | |
|---|---|---|---|---|---|---|---|
| # of C's | weighted Net Energy MJ/KG | % by wt | Net Energy MJ/KG | weighted Net Energy MJ/KG | % by wt | Net Energy MJ/KG | weighted Energy MJ/KG |
| ? | | | | | 1.7% | 35.00 | 0.59 |
| 1 | | | | | | | |
| 2 | | | | | | | |
| 3 | | | | | | | |
| 4 | | | | | 2.9% | 32.42 | 0.93 |
| 5 | | | | | 72.0% | 34.97 | 25.18 |
| 6 | | 0.55% | 41.90 | 0.23 | 6.1% | 36.31 | 2.22 |
| 7 | 0.58 | | | | 1.7% | 44.15 | 0.75 |
| 8 | | | | | 2.0% | 32.59 | 0.64 |
| 9 | | 1.16% | 41.48 | 0.48 | 1.2% | 41.48 | 0.48 |
| 10 | | 3.00% | 41.93 | 1.26 | 3.0% | 41.93 | 1.26 |
| 11 | | 0.70% | 42.25 | 0.30 | 0.7% | 42.25 | 0.30 |
| 12 | 0.18 | 0.61% | 41.54 | 0.25 | 1.0% | 44.52 | 0.44 |
| 13 | | 5.79% | 41.05 | 2.38 | 5.8% | 41.05 | 2.38 |
| 14 | | 2.03% | 42.10 | 0.86 | 2.0% | 42.10 | 0.86 |
| 15 | | | | | | | |
| 16 | | | | | | | |
| 17 | | | | | | | |
| 18 | | | | | | | |
| 19 | | | | | | | |
| 20 | | | | | | | |
| TOTAL | 0.76 | 13.86% | 41.75 | 5.76 | 100% | 39.43 | 36.01 |

Carbonylation of Alcohols to Acids:

The reaction system consists of a) a liquid-phase carbonylation reactor, b) a methyl iodide-acetic acid splitter column, and c) a flasher. The latter two systems are employed to recover catalyst solutions, methyl iodide and methyl acetate and separate product acetic acid. The carbonylation reactor consists of a stirred autoclave within which the reacting liquid contents are maintained at constant level of approximately 1800 ml with contents analyzed periodically. Into this reactor are fed methanol, sufficient water and recycled catalyst solution from the flasher and recycled methyl acetate and methyl iodide from the acetic acid methyl iodide splitter column. The composition of the reaction medium is maintained such that there is 13-16% methyl iodide, 4-5 wt. % methyl acetate, 19-19.5 wt. % lithium iodide, 4-5 wt. % water, and 310 to 335 ppm rhodium with the balance of the composition acetic acid which is drawn off as it formed. CO gas containing some hydrogen with a partial pressure of about 20 psi is fed continuously to the system as the mixture is agitated for thorough mixing of gases as reactor pressure is kept at 28 atmospheres with reactor temperature at 189-191° C. Reaction medium is distilled out and acetic acid separated to yield about 14 gram moles of acetic acid/hr/lit of reaction medium. See Torrence et al, U.S. Pat. No. 4,994,608.

Direct Conversion of Methanol to Ethanol:

The autoclave is charged with 0.52 g of rhodium dicarbonyl acetylacetonate, $Rh(CO_2)acac$, (2 mmol), 0.82 g of ruthenium trichloride hydrate, 0.82 g of 1,3bis (diphenylphosphino)propane (2 mmol), 2.5 mL of methyl iodide (40.1 mmol) and 40 mL of methanol. The reactor contents are then heated to 140° C. and the pressure adjusted to 1,000 psig using a $H_2$:CO mixture having a 2:1 mole ratio. The reaction is continued for 2.75 hours at 975±25 psig and stopped, during which period 3,350 psig of synthesis gas is consumed. The reactor is then cooled and recovered. Analysis of the recovered liquid product indicates formation and presence of about 27.5% ethanol, 10.1% acetaldehyde, 10.2% ethyl acetate, 11.5% methyl acetate, 2.5% acetic acid, 0.5% dimethyl acetal, 1.7% diethyl ether, 11.9% dimethyl ether 17.5% methanol and 2.9% methyl iodide. See Wegman et al, U.S. Pat. No. 4,727,200.

Carbonylation of Ethanol:

The catalyst, $RhCl_3.3H_2O$ at conc. of $7.63 \times 10^{-6}$ mol $cm^{-3}$, ethanol at conc. of $0.69 \times 10^{-2}$ mol $cm^{-3}$ and hydroiodic acid at concentration of $0.11 \times 10^{-2}$ mol are dissolved in water. The solution is then charged into the reactor, flushed with carbon monoxide and the contents heated to 200° C. temperature within ten minutes. The reactor is pressurized with 2-3 atm of carbon monoxide and the reaction was started by switching on the stirrer. Pressure in the reactor was maintained using a constant pressure regulator between the reactor and the gas reservoir. The progress of the reaction was followed by observing the pressure drop in the reservoir as a function of time. The liquid samples were taken periodically and also analyzed by GC. After absorption 0.7 moles of CO, an analysis of a liquid phase showed a complete consumption of ethanol and formation of propionic acid with 99% selectivity at about $0.7 \times 10^{-2}$ mol/$cm^{-3}$ concentration. See Dake et al, Journal of Molecular Catalysis, 24 (1984) 99-113.

While a number of exemplary embodiments, aspects and variations have been provided herein, those of skill in the art will recognize certain modifications, permutations, additions and combinations and certain sub-combinations of the embodiments, aspects and variations. It is intended that the following claims are interpreted to include all such modifications, permutations, additions and combinations and certain sub-combinations of the embodiments, aspects and variations are within their scope. The entire disclosures of all documents cited throughout this application are incorporated herein by reference.

REFERENCES

1. Organic Synthesis, Coll. Vol. 3, pp 508 (1955).
2. Organic Synthesis, Vol. 20, pp 26 (1940). Organic Synthesis, Coll. Vol. 3, pp 508 (1955).
3. Organic Letters, 2004, 6(3), 373-376.
4. Journal of American Chemical Society, 2002, 124(7), 1174-5.
5. Journal of American Chemical Society, 2010, 132(33), 11412-3.
6. The Chemistry of Ketenes, Allenes and Related Compounds, Part 1, 292 John Wiley and Sons, New York (1980).
7. Japan patent, No 47-25065.
8. Journal of Chemical Society, 1952, pp 2563-2568, The Preparation and Dimerization of Methylketene, Jenkins, A. D.
9. Recent advances in process and catalysis for the production of acetic acid, Appl.Cat.A: General, 221, 253-265, 2001.

What is claimed is:

1. A method for the preparation of a mixture of alkyl compounds, the method comprising:
a) preparing a ketene of the formula I:

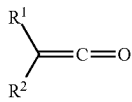

b) reacting the ketene in a self-addition reaction to form a diketene of the formula II; and

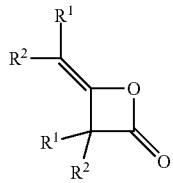

wherein:
each $R^1$ is independently H or $C_{1-6}$ alkyl; and
each $R^2$ is independently H or $C_{1-6}$ alkyl;
c) hydrogenating the diketene of the formula II in the presence of a metal catalyst to form the mixture of alkyl compounds comprising 1-butanol, 2-butanol, 2-pentanol, 1-hexanol, 2-hexanol, 2-heptanol, 4-heptanol, 3-methyl cyclohexanol, and 2,6-dimethyl-4-heptanol.

2. The method of claim 1, wherein $R^1$ and $R^2$ are hydrogen.

3. The method of claim 1, wherein the metal catalyst is a transition metal.

4. The method of claim 1, wherein the metal catalyst is selected from the group consisting of a copper catalyst, a nickel catalyst, a chromium catalyst and a zinc catalyst, or a mixture of copper, nickel and zinc catalyst.

5. The method of claim 1, wherein the mixture of alkyl compound is further purified to produce a fuel.

6. A method for the preparation of 1-butanol, 2-butanol or a mixture thereof, the method comprising:
a) preparing a ketene of the formula I:

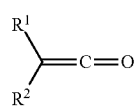

b) reacting the ketene in a self-addition reaction to form a diketene of the formula II;

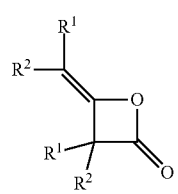

wherein:
each $R^1$ is independently H or $C_{1-6}$ alkyl; and
each $R^2$ is independently H or $C_{1-6}$ alkyl;
c) the diketene of the formula II is further reacted with R—OH, wherein R—OH is methanol or butanol, to form an acetoacetate ester of the formula III; and

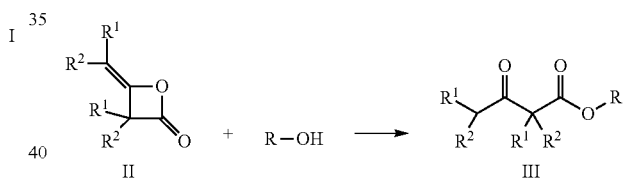

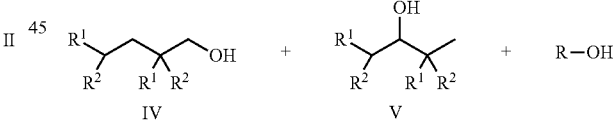

d) the acetoacetate ester of the formula III is reduced in the presence of a metal to form 1-butanol or 2-butanol of the formula IV or V and R—OH, or mixtures thereof.

7. The method of claim 6, wherein the metal in step d) is a transition metal.

8. The method of claim 7, wherein the transition metal is a copper-zinc based catalyst.

9. A method for the preparation of an alkyl compound or mixtures thereof, the method comprising:
a) preparing a ketene of the formula I:

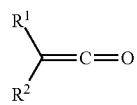

b) reacting the ketene in a self-addition reaction to form a diketene of the formula II;

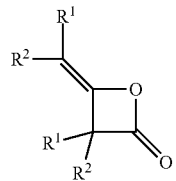

wherein:
each $R^1$ is independently H or $C_{1-6}$ alkyl; and
each $R^2$ is independently H or $C_{1-6}$ alkyl; and
c) converting the diketene of the formula II to dehydroacetic acid; and
d) reducing the dehydroacetic acid in the presence of a catalyst to form a composition comprising the alkyl compounds or mixtures thereof.

10. The method of claim 9, wherein the catalyst is a transition metal catalyst.

11. The method of claim 9, wherein the method may be performed in a single reactor or two or more reactors.

12. The method of claim 10, wherein the catalyst is selected from the group consisting of a copper chromite barium catalyst, a copper based catalyst and a zinc based catalyst and mixtures thereof.

13. The method of claim 9, wherein the alkyl compound is selected from the group consisting of 2-heptanol, 4-heptanol, and heptane, and mixtures thereof.

14. The method claim 9, further comprising:
a) dehydrating the product selected from the group comprising 2-heptanol, 4-heptanol, and mixtures thereof to provide a mixture of unsaturated hydrocarbons; and
b) the unsaturated hydrocarbons are hydrogenated to form a mixture of hydrocarbons.

* * * * *